US012742204B2

(12) United States Patent
Kennedy et al.

(10) Patent No.: US 12,742,204 B2
(45) Date of Patent: Sep. 22, 2026

(54) SEQUENCING METHODS WITH PARTITIONING

(71) Applicant: GUARDANT HEALTH, INC., Palo Alto, CA (US)

(72) Inventors: Andrew Kennedy, San Diego, CA (US); Marcin Pawel Sikora, Burlingame, CA (US)

(73) Assignee: GUARDANT HEALTH, INC., Palo Alto, CA (US)

( * ) Notice: Subject to any disclaimer, the term of this patent is extended or adjusted under 35 U.S.C. 154(b) by 0 days.

(21) Appl. No.: 19/362,211

(22) Filed: Oct. 17, 2025

(65) Prior Publication Data

US 2026/0043078 A1 Feb. 12, 2026

Related U.S. Application Data

(63) Continuation of application No. 19/249,710, filed on Jun. 25, 2025, now Pat. No. 12,467,087, which is a continuation of application No. PCT/US2025/035226, filed on Jun. 25, 2025.

(60) Provisional application No. 63/808,244, filed on May 19, 2025, provisional application No. 63/750,120, filed on Jan. 27, 2025, provisional application No. 63/735,547, filed on Dec. 18, 2024, provisional application No. 63/664,061, filed on Jun. 25, 2024.

(51) Int. Cl.
*C12P 19/34* (2006.01)
*C12Q 1/6806* (2018.01)
*C12Q 1/6869* (2018.01)

(52) U.S. Cl.
CPC ......... *C12Q 1/6869* (2013.01); *C12Q 1/6806* (2013.01)

(58) Field of Classification Search
CPC .................................................... C12Q 1/6869
See application file for complete search history.

(56) References Cited

U.S. PATENT DOCUMENTS 7,741,463 B2 6/2010 Gormley et al.
8,673,562 B2 3/2014 Drmanac
8,765,375 B2 7/2014 Drmanac
8,765,379 B2 7/2014 Drmanac
8,771,957 B2 7/2014 Drmanac
9,514,272 B2 12/2016 Kermani et al.
9,637,784 B2 5/2017 Drmanac
10,125,392 B2 11/2018 Drmanac
10,155,939 B1 12/2018 Vaisvila et al.
10,479,986 B2 11/2019 Epstein et al.
10,822,651 B2 11/2020 Jamshidi et al.
11,414,702 B2 8/2022 Drmanac
11,479,815 B2 10/2022 Osborne
2015/0322508 A1 11/2015 Mitne Neto et al.
2015/0376605 A1 12/2015 Jarosz et al.
2016/0257984 A1 9/2016 Hardenbol et al.
2018/0030532 A1 2/2018 Jiang et al.
2018/0127804 A1 5/2018 Dean et al.
2019/0323088 A1 10/2019 Boutet et al.
2019/0371429 A1 12/2019 Azab et al.
2020/0370129 A1 11/2020 Quinn et al.
2021/0214781 A1 7/2021 Patel
2022/0005547 A1 1/2022 Ye et al.
2022/0316005 A1 10/2022 Vogelstein et al.
2022/0411865 A1 12/2022 Drmanac
2023/0065345 A1 3/2023 Osborne
2023/0138633 A1 5/2023 Kruusmaa et al.
2023/0235391 A1 7/2023 Lebofsky et al.
2024/0043919 A1 2/2024 Pan et al.

FOREIGN PATENT DOCUMENTS

CN 116529394 A 8/2023
EP 2463386 B1 6/2012
WO 2012142213 A2 10/2012
WO 2013142389 A1 9/2013
WO 2014039556 A1 3/2014
WO 2014100866 A1 7/2014
WO 2014149134 A2 9/2014
WO 2014210353 A2 12/2014
WO 2015100427 A1 7/2015
WO 2015200871 A1 12/2015
WO 2016090266 A1 6/2016
WO 2016138148 A1 9/2016
WO 2017037656 A1 3/2017
WO 2017106768 A1 6/2017
WO 2017132438 A1 8/2017
WO 2018081604 A1 5/2018
WO 2018119452 A2 6/2018

(Continued)

OTHER PUBLICATIONS

Bae, J.H. et al. "Single duplex DNA sequencing with CODEC detects mutations with high sensitivity" Nature Genetics (2023) 55:871-879.
Gouil, Q. et al. "Latest techniques to study DNA methylation" Essays Biochem (2019) 63(6):639-648.
Liu, Y. et al., "TAPS: The Development of a Direct and Base-Resolution Sequencing Method for DNA Methylation" CS Chem. Biol. 2022, 17, 10, 2683-2685, Publication Date: Oct. 4, 2022).
Needleman, S.B. et al. "A general method applicable to the search for similarities in the amino acid sequence of two proteins" J. Mol. Biol. (1970) 48:443-453.
Pardoll, D.M. "The blockade of immune checkpoints in cancer immunotherapy" Nature Rev Cancer (2012) 12:252-264.
Siravegna, G. et al. "Integrating liquid biopsies into the management of cancer" Nature Reviews Clinical Oncology (2017) 14:531-548.

(Continued)

*Primary Examiner* — Kenneth R Horlick
(74) *Attorney, Agent, or Firm* — Timothy A. Hott

(57) ABSTRACT

Sequencing methods for sequencing populations of nucleic acid molecules in which sequencing reads of amplicons are grouped into families according to the nucleic acid molecule of origin by partitioning, sample indexes and information from the sequencing reads, such as start and end points. The methods described herein provide many advantages over other sequencing analysis methods, including the identification of sequencing reads deriving from the same nucleic acid in the original sample while minimizing the number of aliquots that are processed.

20 Claims, 23 Drawing Sheets

(56) References Cited

FOREIGN PATENT DOCUMENTS

| | | | |
|---|---|---|---|
| WO | 2023023402 | A2 | 2/2023 |
| WO | 2023239733 | A1 | 12/2023 |
| WO | 2024015869 | A2 | 1/2024 |
| WO | 2024137527 | A1 | 6/2024 |
| WO | 2024145249 | | 7/2024 |

OTHER PUBLICATIONS

Vaisvila, R. et al., "Enzymatic methyl sequencing detects DNA methylation at single-base resolution from picograms of DNA" Genome Res. Jul. 2021;31(7):1280-1289.
International Search Report and Written Opinion for International Patent Application No. PCT/US2025/035226 dated Jan. 23, 2025.

ratio of
unique start-stops
to molecules
1.00
0.95
0.90
0.85
0.80
0.75
0.70
0.65
0
1000
2000
3000
4000
5000
6000
7000
8000
Coverage (in molecules)

44 samples with 0.1 -60ng DNA
ligate adapter w/ sample indexes
pool + split into 48 partitions
pool
amplify enrich
add partition indexes
combine for sequencing
sequencing pool
flowcell
22 samples with 0.1 -60ng DNA
ligate adapters w/ molecular barcodes
amplify enrich
add sample indexes
combine for sequencing
sequencing pool
flowcell
0.1 ng
0.2 ng
0.5 ng
1 ng
2 ng
5 ng
10 ng
15 ng
20 ng
40 ng
60 ng On-target reads
pool-partition protocol
'molecular barcoding protocol
On-target reads
$10^8$
$10^7$
$10^6$
$10^5$
$10^4$
0.1
0.2
0.5
1
2
5
10
15
20
40
60
Input (ng)

Molecular recovery
pool-partition protocol
'molecular barcoding protocol
Molecular recovery (%)
80
60
40
20
0
0.1
0.2
0.5
1
2
5
10
15
20
40
60
Input (ng)

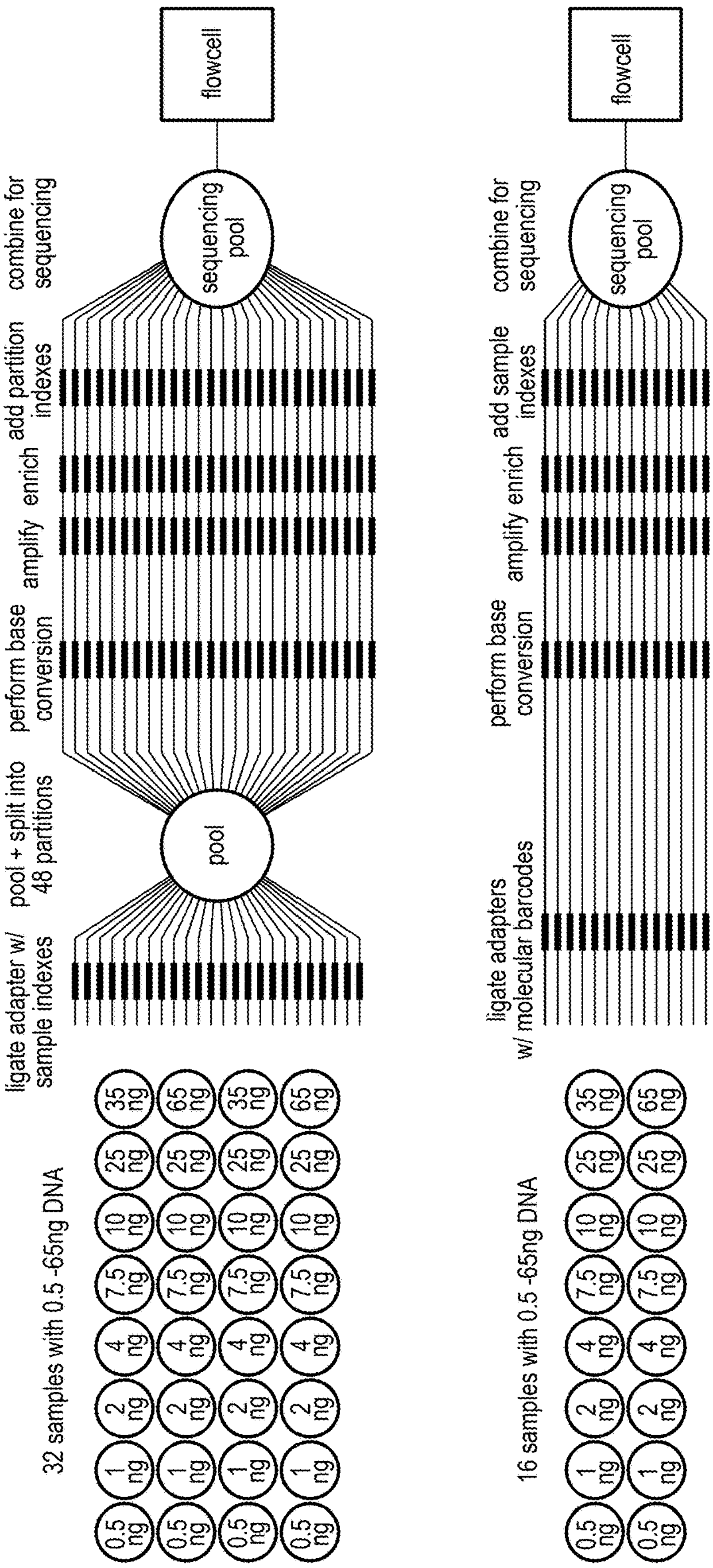

Fig. 8
32 samples with 0.5 -65ng DNA
0.5 ng
1 ng
2 ng
4 ng
7.5 ng
10 ng
25 ng
35 ng
65 ng
ligate adapter w/ sample indexes
pool + split into 48 partitions
pool
perform base conversion
amplify
enrich
add partition indexes
combine for sequencing
sequencing pool
flowcell
16 samples with 0.5 -65ng DNA
ligate adapters w/ molecular barcodes
perform base conversion
amplify enrich
add sample indexes
combine for sequencing
sequencing pool
flowcell

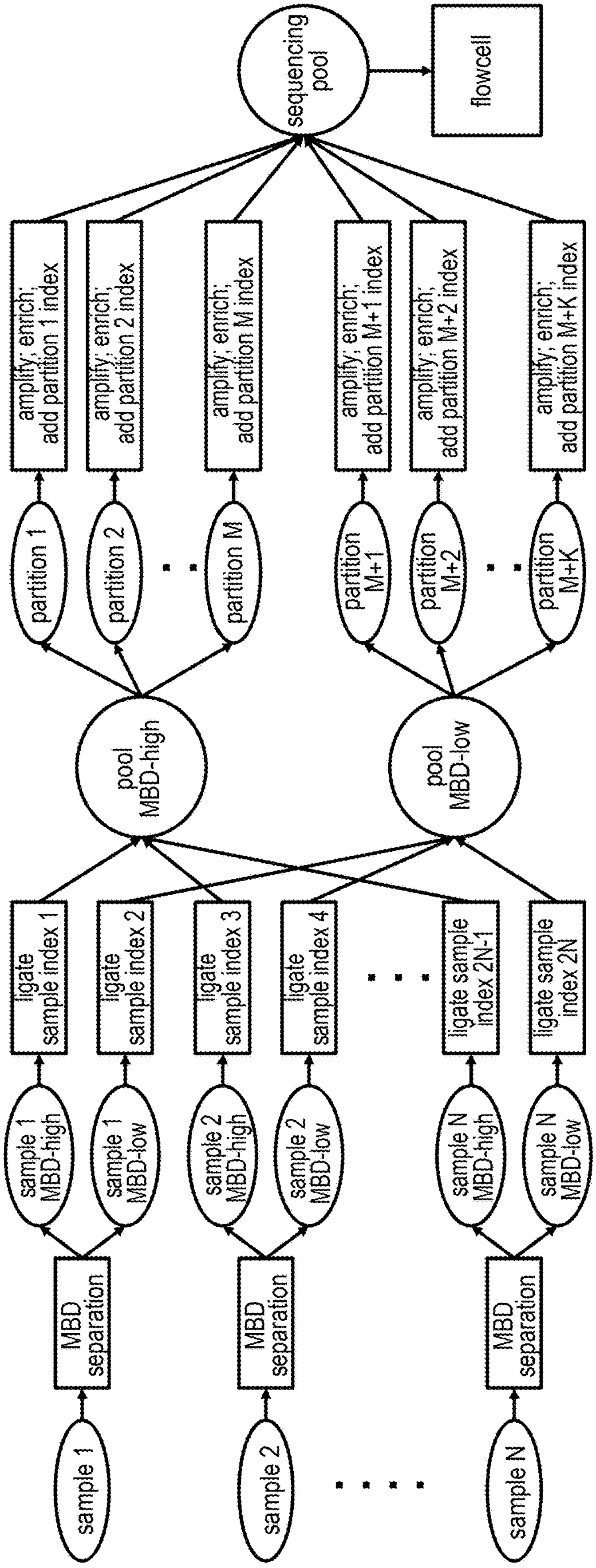

Fig. 12
sample 1
sample 2
sample N
MBD separation
MBD separation
MBD separation
sample 1 MBD-high
sample 1 MBD-low
sample 2 MBD-high
sample 2 MBD-low
sample N MBD-high
sample N MBD-low
ligate sample index 1
ligate sample index 2
ligate sample index 3
ligate sample index 4
ligate sample index 2N-1
ligate sample index 2N
pool MBD-high
pool MBD-low
partition 1
partition 2
partition M
partition M+1
partition M+2
partition M+K
amplify; enrich; add partition 1 index
amplify; enrich; add partition 2 index
amplify; enrich; add partition M index
amplify; enrich; add partition M+1 index
amplify; enrich; add partition M+2 index
amplify; enrich; add partition M+K index
sequencing pool
flowcell

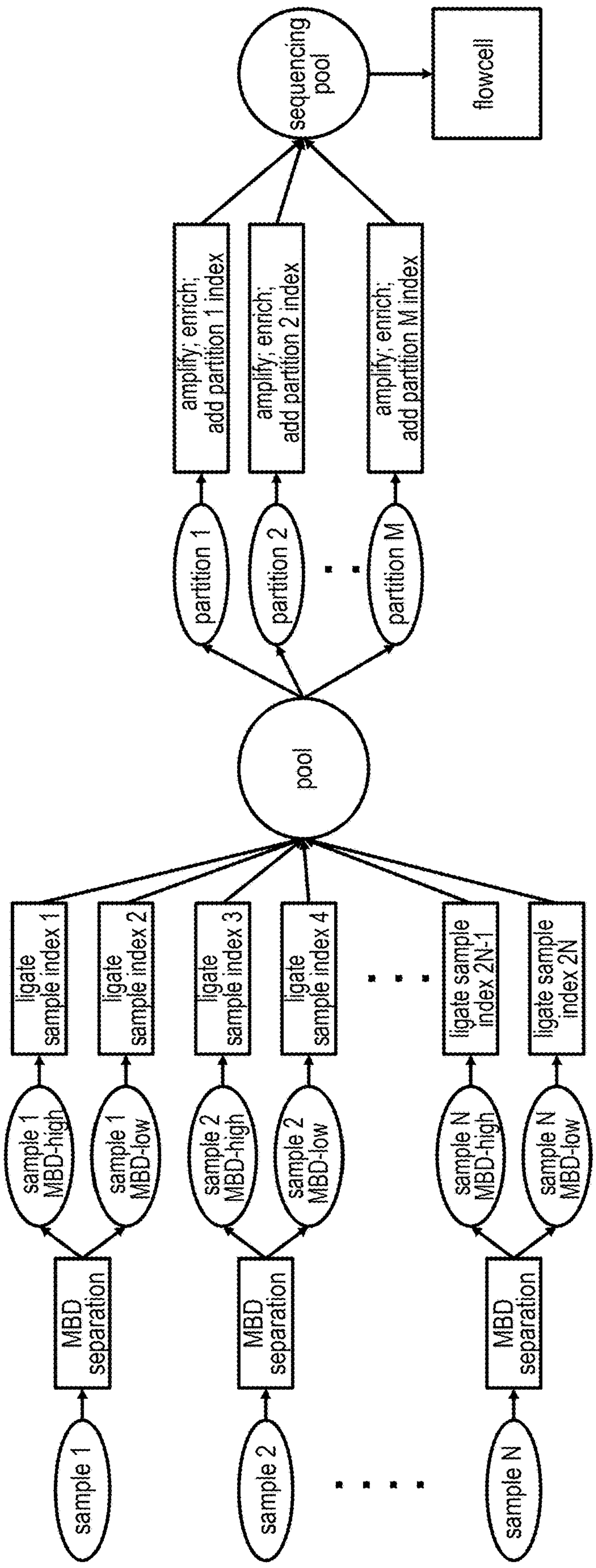

Fig. 13
sample 1
sample 2
sample N
MBD separation
MBD separation
MBD separation
sample 1 MBD-high
sample 1 MBD-low
sample 2 MBD-high
sample 2 MBD-low
sample N MBD-high
sample N MBD-low
ligate sample index 1
ligate sample index 2
ligate sample index 3
ligate sample index 4
ligate sample index 2N-1
ligate sample index 2N
pool
partition 1
partition 2
partition M
amplify; enrich; add partition 1 index
amplify; enrich; add partition 2 index
amplify; enrich; add partition M index
sequencing pool
flowcell Fig. 15A Mixed partitioning core
*sample tag in ligation, combine all samples and distribute reduced diversity of each into multiple aliquots*
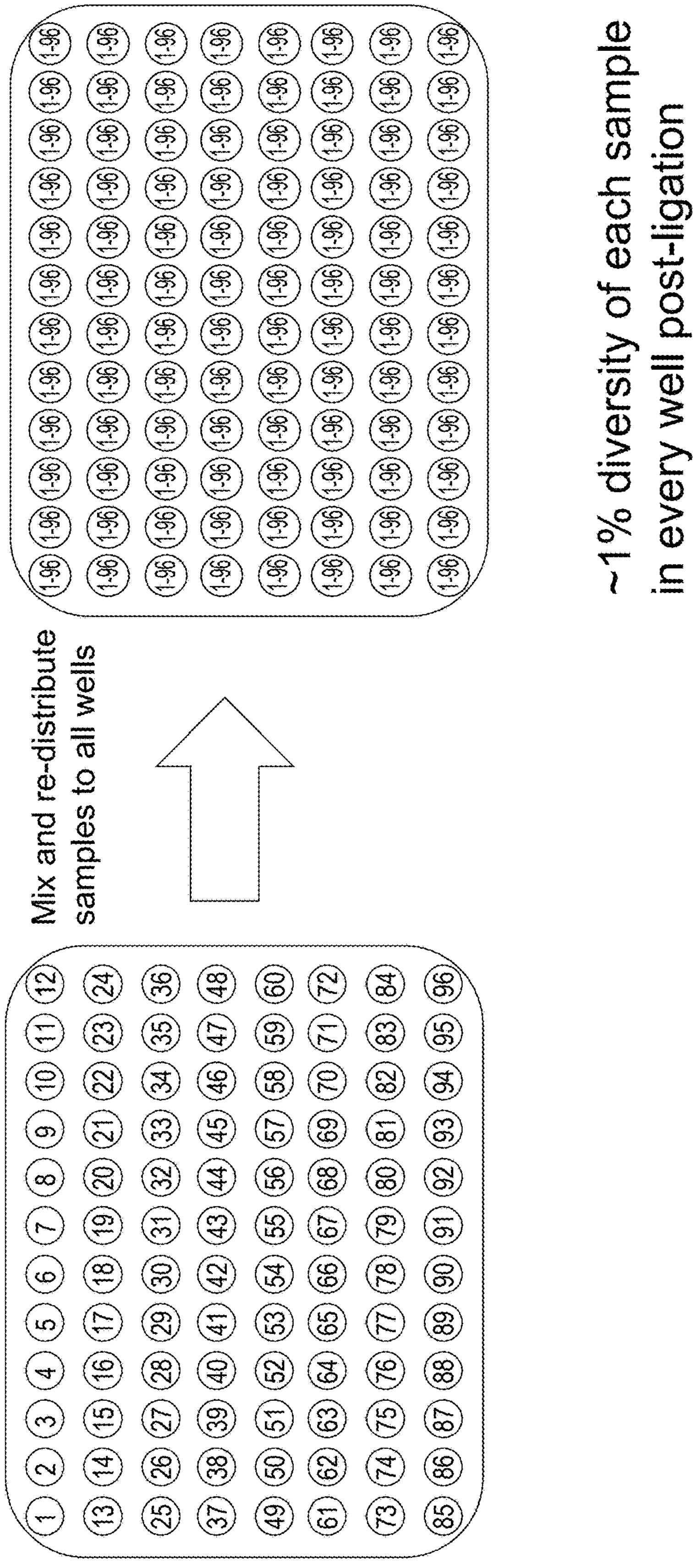

Fig. 15B Variation #1: Unique partition well tagging in PCR
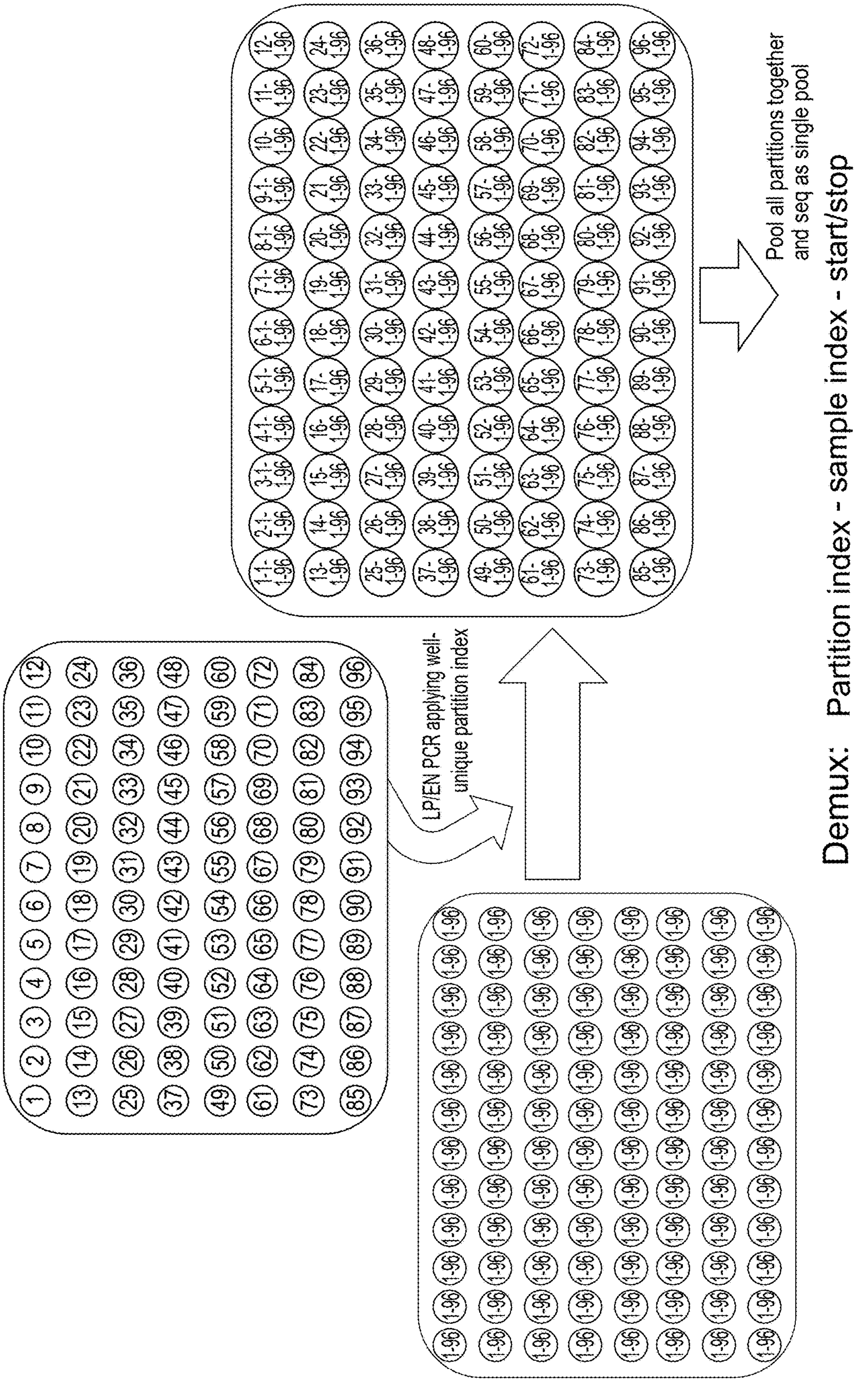

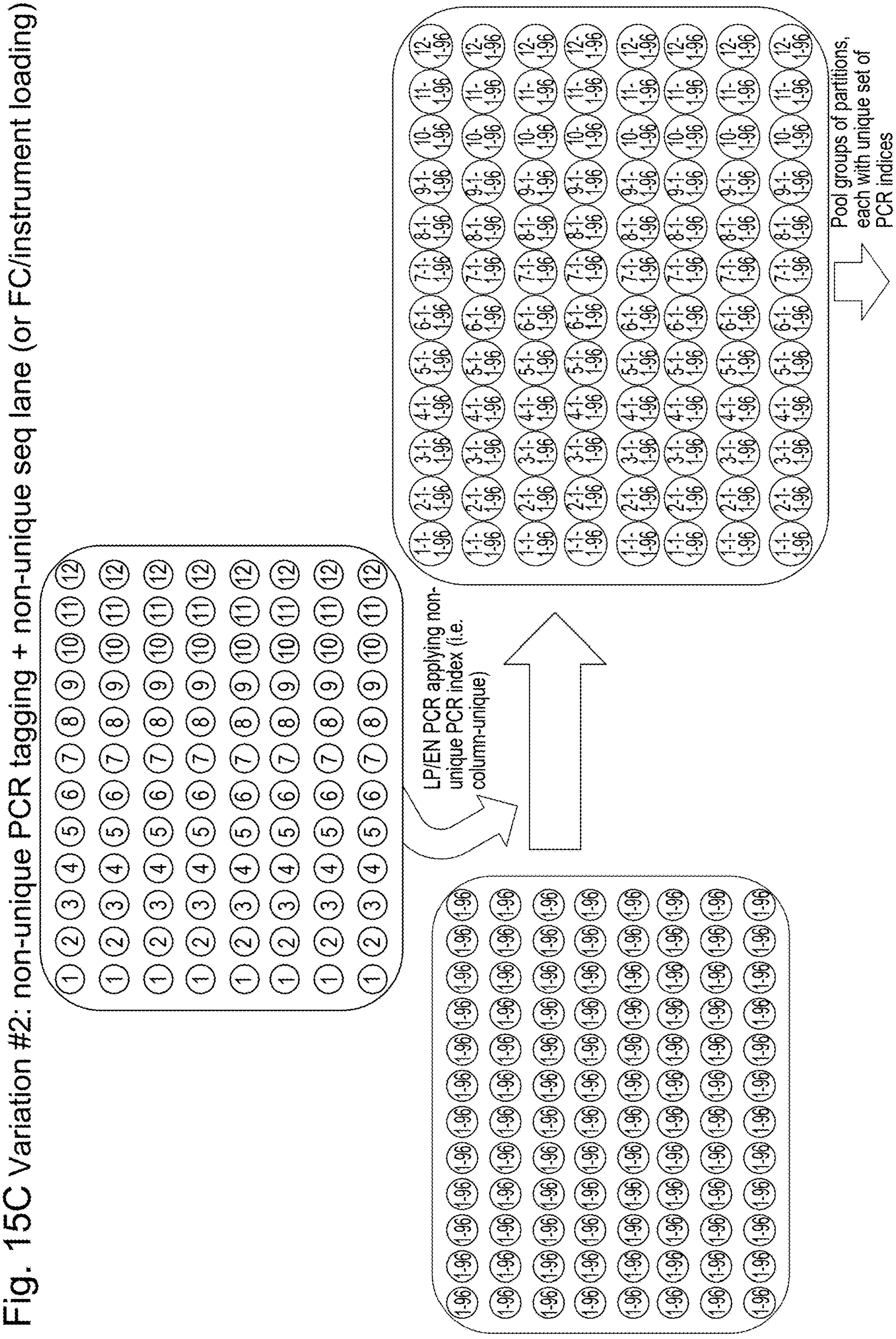
Fig. 15C Variation #2: non-unique PCR tagging + non-unique seq lane (or FC/instrument loading)
LP/EN PCR applying non-unique PCR index (i.e. column-unique)
Pool groups of partitions, each with unique set of PCR indices Fig. 15D Variation #2: non-unique PCR tagging + non-unique seq lane (or FC/instrument loading)
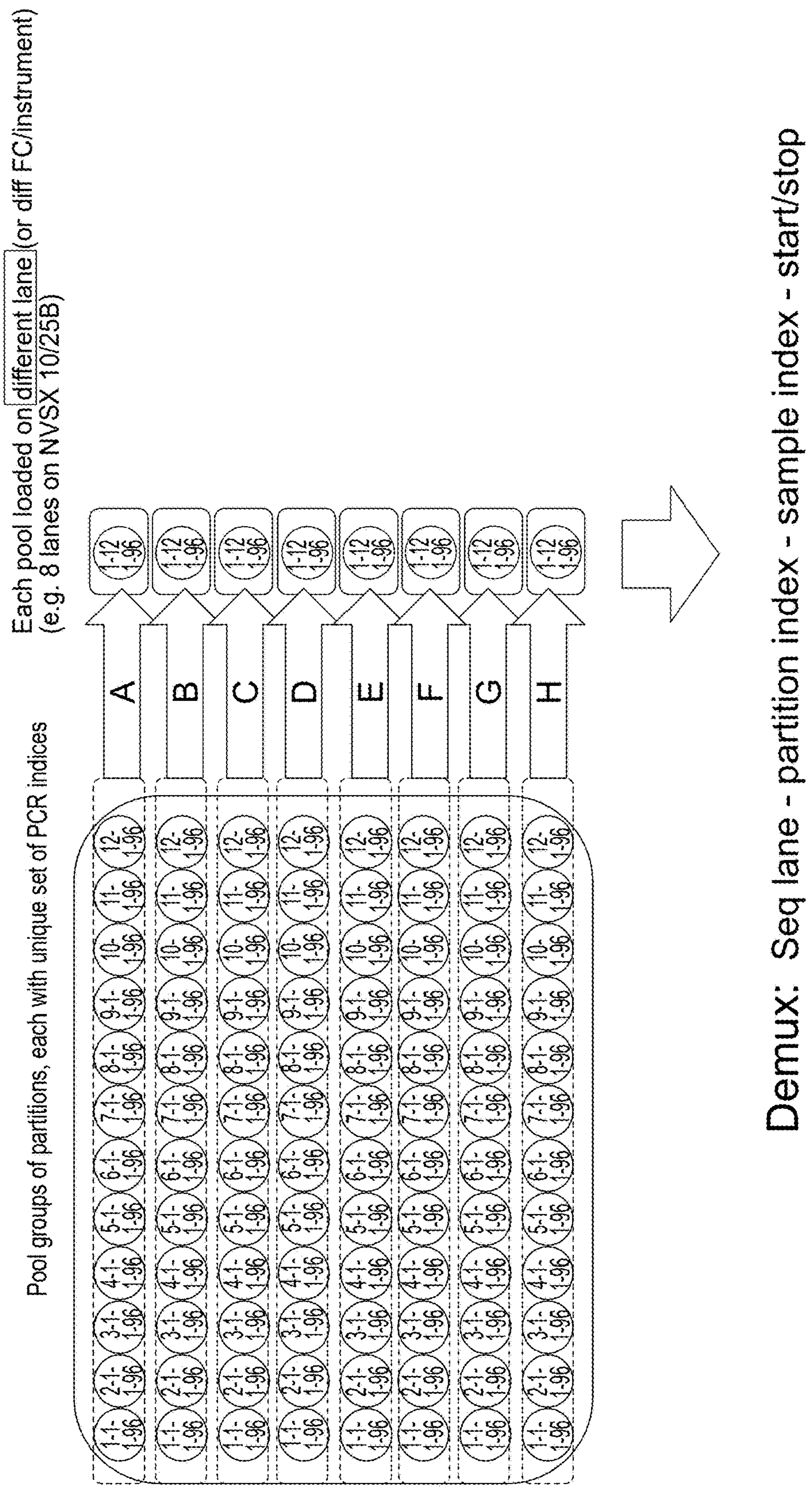

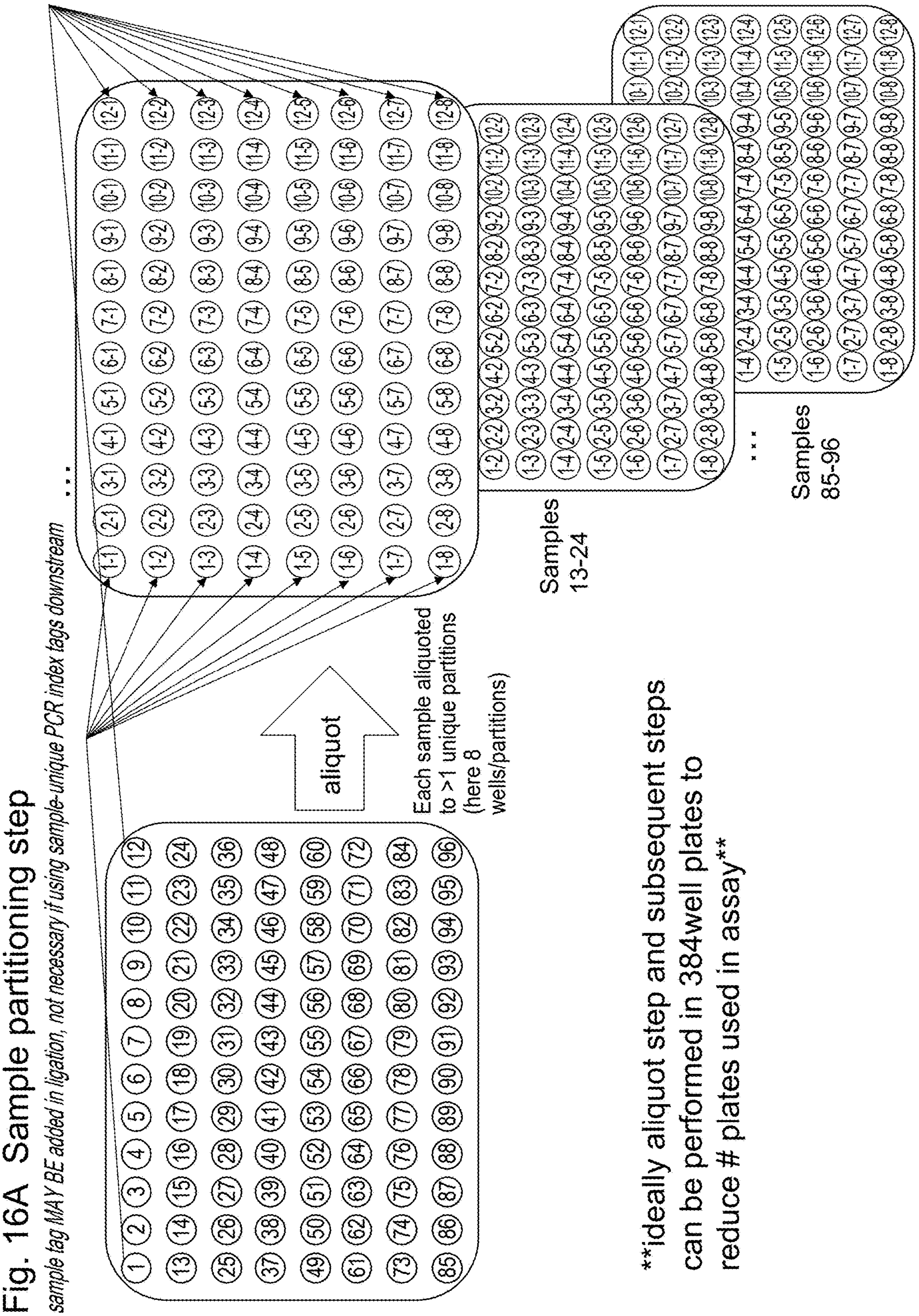
Fig. 16A Sample partitioning step
sample tag MAY BE added in ligation, not necessary if using sample-unique PCR index tags downstream
aliquot
Each sample aliquoted to >1 unique partitions (here 8 wells/partitions)
Samples 13-24
Samples 85-96
ideally aliquot step and subsequent steps can be performed in 384well plates to reduce # plates used in assay

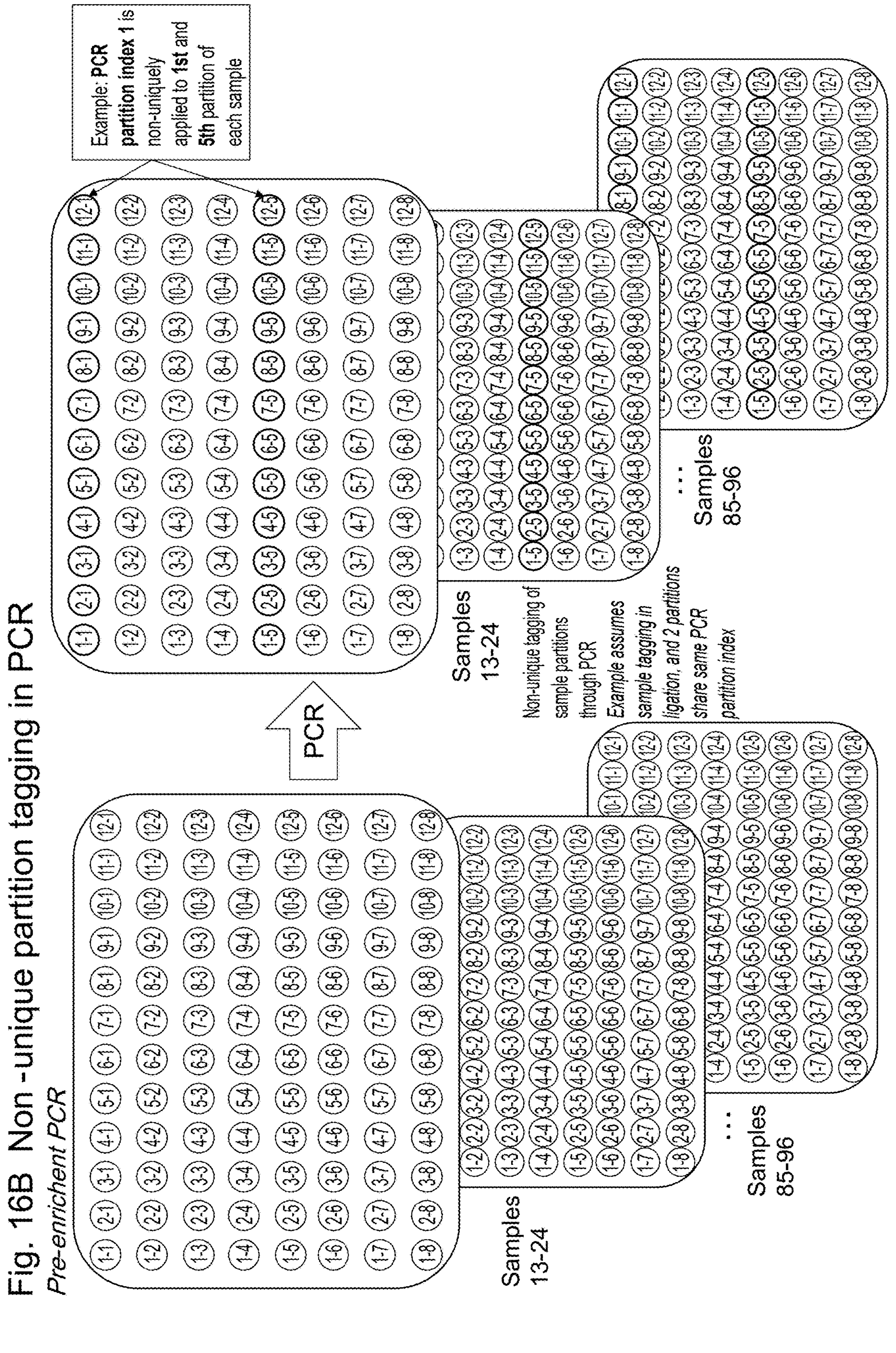
Fig. 16B Non -unique partition tagging in PCR
Pre-enrichent PCR
Samples 13-24
...
Samples 85-96
PCR
Example: PCR partition index 1 is non-uniquely applied to 1st and 5th partition of each sample
Samples 13-24
Non-unique tagging of sample partitions through PCR
Example assumes sample tagging in ligation, and 2 partitions share same PCR partition index
...
Samples 85-96

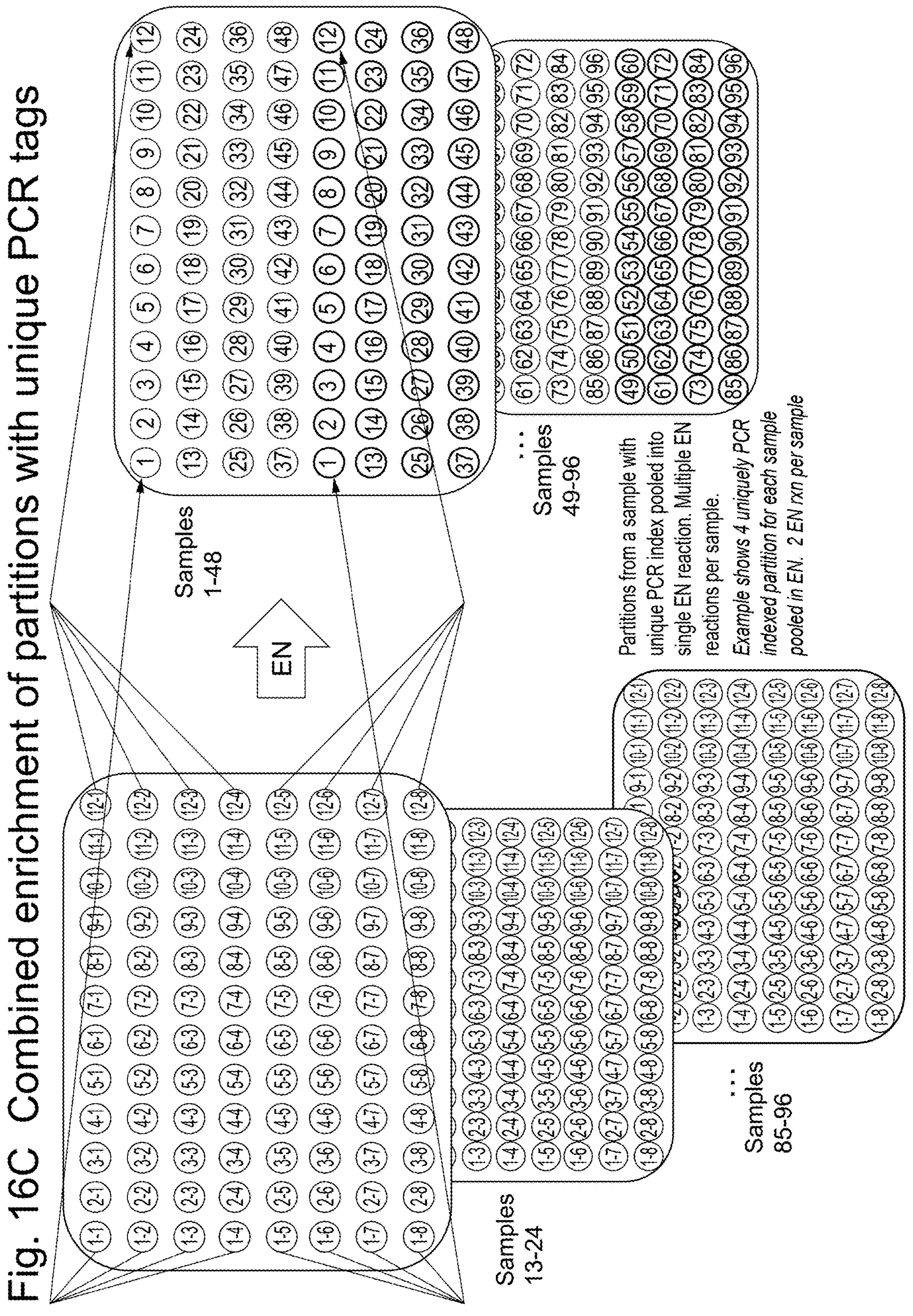
Fig. 16C Combined enrichment of partitions with unique PCR tags
Samples 1-48
Samples 49-96
Samples 13-24
Samples 85-96
EN
Partitions from a sample with unique PCR index pooled into single EN reaction. Multiple EN reactions per sample.
Example shows 4 uniquely PCR indexed partition for each sample pooled in EN. 2 EN rxn per sample Fig. 16D Enrichment reactions physically partitioned in NGS (unique seq lane(s) / flowcell)

Each of the enrichment reactions of a sample is loaded on a different lane (or different set of lanes, or different flowcell), enrichment reactions from different samples are multiplexed in sequencing.

*Example: Each sample has 2 EN reactions, 1st EN rxn from all samples pooled and loaded on lane 1 of sequencer, while all 2nd EN rxns from samples are loaded on lane 2.*

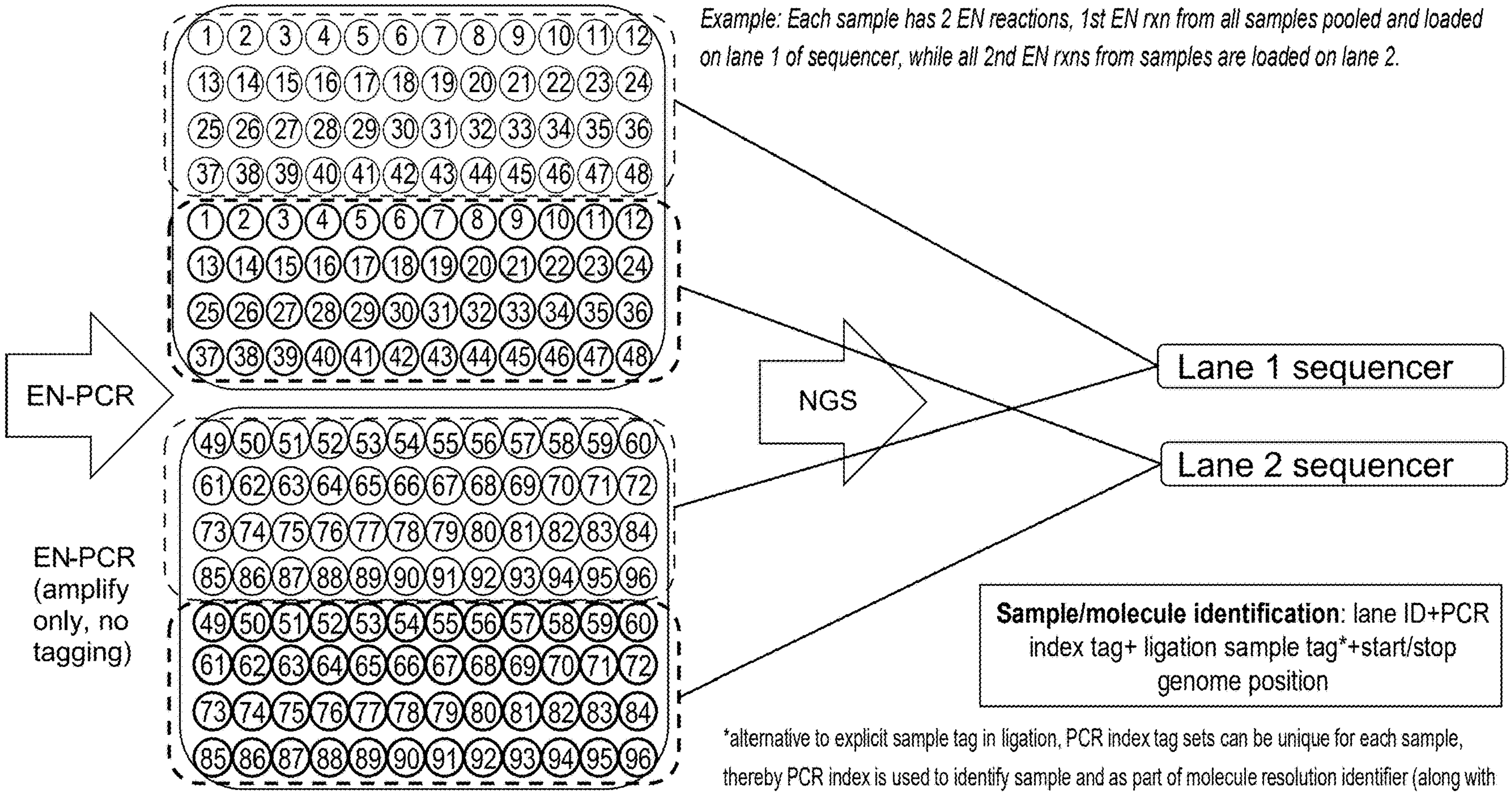

*alternative to explicit sample tag in ligation, PCR index tag sets can be unique for each sample, thereby PCR index is used to identify sample and as part of molecule resolution identifier (along with lane ID and start/stop)

SEQUENCING METHODS WITH PARTITIONING

CROSS-REFERENCE TO RELATED APPLICATIONS

This application is a continuation application of U.S. application Ser. No. 19/249,710, filed Jun. 25, 2025, now U.S. Pat. No. 12,467,087, issued Nov. 11, 2025, which is a continuation of PCT Application No. PCT/US2025/035226, filed Jun. 25, 2025, which claims the benefit of, and relies on the priority date of, U.S. Provisional Patent Application Nos. 63/808,244, filed May 19, 2025, 63/750,120, filed Jan. 27, 2025, 63/735,547, filed Dec. 18, 2024, and 63/664,061, filed Jun. 25, 2024, which are incorporated by reference in their entirety for all purposes.

BACKGROUND

A tumor is an abnormal growth of cells. Fragmented DNA is often released into bodily fluid when cells, such as tumor cells, die. Thus, some of the cell-free DNA in body fluids is tumor DNA. A tumor can be benign or malignant. A malignant tumor is often referred to as a cancer.

Cancer is a major disease worldwide. Each year, tens of millions of people are diagnosed with cancer around the world, and more than half eventually die from it. In many countries, cancer ranks as the second most common cause of death following cardiovascular diseases. Early detection is associated with improved outcomes for many cancers.

Cancer is caused by the accumulation of mutations and/or epigenetic variations within an individual's normal cells, at least some of which result in improperly regulated cell division. Such mutations commonly include copy number variations (CNVs), copy number aberrations (CNA), single nucleotide variations (SNVs), gene fusions and indels, and epigenetic variations include modifications to the 5th atom of the 6-atom ring of cytosine and association of DNA with chromatin and transcription factors.

Cancers are often detected by biopsies of tumors followed by analysis of cells, markers or DNA extracted from cells. But more recently it has been proposed that cancers can also be detected from cell-free nucleic acids in body fluids, such as blood or urine (see, e.g., Siravegna et al., Nature Reviews Clinical Oncology 14, 531-548 (2017)). Such tests have the advantage that they are non-invasive and can be performed without identifying suspected cancer cells through biopsy. However, such tests are complicated by the fact that the number of nucleic acids in body fluids is very low and the nucleic acids within them are diverse.

Sequencing methods have been reported in which nucleic acid molecules in a sample are contacted with a set of molecular barcodes, which randomly assort among the nucleic acid molecules, such that substantially all of the molecules or at least substantially all of the identical molecules within the sample are linked to different molecular barcodes (see, e.g., WO2014/039556; WO2014149134). The nucleic acid molecules linked to molecular barcodes are then subject to amplification and sequencing. The molecular barcodes facilitate grouping of amplicons of the same original molecule because all have the same barcode pair. Grouping of amplicons according to original molecule facilitates distinction between errors arising in amplification and sequencing and genuine genetic variation present in original sample molecule. Grouping of amplicons according to original molecule can also be advantageous in counting applications (e.g. copy number variation analysis) because counting the number of families rather than the number of sequencing reads can address biases, such as amplification biases.

SUMMARY OF THE CLAIMED INVENTION

The invention is set out in the appended set of claims.

The invention provides a method of sequencing comprising: (a) linking sample indexes to nucleic acid molecules in a plurality of samples, wherein nucleic acid molecules in the same sample receive the same sample index and nucleic acid molecules in different samples receive different sample indexes; (b) partitioning the pooled nucleic acid molecules into a plurality of aliquots; (c) amplifying the nucleic acid molecules; (d) sequencing amplicons of the nucleic acid molecules to produce sequencing reads, wherein a sequencing read comprises a sequence of one of the nucleic acid molecules and a sample index; (e) aligning the sequencing reads to a reference sequence to determine start and stop points and/or lengths of the sequences of the nucleic acid molecules; (f) grouping sequencing reads with the same sample index into families, wherein sequencing reads in the same family have the same start and stop points and/or the same length determined in step (e), and are from the same aliquot; and (g) calling sequences or variants present in the sample from the sequencing reads grouped into families.

Optionally, the method further comprising after step (d) and before step (g) demultiplexing the sequencing reads by sample of origin from sample index portions of the reads.

Optionally, the method further comprises pooling the nucleic acid molecules from the plurality of samples after step (a), wherein step (b) comprises partitioning the pooled nucleic acid molecules into the plurality of aliquots.

Optionally, the methods further comprises after step (c) linking the nucleic acid molecules to partition indexes, whereby nucleic molecules in the same aliquot are linked to the same partition index and nucleic acid molecules in at least some of the different aliquots are linked to different partition indexes, wherein the sequencing reads further comprise sequences of the partition indexes, and the sequencing reads in a family have (i) the same start and stop points and/or the same length; (ii) the same sample index; and (iii) the same partition index. Optionally, the method further comprises pooling different aliquots that have received different partition indexes. Optionally all of the different aliquots are linked to different partition indexes, and all of the different aliquots are pooled together. Optionally, all of the different aliquots are linked to a partition index, some of the different aliquots receiving different partition indexes and some receiving the same partition index and the aliquots are grouped into subpools, the aliquots in a subpool having different partition indexes from one another and nucleic acids within a subpool are sequenced together and nucleic acids within different subpools are sequenced separately. Optionally, the sequencing reads respectively comprising sequence of a nucleic acid molecule flanked on one or both sides by sequence of a sample index flanked on both side by sequence of a partition index. Optionally, sequencing of different aliquots is performed separately. Optionally, sequencing of different aliquots is performed in different flow cells or different regions or lanes of the same flow cell. Optionally, step (g) determines a consensus sequence from the sequencing reads in a family. Optionally, the sequencing reads include sequencing reads of both strands in a family. Optionally, step (g) comprises calling a variation when the variation is present in the sequencing reads of both strands. Optionally, step (g) comprises calling a variation when the variation is present in sequencing reads of multiple families. Optionally, the number of aliquots is 2-1500, 5-500, 25-100, 96 or 384. Optionally, the number of aliquots is 5-500.

Optionally, the sample indexes having a Hamming distance of at least two from one another and the partition indexes have a Hamming distance of at least two from one another.

In some methods, the sample is a cell-free DNA sample. Some methods further comprise blunt-ending DNA molecules in the cell-free DNA sample. Some methods further comprise enriching for DNA molecules from selected regions of a genome after the amplifying step. Some methods further comprise convert unmethylated C's to U's after partitioning and before amplifying. In some methods, the sample includes at least 100 billion different molecules and has an estimated mean number of molecules of the same start and stop points of between 1.5 and 3 and an estimated maximum number of molecules of the same start and stop points of between 100 and 1000.

Optionally, the partition indexes are components of a forward and/or a reverse primer. Optionally, the sample indexes are components of an adapter.

Optionally, the samples are samples from different subjects.

Optionally, the method is performed without random association of indexes with sample nucleic acids.

The invention further provides a method of sequencing comprising: (a) linking sample indexes to nucleic acid molecules in a plurality of samples, wherein nucleic acid molecules in the same sample receive the same sample index and nucleic acid molecules in different samples receive different sample indexes; (b) pooling the nucleic acid molecules from the plurality of samples; (c) partitioning the pooled nucleic acid molecules into a plurality of aliquots; (d) labelling the nucleic acid molecules with partition indexes, wherein nucleic acid molecules in the same aliquot receive the same partition index and nucleic acid molecules in different aliquots receive different partition indexes; (e) amplifying the nucleic acid molecules in separate aliquots to produce amplicons; (f) pooling the aliquots; (g) sequencing the amplicons to produce sequencing reads, wherein a sequencing read comprises sequence of one of the nucleic acid molecules a sample index and a partition index; (h) aligning the sequence reads to a reference sequence to determine start and stop points of the sequences of the nucleic acid molecules; (i) grouping sequencing reads having the same sample index into families, wherein sequencing reads in the same family have the same start and stop points in sequence of a nucleic acid molecule, and the same partition index; and (j) calling sequences or variations present in the sample from the sequencing reads grouped into families.

Optionally, step (j) determines a consensus sequence from the sequencing reads in a family. Optionally, the sequencing reads include sequencing reads of both strands in a family. Optionally, step (j) comprises calling a variation when the variation is present in the sequencing reads of both strands. Optionally, step (j) comprises calling a variation when the variation is present in sequencing reads of multiple families. Optionally, the number of aliquots is 2-1500, 5-500, 25-100, 96 or 384. Optionally, the number of aliquots is 5-500.

Optionally, the sample indexes have a Hamming distance of at least two from one another and the partition indexes have a Hamming distance of at least two from one another. Optionally, the sample is a cell-free DNA sample. Optionally, the method further comprises blunt-ending DNA molecules in the cell-free DNA sample. Optionally, the method further comprises enriching for DNA molecules from selected regions of a genome after the amplifying step. Optionally, the method further comprises treating with bisulfite to convert unmethylated C's to U's performed after partitioning and before amplifying. Optionally, the sample includes at least 100 billion different molecules and has an estimated mean number of molecules of the same start and stop points of between 1.5 and 3 and an estimated maximum number of molecules of the same start and stop points of between 100 and 1000.

Optionally, the partition indexes are components of a forward and/or a reverse primer. Optionally, the sample indexes are components of an adapter.

Optionally, the samples are samples from different subjects.

Optionally, the method is performed without random association of indexes with sample nucleic acids.

The invention further provides a method of sequencing comprising: (a) for each of a plurality of samples comprising nucleic acid molecules, partitioning the sample into a plurality of aliquots; (b) labelling the aliquots with partition indexes, wherein different aliquots of the same sample receive different partition indexes, (c) for each sample, pooling subsets of aliquots for the sample to form a plurality of pools for each sample; (d) for each sample, subjecting its different pools to different enrichment reactions to form enriched pools; (e) sequencing nucleic acid molecules in the enriched pools to provide sequencing reads, wherein a sequencing read includes a sequence of a nucleic acid molecule from one of the samples and a partition index; (f) aligning the sequence reads to a reference sequence to determine start and stop points and/or lengths of the sequences of the nucleic acid molecules; (g) grouping sequencing reads having the same partition index and the same start and stop points and/or length determined in step (f); and (h) calling sequences or variants present in the samples from the sequencing reads grouped into families.

Optionally, the method further comprises labelling the samples with sample indexes before partitioning wherein different samples receive different sample indexes. Optionally, the labelling is performed by ligation. Optionally, the partition indexes are tags on primers and the labelling occurs by amplification of the nucleic acid molecules. Optionally, the partitions of different samples receive the same sets of partition indexes. Optionally, the partitions of different samples receive different sets of partition indexes, whereby the partition indexes distinguish among aliquots of the same sample and among aliquots of different samples. Optionally, the method further comprises pooling pools of the samples that have been for will be subject to the same enrichment reaction. Optionally, the pooling occurs between the partitioning and the enrichment. Optionally the pooling occurs between the enrichment and sequencing. Optionally, the different enrichment reactions comprise enrichment by affinity to different oligonucleotides or different sets of oligonucleotides. Optionally, each sample is partitioned into at least ten aliquots and each pool of a sample is formed by pooling at least five of the aliquots. Optionally, each sample is partitioned into at least 4 aliquots and each pool of a sample is formed by pooling at least two of the aliquots. Optionally, the partitioning involves transfer of aliquots between microtiter plate wells.

The invention further provides a method of sequencing comprising: (a) for each of a plurality of samples comprising nucleic acid molecules, partitioning the sample into a plurality of aliquots; (b) for each aliquot of each sample, sequencing nucleic acid molecules in the aliquot to provide sequencing reads, wherein a sequencing read includes a sequence of a nucleic acid molecule from one of the samples; (c) aligning the sequence reads to a reference sequence to determine start and stop points and/or lengths of the sequences of the nucleic acid molecules; (d) grouping sequencing reads from the same aliquot and having the same start and stop points and/or length determined in step (c) and (e) calling sequences or variants present in the samples from the sequencing reads grouped into families.

The invention further provides a method of sequencing comprising: (a) ligating a concatenating adapter comprising a sample index to nucleic acid molecules in a plurality of samples, wherein nucleic acid molecules in the same sample receive the same sample index and nucleic acid molecules in different samples receive different sample indexes; (b) extending 3' ends of the concatenating adapter ligated to the nucleic acid molecules to form double-stranded concatemers in which one strand comprises an original Watson strand and complement of an original Crick strand of one of the nucleic acid molecules, and the other strand comprises the original Crick strand and complement of the Watson strand of the nucleic molecule; (c) partitioning the double-stranded concatemers into a plurality of aliquots so that each aliquot receives double-stranded concatemers formed from nucleic acid molecules from each sample; (d) amplifying the double-stranded concatemers; (e) sequencing amplicons of the double-stranded concatemers to produce sequencing reads, wherein a sequencing read comprises a sequence of both strands of one of the nucleic acid molecules in tandem and a sample index; (f) aligning the sequencing reads to a reference sequence to determine start and stop points and/or lengths of the sequences of the nucleic acid molecules; (g) grouping sequencing reads having the same sample index into families, wherein sequencing reads in the same family have the same start and stop points and/or the same length determined in step (f), and are from the same aliquot; and (h) calling sequences or variants present in the sample from the sequencing reads grouped into families.

Optionally, the method further comprises after step (e) and before step (h) demultiplexing the sequencing reads by sample of origin from sample index portions of the reads. Optionally, the method further comprises pooling the double-stranded concatemers from the plurality of samples after step (b), wherein step (c) comprises partitioning the pooled nucleic acid molecules into the plurality of aliquots. Optionally, the method further comprises after step (d) linking the double-stranded concatemers to partition indexes, whereby double-stranded concatemers in the same aliquot are linked to the same partition index and double-stranded concatemers in at least some of the different aliquots are linked to different partition indexes, wherein the sequencing reads further comprise sequences of the partition indexes, and the sequencing reads in a family have the same start and stop points and the same partition index. Optionally, the method further comprises pooling different aliquots that have received different partition indexes. Optionally, all of the different aliquots are linked to different partition indexes, and all of the different aliquots are pooled together. Optionally, all of the different aliquots are linked to a partition index, some of the different aliquots receiving different partition indexes and some receiving the same partition index and the aliquots are grouped into subpools, the aliquots in a subpool having different partition indexes from one another; wherein double-stranded concatemers within a subpool are sequenced together and double-stranded concatemers within different subpools are sequenced separately. Optionally, sequencing of different aliquots is performed separately. Optionally, sequencing of different aliquots is performed in different flow cells or different regions or lanes of the same flow cell. Optionally, step (h) determines a consensus sequence from the sequencing reads in a family. Optionally, step (h) comprises calling a variation when the variation is present in the sequencing reads of both strands. Optionally, step (h) comprises calling a variation when the variation is present in sequencing reads of multiple families. Optionally, the concatenating adapter comprises first and second oligonucleotides comprising mutually complementary 3' ends duplexed with one another, a third oligonucleotide comprising a 3' end and a 5' tail, the 3' end being duplexed with the 5' end of the first oligonucleotide, a fourth oligonucleotide comprising a 3' end a 5' tail, the 3' end being duplexed with the 5' end of the second oligonucleotide, wherein the 5' ends of the first and second oligonucleotides are ligated to the 3' ends of the nucleic acid molecules, and the 3' ends of the first and second oligonucleotides undergo a strand displacement extension reaction to generate the double-stranded concatemers.

In some embodiments, the nucleic acid molecules or a portion thereof is contacted with an agent that recognizes methyl cytosine in the DNA. In particular embodiments, the agent that recognizes methyl cytosine is a methyl binding reagent. In particular embodiments, the methyl binding reagent is a methyl binding domain (MBD) protein or an antibody. In some embodiments, the methyl binding reagent specifically recognizes 5-methylcytosine. In some embodiments, the nucleic acid molecules or a portion thereof is contacted with the agent before the linking of sample indexes. In some embodiments, the nucleic acid molecules or a portion thereof is contacted with the agent after the linking of sample indexes but before the partitioning the nucleic acid molecules into a plurality of aliquots. In some embodiments, the nucleic acid molecules or a portion thereof is contacted with the agent after the linking of sample indexes and after pooling the nucleic acid molecules from the plurality of samples after indexing, but before the partitioning of the pooled nucleic acid molecules into a plurality of aliquots. In some embodiments, the nucleic acid molecules or a portion thereof is contacted with the agent after the partitioning the nucleic acid molecules into a plurality of aliquots.

In some embodiments of the disclosed methods, the nucleic acid molecules are subjected to a procedure that affects a first nucleobase in the nucleic acid differently from a second nucleobase. In particular embodiments, the first nucleobase is a modified or unmodified nucleobase, the second nucleobase is a modified or unmodified nucleobase different from the first nucleobase, and the first nucleobase and the second nucleobase have the same base pairing specificity. In particular embodiments, the first nucleobase is an unmodified cytosine and the second nucleobase is a modified cytosine, optionally wherein the modified cytosine is 5-methylcytosine or 5-hydroxymethylcytosine. In some embodiments, the nucleic acid molecules are subjected to the procedure before the linking of sample indexes. In some embodiments, the nucleic acid molecules are subjected to the procedure after the linking of sample indexes but before the partitioning the nucleic acid molecules into a plurality of aliquots. In some embodiments, the nucleic acid molecules are subjected to the procedure after the linking of sample indexes and after pooling the nucleic acid molecules from the plurality of samples after indexing, but before the partitioning the pooled nucleic acid molecules into a plurality of aliquots. In some embodiments, the nucleic acid molecules are subjected to the procedure after the partitioning the nucleic acid molecules into a plurality of aliquots.

In some embodiments, the procedure that affects a first nucleobase of the nucleic acid differently from a second nucleobase of the nucleic acid is a methylation-sensitive conversion. In particular embodiments, the methylation-sensitive conversion is bisulfite conversion, oxidative bisulfite (Ox-BS) conversion, Tet-assisted bisulfite (TAB) conversion, APOBEC-coupled epigenetic (ACE) conversion, enzymatic methyl-seq (EM-seq) conversion, single-enzyme 5-methylcytosine sequencing (SEM-seq) conversion, or direct methylation sequencing (DM-seq).

Some embodiments of the disclosed methods further comprise contacting the nucleic acid molecules with at least one nuclease, such as prior to the capturing or prior to the sequencing. In some embodiments, the at least one nuclease comprises at least one restriction enzyme. In some embodiments, the at least one nuclease comprises at least one methylation-sensitive restriction enzyme (MSRE) and/or at least one methylation-dependent restriction enzyme (MDRE).

In some embodiments, partitioning can comprise both binary partitioning and partitioning based on degree/level of modifications. For example, methylated fragments in a DNA sample can be partitioned by methylated DNA immunoprecipitation (MeDIP), or methylated fragments can be partitioned from unmethylated fragments using methyl binding domain proteins (e.g., MethylMinder Methylated DNA Enrichment Kit (ThermoFisher Scientific). Subsequently, additional partitioning may involve eluting fragments having different levels of methylation by adjusting the salt concentration in a solution with the methyl binding domain and bound fragments. As salt concentration increases, fragments having greater methylation levels are eluted.

In one aspect, the invention provides a method of sequencing comprising: (a) linking sample indexes to nucleic acid molecules in a plurality of samples, wherein nucleic acid molecules in the same sample receive the same sample index and nucleic acid molecules in different samples receive different sample indexes; (b) partitioning the nucleic acid molecules into a plurality of aliquots so that each aliquot receives nucleic acid molecules from two or more of the plurality of samples; (c) amplifying the nucleic acid molecules; (d) sequencing amplicons of the nucleic acid molecules to produce sequencing reads, wherein a sequencing read comprises a sequence of one of the nucleic acid molecules and a sample index; (e) grouping sequencing reads using at least the sample index, wherein sequencing reads within a group are from the same aliquot and are derived from the same starting molecule in the plurality of samples; and (f) calling sequences or variants present in the sample from the sequencing reads grouped into families.

In one aspect, the present disclosure provides a method comprising: (a) partitioning parent nucleic acids from a sample of a subject into a plurality of aliquots, wherein the parent nucleic acids are tagged with a population of first indices having two or more different index sequences in the population, wherein the tagging is before or after partitioning; (b) labelling the aliquots of parent nucleic acids or amplification products thereof with partition indices, wherein the partition indices are aliquot-specific with respect to the plurality of aliquots; (c) pooling the aliquots to generate a pool; (d) sequencing nucleic acids or amplification products thereof of the pool; and (e) aligning sequencing reads to a reference sequence and deconvoluting sequencing reads as originating from individual parent nucleic acids based at least on alignment position, the partition index, and the first indices.

In one aspect, the present disclosure provides a method comprising: (a) partitioning parent nucleic acids from a sample of a subject into a plurality of aliquots, optionally wherein the parent nucleic acids are tagged with a population of first indices before or after partitioning; (b) labelling the aliquots of parent nucleic acids or amplification products thereof with partition indices, wherein the plurality of aliquots comprises two or more subsets of aliquots and partition indices are aliquot-specific within a subset but not across subsets; (c) for each subset, pooling the aliquots of that subset to generate a plurality of subset pools; (d) sequencing nucleic acids or amplification products thereof of the subset pools, wherein subset pools deriving from the same sample are sequenced separately; and (e) aligning sequencing reads to a reference sequence and deconvoluting sequencing reads as originating from individual parent nucleic acids based at least on alignment position, the partition index, and the separate sequencing.

Optionally, the parent nucleic acids are tagged with a population of first indices having two or more different index sequences in the population; and wherein the deconvoluting is further based on the first indices. Optionally, each subset of aliquots of a sample is tagged with the same set of partition indices. Optionally, the plurality of aliquots comprises two subsets of aliquots and the number of different index sequences in the set of partition indices is half the number of aliquots. Optionally, the method further comprises subjecting the pool or the subset pools to enrichment before sequencing, for example wherein the enrichment is by hybrid capture with target-specific oligonucleotide probes; optionally wherein different sequences are enriched in different subset pools.

The invention further provides a method comprising: (a) partitioning parent nucleic acids from a sample of a subject into a plurality of aliquots, wherein the parent nucleic acids are tagged with a population of first indices having two or more different index sequences in the population, wherein the tagging is before or after partitioning; (b) amplifying the partitioned parent nucleic acids with primers, optionally wherein the primers comprise sample-specific indices; (c) sequencing nucleic acids or amplification products thereof of the aliquots, wherein aliquots deriving from the same sample are sequenced separately; and (d) aligning sequencing reads to a reference sequence and deconvoluting sequencing reads as originating from individual parent nucleic acids based at least on alignment position, first indices, and the separate sequencing; and wherein the deconvoluting is not based on partition indices.

Optionally, the method further comprises subjecting the aliquots to enrichment before sequencing, for example wherein the enrichment is by hybrid capture with target-specific oligonucleotide probes; optionally wherein different sequences are enriched in different aliquots.

Optionally, the deconvoluting comprises grouping sequencing reads into families of sequencing reads having the same alignment position, such as the same start and stop points, the same index sequence(s), and optionally deriving from the same sequencing reaction.

Optionally, the method further comprises generating consensus sequences for individual parent nucleic acids from the deconvoluted sequencing reads. Optionally, the method further comprises detecting genetic variants or epigenetic variants from the deconvoluted sequencing reads or the consensus sequences, for example wherein the variants are somatic variants.

Optionally the parent nucleic acids are cell-free DNA. Optionally, the parent nucleic acids in step (a) are (A) 100 ng or less of cell-free DNA, for example 65 ng or less of cell-free DNA, for example 60 ng or less of cell-free DNA, or (B) 25-100 ng of cell-free DNA; for example 25-65 ng of cell-free DNA, for example 25-60 ng of cell-free DNA.

Optionally, the plurality of aliquots is 16 aliquots or fewer; for example 12 aliquots or fewer; for example 8 aliquots or fewer; for example 4 aliquots or fewer. Optionally, the method uses between 4 and 16, between 4 and 12, between 4 and 8, or 4 aliquots for cell-free DNA of more than 5 ng; and optionally 2 or 3 aliquots for cell-free DNA of less than 5 ng.

Optionally, the method uses 4 or fewer different index sequences in the population of first indices; for example 2-4 different index sequences in the population of first indices; for example 2 different index sequences in the population of first indices. Optionally, the method comprises tagging with a variable number of different index sequences in the population of first indices, for example wherein the number of different index sequences in the population of first indices is increased for (i) sample input amounts above a threshold amount relative to sample input amounts below the threshold amount, and/or (ii) somatic single nucleotide variation detection and/or somatic indel detection relative to counting applications such as copy number variation detection.

Optionally, the threshold amount is between 25-100 ng of cell-free DNA, for example wherein the threshold amount is 25 ng, 60 ng, 65 ng, or 100 ng of cell-free DNA.

Optionally, the tagging with first indices is before partitioning. Optionally, the tagging with first indices is by ligation of adapters comprising the first indices. Optionally, the labelling with partition indices is by amplification with primers comprising the partition indices. Optionally, the separate sequencing is by sequencing in separate sequencing machines, in separate flow cells, or in separate lanes of a flow cell.

Optionally, the method is performed on a plurality of samples of one or more subjects, wherein the method uses sample-specific indices, wherein the method comprises sample multiplexing after tagging or labelling with the sample-specific indices, and wherein the method comprises demultiplexing of sequencing reads to different samples based on the sample-specific indices. Optionally, the first indices are sample-specific, and optionally each subset of aliquots of each sample is tagged with the same set of partition indices, or (ii) the partition indices are sample-specific. Optionally, the first indices are sample-specific and wherein the sample multiplexing after the tagging with sample-specific first indices comprises mixing of parent nucleic acids from different samples before or during partitioning.

Optionally, before partitioning, the method comprises methylation-based separation of the parent nucleic acids of the sample into at least a hypomethylation fraction and a hypermethylation fraction. Optionally, the methylation-based separation is performed before tagging with first indices and the first indices are methylation fraction-specific, wherein the method comprises methylation fraction multiplexing after tagging with the first indices, and wherein the method comprises demultiplexing of sequencing reads to different methylation fractions based on the first indices. Optionally, the population of first indices used for tagging the hypomethylation fraction has a higher number of different index sequences than the population of first indices used for tagging the hypermethylation fraction, for example wherein the hypomethylation fraction is tagged with a population of first indices having two different index sequences in the population and the hypermethylation fraction is tagged with a population of first indices wherein each first index in the population has the same index sequence.

Optionally, wherein at least the partitioning, labelling with partition indices, and pooling are carried out separately for each methylation fraction deriving from the same sample.

Optionally, the enrichment comprises a first enrichment and a second enrichment, wherein the first enrichment is performed on a portion of the hypermethylation fraction and targets an epigenetic target region set; and the second enrichment is performed on the hypomethylation fraction and another portion of the hypermethylation fraction and targets a sequence-variable target region set, optionally wherein the second enrichment is performed on a pool of the hypomethylation fraction and the another portion of the hypermethylation fraction.

Optionally, the parent nucleic acids or amplification products thereof are subjected to a procedure that affects a first nucleobase in the nucleic acid differently from a second nucleobase, for example wherein the first nucleobase is a modified or unmodified nucleobase, the second nucleobase is a modified or unmodified nucleobase different from the first nucleobase, and the first nucleobase and the second nucleobase have the same base pairing specificity. Optionally, the subjecting is after methylation-based separation and/or after partitioning.

Optionally, the method is for determining the presence or absence of cancer in the subject. Optionally, the method further comprises: (A) treatment selection or matching; (B) measuring or monitoring treatment response; and/or (C) minimal residual disease (MRD) detection.

Optionally, the subject is a human subject.

Optionally, the method further comprises obtaining or providing the sample from the subject, for example wherein the sample is a blood sample.

In some embodiments, the results of the systems and methods disclosed herein are used as an input to generate a report. The report may be in a paper or electronic format. For example, genetic results as determined by the methods and systems disclosed herein, such as the presence of a nucleic acid variant was detected in a sample, can be displayed directly in such a report. In some embodiments, only the presence or absence of a disease, such as cancer, is displayed in such a report.

In some embodiments, the systems and methods disclosed herein comprise communicating an output, results or a report to a recipient such as a healthcare professional or the subject from which the sample was obtained.

The invention further provides a computer-implemented method comprising: receiving sequencing reads generated according to any of the above methods; and aligning, deconvoluting, and optionally demultiplexing the sequencing reads according to the method. The invention further provides a data processing apparatus comprising means for carrying out the method.

The invention further provides a computer program comprising instructions which, when the program is executed by a computer, cause the computer to carry out the computer-implemented method.

The invention further provides a computer-readable data carrier having stored thereon the computer program.

The various steps of the methods disclosed herein, or steps carried out by the systems disclosed herein, may be carried out at the same or different times, in the same or different geographical locations, e.g., countries, and/or by the same or different people. In some embodiments, the report is communicated to a subject, for example, a subject who has cancer and has undergone testing by the methods and systems described herein, or to a healthcare professional, such as a physician treating the subject that has cancer.

BRIEF DESCRIPTION OF THE FIGURES

FIG. 8 shows a workflow for sequencing of DNA molecules having undergone methylation-dependent nucleotide conversion.

FIGS. 12-14 show protocols for methyl-binding domain sequencing.

FIGS. 15A-D and 16A-E show exemplary protocols according to the invention.

DEFINITIONS

Figure 1:
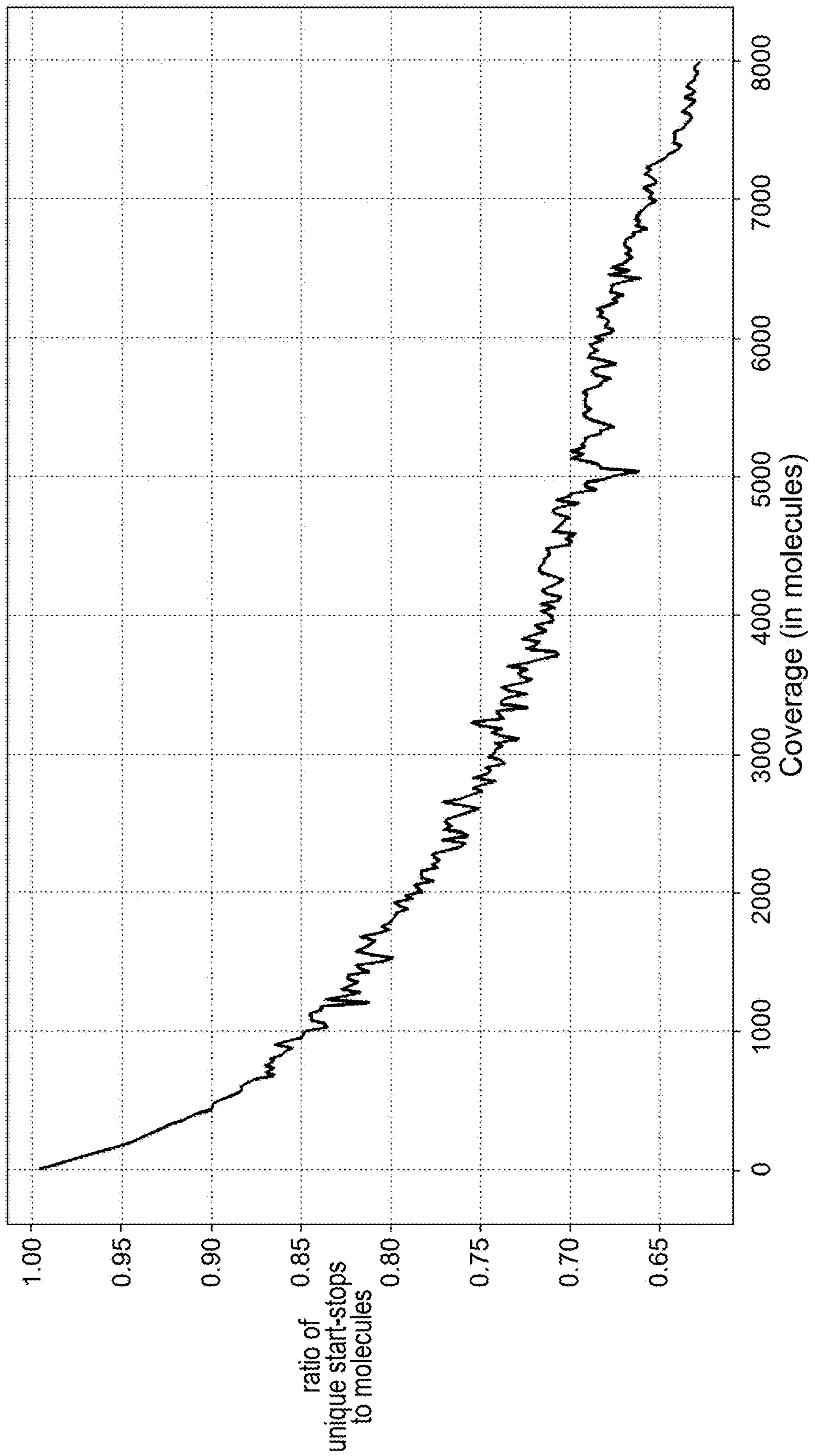
FIG. 1 shows a ratio of unique start and stop points to total nucleic acid molecules with increasing coverage (in molecules).

A subject refers to an animal, such as a mammalian species (preferably human) or avian (e.g., bird) species, or other organism, such as a plant. More specifically, a subject can be a vertebrate, e.g., a mammal such as a mouse, a primate, a simian or a human. Animals include farm animals, sport animals, and pets. A subject can be a healthy individual, an individual that has symptoms or signs or is suspected of having a disease or a predisposition to the disease, or an individual that is in need of therapy or suspected of needing therapy.

A genetic variation refers to a change in nucleotide sequence (nucleotide variation), modification, or copy number relative to that of a reference sequence, which can be e.g., an exon, gene, chromosome or full genome representing the normal sequence, modification, if any, and copy number for an organism. A genetic variation can include one or more single nucleotide variations (SNVs), insertions, deletions, repeats, small insertions, small deletions, small repeats, structural variant junctions, variable length tandem repeats, and/or flanking sequences, copy number variants (CNVs), transversions, gene fusions and other rearrangements, as well as modifications such as methylation, acetylation or hydroxymethylation are also forms of genetic variation. A variation can be a base change, insertion, deletion, repeat, copy number variation, modification, transversion, or any combination thereof.

A cancer marker is a genetic variation associated with presence or risk of developing a cancer. A cancer marker can provide an indication a subject has cancer or a higher risk of developing cancer than an age and gender matched subject of the same species that does not have the cancer marker. A cancer marker may or may not be causative of cancer.

The four standard nucleotide types refer to A, C, G, T for deoxyribonucleotides and A, C, T and U for ribonucleotides.

Within a sequencing read the terms "upstream" and "downstream" are used to indicate sequences relatively closer or further to the point of initiation of sequencing, typically a sequencing primer binding site. For example, if a sequencing read includes an upstream and downstream index, the upstream index is closer than the downstream index to the point of initiation of sequencing.

Any of the methods disclosed herein can perform grouping of sequence reads into families by any means which allows for grouping sequencing reads that are derived from the same starting molecule in the originating sample. The grouping of sequence reads can be performed using the sample index in combination with one or more of start point, stop point, length, sequence and modification status (e.g. methylation status). For example, any of the methods disclosed herein may comprise grouping sequencing reads having the same sample index into families, wherein sequencing reads in the same family have the same start points and the same length, and are from the same aliquot. For example, any of the methods disclosed herein may comprise grouping sequencing reads having the same sample index into families, wherein sequencing reads in the same family have the same stop points and the same length, and are from the same aliquot. For example, any of the methods disclosed herein may comprise grouping sequencing reads having the same sample index into families, wherein sequencing reads in the same family have the same start points and the same stop points, and are from the same aliquot. Start and stop points are a representation of the end points of alignment between a sequencing read and a reference sequence. These end points may represent the termini of nucleic acid molecules in the sample, or the termini after processing steps, such as end-repair. Thus, when a sequencing read is determined to be maximally aligned with a reference sequence, start and stop points can be represented by the end coordinates of the reference sequence aligned with the sequencing read. Genomic coordinates are consecutive numbers assigned for each chromosome by the Genome Reference Consortium of the NIH or similar body. The start and stop points are usually assigned lower and higher genomic coordinates respectively but this assignment is arbitrary and can be reversed. Start and stop points can also be represented as the end sequences of a sequencing read aligned with a reference sequence. For example, start and stop sites can comprise: (i) the first 1, first 2, the first 5, the first 10, the first 15, the first 20, the first 25, the first 30 or at least the first 30 base positions at one end of the sequencing read of a nucleic acid molecule that align to the reference sequence; and (ii) the last 1, last 2, the last 5, the last 10, the last 15, the last 20, the last 25, the last 30 or at least the last 30 base positions at the other end of the sequencing read of the nucleic acid molecule that align to the reference sequence. In one embodiment, the start and stop sites can comprise: (i) the first 5 base positions at one end of the sequence read of a nucleic acid molecule that align to the reference sequence, and (ii) the last 5 base positions at the other end of the sequence reads. The sequencing read sequence aligned with lower and higher genomic coordinates are usually considered to be start and stop points respectively, but the designations are arbitrary and can be reversed. Start and stop points can also be represented as the corresponding genomic sequences aligned with the end sequences from the sequencing read as described above. As disclosed elsewhere herein, length of the sequencing reads can be used to group sequencing reads, wherein a group corresponds to sequencing reads derived from the same original nucleic acid molecule. The length of the sequencing read refers to the distance between the start and end points of alignment between a sequencing read and a reference sequence (i.e. the portion of the sequence read corresponding to the nucleic acid molecules. Sequencing reads may be grouped if they have the same length or if they have a length within a specified range, for example +/−5 nucleotides, +/−4 nucleotides, +/−3 nucleotides, +/−2 nucleotides, or +/−1 nucleotide relative to the other sequence reads in that group. Sequencing reads may be grouped if they have a length within +/−2 nucleotides relative to the other sequence reads in that group. Allowing for this variability in length means that sequencing reads comprising amplification and/or sequencing errors which impact the length can still be included in the group. When grouping based on the length of the sequence reads, additional criteria can be included in the grouping step such as the start points, the stop point and/or the center point of the sequencing read, when aligned to a reference sequence.

Alignment of a sequencing read with a reference sequence can refer to the alignment of the entire sequencing read or a portion (e.g., at least 30 contiguous nucleotides) or portions thereof sufficient to map the sequencing read to a single location on the reference sequence. Maximal alignment between a sequencing read and reference sequence usually corresponds to 80-100% identity between the two over a window defined by the first and last genomic coordinates of the reference sequence aligning with the sequencing read. Because sequencing reads typically include a portion corresponding to a sample nucleic acid flanked by index sequences, only a central portion of the sequencing read usually aligns with the reference sequence. Thus, when it is apparent from inspection, which portion of a sequencing read corresponds to a sample nucleic acid and which to other sequences, comparison with the reference sequence can be based only on the portion corresponding to the sample nucleic acid, or end sequences thereof. Sequencing reads are aligned both from the sequence as read and its reverse complement. Sequencing reads in which either the sequence as read, or its reverse complement aligns to the same genomic coordinates are considered to have the same alignment. Alignment can be performed by any conventional alignment algorithm with default settings, such as Burrow-Wheeler Alignment Tool bwa-mem (Li H. (2013) Aligning sequence reads, clone sequences and assembly contigs with BWA-MEM. arXiv: 1303.3997v2 [q-bio.GN].). Briefly, the algorithm works by seeding alignments with maximal exact matches (MEMs) and then extending seeds with the affine-gap Smith-Waterman algorithm.

A forward primer is a primer initiating first strand synthesis from an adapter, and a reverse primer is a primer initiating second strand synthesis.

An estimated value for a sample can be based on a reference sample, or on measurement of the sample within a margin of error of measurement or on a theoretical calculation.

An aliquot is a fraction of a sample separated from the rest of the sample or other aliquots of the sample. For example, aliquots can be separated from each other by occupying separate wells of a microtiter plater. An aliquot can be generated by random partitioning the nucleic acid molecules (e.g. from a plurality of samples, or from pooled nucleic acid molecules, as described elsewhere). In other words, the partitioning of nucleic acids into aliquots is not dependent on any feature of the nucleic acids, such as length or nucleobase modification status.

Pooling refers to combining some or all initially separate samples or aliquots of samples into an undivided mixture of the combined samples. Pooling can include dynamic loading such that a fixed amount of the initially separate samples or aliquots is pooled.

Unless otherwise apparent from the context, reference to a nucleic acid can include DNA or RNA. Nucleic acid molecules isolated from nature typically contain standard nucleotides, including naturally modified forms thereof, such as methylcytosine Synthetic oligonucleotides, such as adapters, can also be formed entirely from these standard nucleotides, or can include, one or more positions occupied by analogs of these standard nucleotides, capable of base pairing with one, some or all of the standard nucleotides. Nitroindole and deoxyinosine are examples of analog nucleotides capable of pairing with any of the standard nucleotides. Some synthetic oligonucleotides, such as adapters, are formed entirely of standard nucleotides of DNA. Some synthetic oligonucleotides, such as a adapters, include uracil or deoxyuridine as well as standard DNA nucleotides. Analogs including nitroindole and deoxyinosine can also be referred to as unnatural bases.

DETAILED DESCRIPTION

I. General

The disclosure provides methods for sequencing populations of nucleic acid molecules in which sequencing reads of amplicons from the same sample are grouped into families according to the nucleic acid molecule of origin by use of partitioning and information from the sequencing reads, such as start and stop points. Partitioning avoids or reduces a need for individualized barcoding of nucleic acid molecules.

II. Workflow

The methods typically start with a plurality of samples of nucleic acid populations, for example from different subjects. The samples can be subject to various preprocessing steps, such as purification of nucleic acids from other cellular materials, exchange of solvents, additions of buffers, salts and the like suitable for e.g., annealing or polymerase activity, conversion of RNA to DNA, conversion of single-stranded DNA to double-stranded DNA and blunt-ending of DNA.

After preprocessing, if any, nucleic acid populations of each sample can be linked to a sample index, so the nucleic acid molecules in a sample receive the same sample index and nucleic acid molecules in different samples receive different sample indexes. Sample indexes can be linked to nucleic acid molecules by ligation, e.g., as a component of an adapter. A preferred method is to incorporate a sample index into an adapter, which is ligated to both ends of nucleic acid molecules in a sample so that the nucleic acid molecule becomes flanked by two adapters, each of which has the same sample index.

After attachment of sample indexes to nucleic acid molecules in samples, the samples can be pooled. The number of samples pooled can be at least 2, 5, 8, 10, 16, 25, 32, 50, 64, 96, 100, 150, 200, 250, 386, or 500 and/or the number of pooled samples can be no more than 1000, 500, 386, 250, 200, 150, 100, 96, 50, 32, 25, 16 or 10, including all combinations of upper and lower limits. The number of samples pooled may be at least 10. The number of samples pooled may be no more than 250. In some methods, the number of samples is 2-500, 10-250, or 8-96. In some methods, the number of samples is 8, 16, 32, 96, or 386. The number of samples pooled can depend on the DNA content so that the DNA content of pooled samples is within a desired range for subsequent processing. For example, an exemplary range of DNA content for individual samples is 5-30 ng for processing without conversion of unmethylated cytosine residues and 8-25 ng for processing with conversion of unmethylated cytosine residues. After pooling an exemplary DNA range for processing without conversion of unmethylated residues is 2200-3600 ng e.g., 2880 ng, and with conversion of unmethylated cytosine residues is 1900-2900, e.g., 2400 ng. Pooling can include adding a fixed amount of the samples to the pooled sample. The fixed amount can be within a range, such as +/−10% of a fixed value, +/−5% of a fixed value or +/−1% of a fixed value.

After pooling, a pooled sample is partitioned into aliquots, which results in aliquots comprising a mixture of nucleic acids from different samples. In some embodiments, sample multiplexing comprises mixing of parent nucleic acids from different samples (such as set out in the preceding paragraph) before or during partitioning. Preferably partitioning occurs before any amplification of original sample nucleic acid molecules so that amplicons of the same original molecule are not partitioned from each other. The purpose of partitioning is to reduce the number of instances of nucleic acid molecules having the same start and stop points (not including adapter sequences or the like common to the nucleic acid molecules in the same sample) in an individual aliquot relative to the sample before partitioning. Preferably the number of instances of nucleic acid molecules having the same start and stop points is reduced such that at least 75%, 80%, 90%, 95% or 99% of nucleic acid molecules in each aliquot have unique start and stop sequences. In other words, no more than 25%, 20%, 10%, 5% or 1% of nucleic acid molecules in each aliquot share start and stop points with any other nucleic acid molecule in the aliquot. Preferably the number of instances of nucleic acid molecules having the same start and stop points is reduced such that at least 99% of nucleic acid molecules in each aliquot have unique start and stop sequences. In other words, no more than 1% of nucleic acid molecules in each aliquot share start and stop points with any other nucleic acid molecule in the aliquot.

As an alternative to partitioning pooled samples, portions of each of the samples can be pooled for each desired partition aliquot. The portion of each sample pooled should be the same or less than the reciprocal of the desired number of partitions, and the number of poolings should be the same as the desired number of partitions. For example, if 10 samples are pooled and the pooled sample partitioned into 100 aliquots, a functional equivalent result can be obtained by taking 1/100 portion of each of the 10 samples 100 times to form 100 aliquots, each containing 1/100 of each of the initial samples. Partitioning can include adding a fixed amount of nucleic acid molecules from the samples. The fixed amount can be within a range, such as +/−10% of a fixed value, +/−5% of a fixed value or +/−1% of a fixed value. In some embodiments, an aliquot comprises nucleic acid molecules from a subset of the plurality of samples.

There are numerous advantages associated with the partitioning of nucleic acid molecules into a plurality of aliquots realizable either when the partitioned nucleic acids are from the same sample or are a mixture of nucleic acids from different samples. As described above, partitioning reduces the number of instances of nucleic acid molecules having the same start and stop points because only a subset of nucleic acids from a sample is included in a partition. In instances wherein partitions comprise nucleic acid molecules that share the same start and stop positions, but derive from different samples, the nucleic acid molecules can be distinguished by virtue of the sample-specific indexes, which will be different for these different nucleic acid molecules. Accordingly, despite sharing the same start and stop positions, these nucleic acids, and their derivatives, can still be distinguished from each other and the corresponding sequence reads can be grouped into separate families accordingly. The disclosed partitioning approach therefore allows for the identification of sequencing reads deriving from the same nucleic acid in the original sample, while minimizing the number of aliquots that are processed, for example, as compared to methods wherein each sample is partitioned into distinct aliquots that do not comprise sample-indexed nucleic acids from other samples. Compared to such methods, the disclosed methods reduce costs and simplify workflows, due to the reduced number of aliquots that need to be processed in parallel.

The number of partitions depends on the characteristics a population of nucleic acid molecules to be partitioned. These characteristics include the mean, median and mode of nucleic acid molecules having the same start and stop points, the maximum number of instances of nucleic acid molecules having the same start and stop points, and the overall distribution of instances of nucleic acid molecules having the same start and stop points. For example, some nucleic acid populations have a tailed distribution in which most nucleic acid molecules have unique start and stop sequences, a smaller number of molecules have two instances of the same start and stop sequences, a smaller number still have three instances of the same start and stop sequences, and so forth with the number of nucleic acid molecules decreasing as the number of instances of the same start and stop sequences increases. Other nucleic acid populations can have such a tailed distribution but with spikes in which one or a few pairs of start and stop points are represented by many instances of nucleic acids not in conformance with the tailed distribution. For example, a population of cell-free DNA of 25 ng can be characterized by having a ratio of about 0.6 of unique start and stop points to total number of nucleic acid molecules, with most start and stop points with collisions having between 2 and 10 instances of nucleic acid molecules with the same start and stop points and a very small percentage having several hundred instances of nucleic acid molecules with the same start and stop points. Some cell-free nucleic acid populations are characterized by a mean number of nucleic acid molecules with the same start and stop points of 1.5-3 and a maximum number of nucleic acid molecules with the same start and stop points of 100-1000.

FIG. 1 shows an exemplary relationship (for cell-free DNA) between the ratio of unique stop and start points to total number of nucleic acid molecules with increasing coverage (in molecules). For example, at a coverage of 1000 molecules (corresponding to a sample comprising 1000 haploid human genome equivalents or ca. 3 ng of cell-free DNA), the ratio is around 0.85; thus, a surprisingly low number of only around 15% of molecules will 'collide' with another molecule having the same start/stop points. As the average number of nucleic acid molecules aligned to a base position in a reference increase, the ratio of unique start and stop points to total nucleic acid molecules decreases asymptotically. Conversely, as the average number of nucleic acid molecules aligned to a base position in a reference decreases (for example because a sample is partitioned into a plurality of aliquots or using 'virtual' partitions as described elsewhere herein), the ratio rapidly increases towards 1. For example, a typical sample of cell-free DNA of 25 ng (~8000 haploid human genome equivalents) has a ratio of just over 0.6 according to FIG. 1, i.e. around 40% of molecules collide with another molecule. If partitioned into 4 partitions, the ratio would be expected to fall to just under 0.8 i.e. around 20% of molecules collide with another molecule in the same partition; if partitioned into 8 partitions the ratio would be expected to fall to around 0.85 i.e. around 15% of molecules collide with another molecule in the same partition; and if partitioned into 16 partitions the ratio would be expected to fall to around 0.9 i.e. only around 10% of molecules collide with another molecule in the same partition. The desired number of partitions can depend on various factors, such as in particular analyte characteristics, sample input amount, desired levels of sensitivity, and intended application (as described elsewhere herein).

The number of instances of the same start and stop points of nucleic acid molecules in a sample can be determined by molecular counting, among other methods (see e.g. FIG. 1). That is, sample nucleic acid molecules are contacted with molecular barcodes that randomly assort to the sample nucleic acids molecules. The sample nucleic acids and linked molecular barcodes are then amplified and sequenced. The number of sample molecules having the same start and stop points can then be counted from the number of different indexes attached to sequencing reads of nucleic acid molecules with the same start and end points. Characterization of a nucleic acid population can be historical based on similar sample(s) in which case the numbers for previous samples serves as estimates for the current samples, or contemporaneous based on counting nucleic acid molecules in the sample(s) now being sequenced.

For it to be statistically probable that an aliquot contains no instances of multiple nucleic acid molecules with the same start and stop points then the number of partitions should be equal to or greater (e.g., at least 1×, 2×, 5× or 10×) than the maximum number of instances of the same start and stop points in the sample before partition. However, it is not essential that no start and stop points are represented in multiple instances in an aliquot after partitioning. If an aliquot contains two or more instances of molecules with the same start and stop points, then sequencing reads of amplicons from independent original molecules with the same start and stop points may end up being grouped in the same family. This may result in a genuine genetic variation being missed in this family because the variation is present in too few members of the family to be recognized as genuine variation above a background of amplification and sequencing errors. However, because of redundancy in sequencing coverage, the same genetic variation may be detected in other families. For example, in a sample comprising 8000 haploid human genome equivalents, a genetic variation at a mutant allele frequency of 0.1% might be present in 8 original molecules and thus detected in multiple families of sequencing reads even after accounting for some losses due to collisions. Thus, it is sufficient that after partition, a high proportion (e.g., at least 75, 80, 85, 90, 95 or 99%, preferably at least 99%) of nucleic acid molecules in aliquots have unique start and stop points. Such can typically be achieved by partitioning a pooled sample into at least 2, 5, 10, 25, 50, 100, 500, 1000, or 1500 aliquots, for example at least 100 aliquots. Sometimes a pooled sample is partitioned into no more than 2, 3, 4, 5, 6, 8, 10, 12, 16, 100, 500, 1000, 1500 or 5000 aliquots, for example, no more than 1000 or 16 aliquots. A pooled sample can be partitioned into any combination of these lower and upper limits. Sometimes a pooled sample is partitioned into 2-1500, 20-1000, 25-500, 25-100 or 50-400 aliquots, optionally 25-500 aliquots, 2-6, aliquots, 2-8 aliquots, 4-8 aliquots or 4-16 aliquots. The number of partitions can also be determined relative to the mean, median or mode of the number of instances of nucleic acid molecules with the same start and stop points in a population. For example, the number of partitions can be at least 1×, 2×, 5× or 10× the mean, median or mode of the number of instances of nucleic acid molecules with the same start and stop points.

The mean number of molecules of the same start and/or stop points can be estimated, for example, by taking into account the estimated number of nucleic acid molecules in the sample (e.g. the number of genome equivalents) and the estimated diversity of nucleic acids in the sample. The diversity of nucleic acids in the sample may include factors such as the expected variability in the length of nucleic acids, the expected variability in the start points of nucleic acids, the expected variability in the stop points of nucleic acids, and/or the expected variability in the sequence of nucleic acids.

Alternatively, the number of partitions can be determined from an estimated number of nucleic acid molecules of the same length in a sample. The number of partitions should be at least 1×, 2×, 5× or 10× the estimated mean, mode or maximum number of nucleic acid molecules of the same length, optionally at least 5× the estimated mean, mode or maximum number of nucleic acid molecules of the same length. If partitioning is based on the number of nucleic acid molecules of the same length, then sequencing reads are subsequently grouped into families based on having the same length of the sequencing read corresponding to a nucleic acid molecule.

The number of partitions can also be used to control the DNA content of the aliquots so that it is within a desired range for subsequent processing steps. The number of nucleic acid molecules in each partition may be at least 100 nucleic acid molecules, at least 1,000 nucleic acid molecules, at least 10,000 nucleic acid molecules, at least 100,000 nucleic acid molecules, at least 1,000,000 nucleic acid molecules, at least 10,000,000 nucleic acid molecules, at least 100,000,000 nucleic acid molecules, or at least 1,000,000,000 nucleic acid molecules. In some embodiments, the number of nucleic acid molecules in each partition is at least 10,000 nucleic acid molecules.

After partitioning, various processing steps can be conducted in the separate aliquots, including amplification, e.g., with primers complementary to adapter sequences flanking sample molecules, enrichment and differential conversion of unmethylated and methylated bases, particularly cytosine.

With or without such processing steps in separated partitions, the partitioned nucleic acid molecules can be labelled with partition indexes, such that nucleic acid molecules in the same aliquot receive the same partition index and nucleic acid molecules in at least some, and sometimes all of the different aliquots receive different partition indexes. Thus, linkage of sample molecules to partition indexes does not require random assortment of the partition indexes to the sample molecules. In some embodiments, a set of partition indexes with different sequences may be used in each of one or more of the aliquots. In some embodiments, a set of partition indexes with different sequences may be used in each of all of the aliquots. For example, nucleic acid molecules in an aliquot may be labelled with a set of partition indexes with 2-20 different sequences. The sequence of each of the partition indexes in each aliquot can be specific for that aliquot. For example, 2-20 aliquots can be labelled with a set of partition indices having, respectively, 2-20 different sequences, each aliquot receiving a different sequence. Partition indexes can be linked to sample molecules as primer components or by ligation, e.g., as a component of a further adapter. Preferably a partition indexes is included in one or both members of a pair of primers suitable for amplification of nucleic acid molecules in an aliquot. For example, such a primer pair can have 3' regions complementary to adapter sequences flanking sample nucleic acid molecules, with one or both of the primers having a 5' tail region including a partition index. If partition indexes are included in both members of a primer pair, the partition indexes can be the same or different from each other. Having the partition indexes the same provides a measure of redundancy and thus a check on the accuracy of sequencing of the partition index. Having different partition indexes provides a combinatorial increase in the number of available partition indexes. After hybridization of such primers to adapter sequences, an amplification can conducted thereby covalently attaching partition indexes to sample nucleic acids.

After incorporation of partition indexes, further processing steps can be conducted on the aliquots separately or aliquots differentially labelled with partition indexes can be pooled and further processing steps performed on the pooled aliquots. Alternatively, the methods can be performed without use of partition indexes, in which case, all further processing steps are performed on separate aliquots so that it is known which sequencing reads originate from which aliquots. The methods can also be performed with some aliquots pooled and some kept separate from one another. The methods can also be performed with aliquots grouped in subpools, in which the aliquots within a subpool have different partition indexes from one another but aliquots in different subpools can have the same partition indexes as any of the other subpools. The different subpools are then kept separate from one another in subsequent processing whereas the aliquots within a subpooled are processed together. Sequencing reads can be traced back to the aliquot of origin based on a combination of the partition index present in a sequencing read and knowledge of the subpool from which it originated. For example, a sample (e.g. a pooled sample) partitioned into 100 aliquots can be labelled with 10 different partition indexes so that ten aliquots receive each of the 10 different partition indexes. The aliquots can then be grouped into ten subpools of ten aliquots each, the aliquots within a subpool having different partition indexes from one another, and each subpool having ten aliquots with the same ten different partition indexes. Subpools can alternatively be labelled with different sets of partition indexes from one another.

Further processing steps can include further amplification, affinity-enrichment for DNA molecules from selected genomic regions, sequencing and analysis of sequence reads. When partition indexes are used, sequencing is preferably performed after pooling of aliquots into a single vessel. Thus, nucleic acid molecules from the previously separate aliquots and different samples are sequenced together. When partition indexes are not used, sequencing is preferably performed keeping nucleic acid molecules from the different aliquots separate. Optionally, the separate aliquots can be sequenced on different sequencing machines, in different flow cells or different regions or lanes of the same flow cell.

Grouping of sequencing reads by their molecule of origin permits distinction of genuine genetic variation from amplification and sequencing errors as further described below. Moreover, grouping can also be used to address amplification biases in counting-based applications, such as determining copy number variation. In more detail, amplification biases can result in different genomic regions being under or over-represented in sequencing reads depending on the efficiency of amplification of nucleic acids from that genomic region. Such biases can be addressed by quantifying the number of groups rather than the number of sequencing reads.

As described elsewhere herein, grouping may be performed based on the sample index in combination with the start and stop points and/or the length of the sequencing reads. In methods which employ methylation-sensitive conversion, the methylation information contained within the sequencing read can be used to group the sequencing reads in combination with the sample index and optionally the start and stop points and/or the length of the sequencing reads.

III. Sample and Partition Indexes and Adapters

An index is a short nucleic acid (e.g., less than 500, 100, 50, 20, 15, 10 or 5 nucleotides long), used to label nucleic acid molecules, for example to distinguish nucleic acids from different samples (a sample index), or nucleic acid molecules in different aliquots of the sample (partition indexes). The particular code stored by an index can be referred to as a designation of an index. Indexes are typically provided as sets of multiple different individual indexes for distinguishing samples or aliquots of a sample. That is, different samples receive different sample indexes from a set of sample indexes, and different aliquots receive different partition indexes.

In general, the distinction between a set of sample indexes and a set of partition indexes lies in the stages at which they added, the number of different indexes in the set, how the indexes are linked to samples nucleic acids, and the molecules they are used to distinguish rather than in indexes themselves. In principle, a set of sample indexes could be used as a set of partition indexes and vice versa. Preferably the code designations of a set of sample and partition indexes are mutually exclusive with one another.

Indexes can be single-stranded, double-stranded or have both single- and double-stranded components. If a double-stranded component is present, the strands can be of the same or unequal lengths. Indexes can be components of adapters or primers. Sample indexes can be linked to nucleic acid molecules through adapter ligation followed by adapter-targeted primers comprising sample indexes. Sample indexes can be linked to nucleic acid molecules through target specific primers comprising sample indexes in an inverse PCR reaction. Preferably sample indexes are components of adapters and partition indexes are components of primers. Some sets of indexes having sequences selected such that there is a Hamming distance of at least 2, 3, 4 or 5 nucleotides between each index in a set. In some embodiments, the method may comprise grouping sequence reads having the same or similar sample indexes when the sequences of the indexes are selected such that the Hamming distance enables identification of the reads having the same or similar sample indexes as deriving from the same sample index. Indexes can also be selected to avoid sequences that hybridize within one another or other molecules within a reaction, to avoid sequences subject to sequencing errors, or sequences subject to confusion with sequences of other indexes. Indexes as components of adapters or tails of amplification primers can be attached to one end or both ends of nucleic acids to be labelled.

Sample indexes can be decoded to reveal sample of origin. Sample indexes allow for multiplexing (e.g. pooling and parallel processing) of multiple samples after the indexes have been attached. The number of a different sample indexes within a set is typically sufficient that each different sample is associated with a different sample index. Partition indexes together with start and stop points or sequence length of nucleic acid molecules are used to track nucleic acid molecules in the same aliquot of a sample or combination of samples (optionally in combination with indices for tracking individual molecules as discussed below). They can be decoded to sequencing reads of the same original molecule in an aliquot. Partition indices can also be sample-specific, such that embodiments using sample-specific partition indices can be multiplexed after labelling with partition indices, e.g. by pooling, parallel processing (in particular enrichment), and sequencing, without the need for separate sample indices. The methods can also be performed without either sample or partition indexes if each of the partitions from each sample are processed and sequenced separately.

Adapters are relatively short nucleic acids for attachment to the ends of sample molecules to facilitate amplification, sequencing and tracking of the sample molecules. The total length of each adapter (measured by the longest strand if more than one) is e.g., less than 250, 150, 100, 75 or 50 nucleotides long. The free end of the double-stranded portion serves for joining of a sample molecule (e.g., by blunt or cohesive end ligation). Adapters can include the sample indexes discussed above. Adapters can include primer binding sites to permit binding of amplification primers for amplification of a nucleic acid molecule flanked by adapters at both ends, and/or sequencing primers for generating a sequence read. Adapters can also include binding sites for capture probes, such as an oligonucleotide attached to a flow cell support.

Some adapters have one or more double-stranded portions and one or more single-stranded portions. Y-shaped adapters (see, e.g., U.S. Pat. No. 7,741,463), stem-loop (see e.g., U.S. Pat. No. 10,155,939) and bubble adapters (see US20180030532A1) are examples of such adapters. Y-shaped adapters are nucleic acids formed from two strands, which are paired in a double-stranded portion (with the possible exception of a single-stranded overhang to facilitate ligation), and also unpaired in single-stranded portions. The two single-stranded portions can be represented in the shape of the letter V joined to the double-stranded portion, together forming a Y-shape. Y-shaped adapters have one free end in the double-stranded portion, which can be a blunt end or an end in which one strand overhangs the other, e.g., by a single nucleotide. Each of the unpaired single strands has a single-stranded end. The total length of each strand of Y-shaped adapters is e.g., less than 250, 150, 100, 75 or 50 nucleotides long. A standard Illumina Y-shaped adapter without sample or molecular barcodes has a strand length of about 115 nucleotides. The free end of the double-stranded portion serves for joining of a sample molecule (e.g., by blunt or cohesive end ligation).

Stem-loop adapters (e.g., NebNext® from New England Biolabs) are similar to Y-shaped adapters except that the single-stranded portions are joined via a uracil residue thus forming a loop instead of a V. Thus, stem-loop adapters are a single strand with a duplexed stem corresponding to the double-stranded portion of Y-shaped adapters, and a loop including two single-stranded portions of DNA separated by a uracil (U) or deoxyuridine (dU), which correspond to the single-stranded portions of Y-shaped adapters. The residues immediately adjacent the U or dU are the single-stranded-end residues of the single-stranded portions in stem-loop adapters. The stem has a free end that can be blunt or tailed as in the stem of Y-shaped adapters and is used for joining to a sample molecule. After joining of stem-loop adapters to a sample molecule, the U or dU can be enzymatically removed leaving the same topography as for Y-shaped adapters. USER Enzyme from NEB is a mixture of Uracil DNA glycosylase (UDG) and the DNA glycosylase-lyase Endonuclease VIII (DGLE). UDG catalyzes the excision of a uracil or deoxyuridine base, forming an abasic (apyrimidinic) site while leaving the phosphodiester backbone intact, and DGLE removes the abasic nucleotide.

Bubble adapters (BGI) are similar to stem-loop adapters and Y-shaped adapters except that the V-region of Y-shaped adapter or the loop of stem-loop adapters is replaced by a bubble of two unduplexed single stranded portions flanked on both sides by double-stranded portions. Bubble adapters typically have two strands of unequal length with some or all of the length difference being in the single-stranded portions. The 5' end of the longer nucleic acid has a phosphorylated nucleotide. The 3' end of the shorter nucleic acid typically has an overhang from the end of an otherwise double-stranded portion. The double-stranded portion containing the phosphorylated 5' nucleotide and overhang if present corresponds with the stem of stem-loop adapters or the double-stranded portion of Y-shaped adapters and ligates with a sample nucleic acid molecule. This double-stranded portion can be referred to as the downstream double-stranded portion because it provides the site of ligation to a sample molecule. The other double-stranded portion can be referred to an upstream double-stranded portion because it is further from the sample molecule. The two single-strands in the middle forming a bubble correspond with the single-stranded portions forming a V in Y-shaped adapters or the single-stranded portions separated by a uracil or deoxyuridine in stem-loop adapters. Bubble adapters can include a U or dU in the shorter strand, longer strand or both to separate the single-stranded portions from the upstream double-stranded portion. Usually such a U or dU is included in the longer strand. The U or dU can be excised as with stem-loop adapters after ligation of the adapters to sample molecules leaving adapters in a Y-shape.

Adapters can include indexes, particularly sample indexes. Adapters can include primer binding sites to permit binding of amplification primers for amplification of a nucleic acid molecule flanked by adapters at both ends, and/or sequencing primers for generating a sequence read. Primer binding sites are typically provided in the single-stranded portions of a Y-shaped, stem-loop or bubble adapter. The asymmetry of unpaired single-stranded portions allows strand-specific sequencing from two primers binding to the respective single strands. Adapters can also include binding sites for capture probes, such as an oligonucleotide attached to a flow cell support.

The sample indexes may be linked to nucleic acid molecules through the ligation of adapters comprising sample indexes. The adapters may comprise bubble sequences. Bubble sequences are regions of a double stranded adapter that include two single-stranded, non-complementary sequences that do not anneal completely. Such sequences can be used to determine which strand of a double-stranded nucleic acid a sequence read is derived from. The bubble adapters can comprise a sample index and a universal amplification sequence. The universal amplification sequence can be targeted by a universal primer in an amplification step. The universal amplification sequence can be positioned in the adapter such that the amplification products comprise the strand identifier from the bubble sequence and the sample index. The universal primer can comprise a cleavable sequence, such as a uracil containing primer. After universal amplification, the cleavable sequence which has been incorporated into the amplicon can be cleaved. For example, when the cleavable sequence is uracil, a uracil-specific excision reagent can be used (e.g. NEBs' USER Enzyme kit). Alternatively, the universal primers may comprise restriction enzyme recognition sites which can subsequently be cleaved using the corresponding restriction enzyme. After cleavage of the cleavable sequence, the nucleic acids can undergo DNA-end repair and optionally A-tailing. After DNA-end repair and optional A-tailing, further adapters can be ligated to the nucleic acids. Such adapters can comprise sequences which make the nucleic acids amenable to sequencing, such as binding sites for sequencing primers. The further adapters may also comprise a partition index, as disclosed herein. The further adapters may be Y-shaped adapters. The ligation of the further adapters can occur before or after an optional hybrid capture step. Upon sequencing, the sequence reads may be grouped into families or sub-families deriving from the same strand of a nucleic acid molecule in the sample through the use of sequences deriving from the bubble sequence. Such methods are particularly useful in sequencing platforms which use asymmetric adapter ligation (i.e. A-B adapter ligation wherein adapters of different sequences are ligated to each end of a nucleic acid molecule). Such platforms include, for example, sequencing platforms from Ultima Genomics.

IV. Sample Nucleic Acids

Samples can be obtained from different subjects, or the same subject at different times or from different sources (i.e., tissues or fluids) in the same subject. The samples undergo separate preparation and processing at least up to the point at which sample indexes are attached.

A different set of adapters is typically used for different nucleic acid samples. Typically, the different sets differ only in the sample indexes from one another.

After ligation of sample molecules to adapters including sample indexes, the samples can be pooled and processed together with eventual deconvolution of sequencing reads to their sample of origin from the sample indexes. In cases where partition indices are sample-specific, eventual deconvolution of sequencing reads to their sample of origin can be performed using the partition indices.

A sample can be any biological sample isolated from a subject. Samples can include body tissues, such as known or suspected solid tumors, whole blood, platelets, serum, plasma, stool, red blood cells, white blood cells or leucocytes, endothelial cells, tissue biopsies, cerebrospinal fluid synovial fluid, lymphatic fluid, ascites fluid, interstitial or extracellular fluid, the fluid in spaces between cells, including gingival crevicular fluid, bone marrow, pleural effusions, cerebrospinal fluid, saliva, mucous, sputum, semen, sweat, urine. Samples are preferably body fluids, particularly blood and fractions thereof, and urine. A sample can be in the form originally isolated from a subject or can have been subjected to further processing to remove or add components, such as cells, or enrich for one component relative to another. Thus, a preferred body fluid for analysis is plasma or serum containing cell-free nucleic acids.

The number of different samples can be greater than or equal to 2, 5, 10, 50, 100, 500, 1000, 2000, 5000, or 10,000. The volume of plasma can depend on the desired read depth for sequenced regions. Exemplary volumes are 0.4-40 mL, 5-20 mL, 10-20 mL. For examples, the volume can be 0.5 mL, 1 mL, 5 mL 10 mL, 20 mL, 30 mL, or 40 mL. A volume of sampled plasma may be for example 5 to 20 mL.

In some embodiments, the plurality of samples comprises samples (e.g. cell-free DNA samples) obtained from different subjects, for example, different subjects suspected of having cancer. In some embodiments, the plurality of samples comprises samples obtained from at least 5, at least 10, at least 25, at least 50, at least 100, or at least 500 different subjects. In some embodiments, the plurality of samples comprises samples obtained from the same subject, but at different time points. In some embodiments, the different time points are at least a week apart, at least a month apart, or at least a year apart. In some embodiments, samples from the same subject taken at different time points may be used to monitor disease progression, evaluate therapeutic response, detect recurrence, or identify changes in biomarker profiles over time. In some embodiments, the plurality of samples comprises samples obtained from the same subject before, during, and/or after a therapeutic intervention.

A sample can comprise various amount of nucleic acid that contains genome equivalents. For example, a sample of about 30 ng DNA can contain about 10,000 haploid human genome equivalents and, in the case of cell-free DNA, about 200 billion individual nucleic acid molecules. Similarly, a sample of about 100 ng of DNA can contain about 30,000 haploid human genome equivalents and, in the case of cell-free DNA, about 600 billion individual molecules. Some samples contain 1-500, 2-100, 5-150 ng cell-free DNA, e.g., 5-30 ng, 8-25 ng, or 10-150 ng cell-free DNA. The nucleic acids can be free in solution in the sample prior to the partitioning.

The most preferred analyte of the methods of the invention is cell-free DNA. cfDNA has a peak of fragments at about 160 nucleotides (e.g., 168 nucleotides), and most of the fragments in this peak range from about 140 nucleotides to 180 nucleotides. Accordingly, cfDNA from a genome of about 3 billion bases (e.g., the human genome) may be comprised of almost 20 million ($2\times10^7$) polynucleotide fragments. A sample of about 30 ng DNA can contain about 10,000 haploid human genome equivalents. (Similarly, a sample of about 100 ng of DNA can contain about 30,000 haploid human genome equivalents.) A sample containing about 10,000 ($10^4$) haploid genome equivalents of such DNA can have about 200 billion ($2\times10^{11}$) individual polynucleotide molecules.

A sample can comprise nucleic acids of different types and origins. A sample can contain DNA or RNA or both. Nucleic acids can be single-stranded or double-stranded or be partly double-stranded and partly single-stranded. A sample can comprise germline DNA or somatic DNA or both. Nucleic acids within a sample can carry genetic variations, which can be carrying germline mutations and/or somatic mutations. Some such mutations can be cancer markers (e.g., cancer-associated somatic mutations).

Exemplary amounts of cell-free nucleic acids in a sample before amplification range from about 1 fg to about 1 ug, e.g., 1 pg to 200 ng, 1 ng to 100 ng, 10 ng to 1000 ng. For example, the amount can be up to about 600 ng, up to about 500 ng, up to about 400 ng, up to about 300 ng, up to about 200 ng, up to about 100 ng, up to about 50 ng, or up to about 20 ng of cell-free nucleic acid molecules. The amount can be at least 1 fg, at least 10 fg, at least 100 fg, at least 1 pg, at least 10 pg, at least 100 pg, at least 1 ng, at least 10 ng, at least 100 ng, at least 150 ng, or at least 200 ng of cell-free nucleic acid molecules. The amount can be up to 1 femtogram (fg), 10 fg, 100 fg, 1 picogram (pg), 10 pg, 100 pg, 1 ng, 10 ng, 100 ng, 150 ng, or 200 ng of cell-free nucleic acid molecules. The method can comprise obtaining 1 femtogram (fg) to 200 ng.

An exemplary sample is 5-10 ml of whole blood, plasma or serum, which includes about 30 ng of DNA or about 10,000 haploid genome equivalents.

Some samples contain cell-free nucleic acids. Cell-free nucleic acids are nucleic acids not contained within or otherwise bound to a cell or in other words nucleic acids remaining in a sample after removing intact cells. Cell-free nucleic acids include DNA, RNA, and hybrids thereof, including genomic DNA, mitochondrial DNA, siRNA, miRNA, circulating RNA (cRNA), RNA, rRNA, small nucleolar RNA (snoRNA), Piwi-interacting RNA (piRNA), long non-coding RNA (long ncRNA), or fragments of any of these. Cell-free nucleic acids can be double-stranded, single-stranded, or a hybrid thereof. Double-stranded DNA molecules at least some of which have single-stranded overhangs are a preferred form of cell-free DNA for any method disclosed herein. A cell-free nucleic acid can be released into bodily fluid through secretion or cell death processes, e.g., cellular necrosis and apoptosis. Some cell-free nucleic acids are released into bodily fluid from cancer cells e.g., circulating tumor DNA, (ctDNA). Others are released from healthy cells.

A cell-free nucleic acid can have one or more epigenetic modifications, for example, a cell-free nucleic acid can be acetylated, methylated, ubiquitinylated, phosphorylated, sumoylated, ribosylated, and/or citrullinated.

Cell-free nucleic acids have a size distribution of about 100-500 nucleotides, particularly 110 to about 230 nucleotides, with a mode of about 168 nucleotides and a second minor peak in a range between 240 to 440 nucleotides.

Cell-free nucleic acids can be isolated from bodily fluids through a purification step in which cell-free nucleic acids, as found in solution, are separated from intact cells and other non-soluble components of the bodily fluid. Such purification may include techniques such as centrifugation or filtration. Alternatively, cells in bodily fluids can be lysed and cell-free and cellular nucleic acids processed together. Generally, after addition of buffers and wash steps, nucleic acids can be precipitated with an alcohol. Further clean up steps may be used such as silica-based columns to remove contaminants or salts. Non-specific bulk carrier nucleic acids, for example, may be added throughout the reaction to optimize certain aspects of the procedure such as yield.

After such processing, samples can include various forms of nucleic acid including double-stranded DNA, single-stranded DNA and single-stranded RNA. Optionally, single-stranded DNA and RNA can be converted to double-stranded forms so they are included in subsequent processing and analysis steps.

Nucleic acid present in a sample with or without prior processing as described above typically contain a substantial portion of molecules in the form of partially double-stranded molecules with single-stranded overhangs. Such molecules can be converted to blunt-ended double-stranded molecules by treating with one or more enzymes to provide a 5'-3' polymerase and a 3'-5' exonuclease (or proof-reading function), in the presence of all four standard nucleotide types. Such a combination of activities can extend strands with a recessed 3' end so they end flush with the 5' end of the opposing strand (in other words generating a blunt end) or can digest strands with 3' overhangs so they are likewise flush with the 5' end of the opposing strand. Both activities can optionally be conferred by a single polymerase. The polymerase is preferably heat-sensitive so that its activity can be terminated when the temperature is raised. Klenow large fragment and T4 polymerase are examples of suitable polymerase.

The resulting blunt-ended nucleic acids can be ligated to adapters with a double-stranded blunt free end or can be subject to tailing to generate cohesive ends, which pair with corresponding single-stranded overhangs at a double-stranded free end of adapters. Tailing of blunt ends can be by a polymerase lacking a proof-reading function. This polymerase can be thermostabile such as to remain active at the elevated temperature that denatures the polymerase use for blunt ending. Taq, Bst large fragment and Tth polymerases are examples of such a polymerase. The second polymerase effects a non-templated addition of a single nucleotide to the 3' ends of blunt-ended nucleic acids. Although the reaction mixture typically contains equal molar amounts of each of the four standard nucleotide types from the prior step, the four nucleotide types are not added to the 3' ends in equal proportions. Rather A is added most frequently, followed by G followed by C and T. Such tailed molecules can be ligated to adapters with a complementary T or C overhand at the free end of the double-stranded portion.

Preferably, the present methods result in at least 50, 60, 75, 80, 85, 90 or 95% of double-stranded nucleic acids in the sample being linked to at both of their ends to adapters. Preferably, the present methods result in at least 50, 60, 75, 80, 85, 90 or 95% of available double-stranded molecules in the sample being sequenced.

V. Amplification

Sample nucleic acids flanked by adapters can be amplified by PCR and other amplification methods typically primed from primers binding to primer binding sites in adapters flanking a nucleic acid to be amplified. Primer binding sites can be positioned in the adapter such that the amplification products include any sample indexes and/or partition indexes present in the adapter. Primers can include a 3' target or adapter binding region, which binds to a complementary sequence on a target or adapter, and a 5' tail region. The tail region can include an index, particularly a partition indexes as described above. Amplification methods can involve cycles of extension, denaturation and annealing resulting from thermocycling or can be isothermal as in transcription mediated amplification. Other amplification methods include the ligase chain reaction, strand displacement amplification, nucleic acid sequence-based amplification, and self-sustained sequence-based replication. Amplification can be performed once or multiple times. Amplification can be performed before and distinct from sequencing or integrated with sequencing or both. Amplification can also be performed before or after enrichment of selected sample molecules, or both.

VI. Enrichment

Sample molecules can be subject to enrichment for sequences of interest. Enrichment can be performed by affinity purification, e.g., by hybridization to immobilize oligonucleotides complementary to the sequences of interest. Enrichment can be performed before or after ligation to adapters, and before or after amplification, or any combination thereof. If enrichment is performed before attachment of sample indexes, the samples are enriched separately, whereas if enrichment is performed after attachment of sample indexes it can be performed on pooled samples. If portions of sample molecules are subject to base conversion e.g., unmethylated C to T, before enrichment, then probes used for enrichment are modified to be complementary to sequences including the complement of the modified base (e.g., A in place of G to hybridize to T instead of G). The probes used for enrichment may include probes specific for a specific methylation state of the target nucleic acid. The probes used for enrichment may include a mixture of probes which are each specific for a different methylation state of the target nucleic acid.

In some embodiments, the probes specific for the target regions comprise a capture moiety that facilitates the enrichment or capture of the nucleic acids hybridized to the probes. In some embodiments, the capture moiety is biotin. In some such embodiments, streptavidin attached to a solid support, such as magnetic beads, is used to bind to the biotin. Nonspecifically bound nucleic acids that do not comprise a target region are washed away from the captured nucleic acids. In some embodiments, the nucleic acid is then dissociated from the probes and eluted from the solid support using salt washes or buffers comprising another nucleic acid denaturing agent. In some embodiments, the probes are also eluted from the solid support by, e.g., disrupting the biotin-streptavidin interaction. In some embodiments, captured nucleic acid is amplified following elution from the solid support. Target-specific oligonucleotide probes for use in hybrid capture can be biotinylated RNA probes.

A collection of target-specific oligonucleotide probes for use in hybrid capture can comprise probes specific for a sequence-variable target region set and/or probes specific for an epigenetic target region set. Probes for the sequence-variable target region set can comprise probes specific for a plurality of regions known or suspected to undergo somatic mutations in cancer, in particular somatic SNVs or indels. Probes for the epigenetic target region set can comprise probes specific for a plurality of regions known or suspected to show hypermethylation or hypomethylation in cancer (or other epigenetic changes).

Enrichment via hybrid capture produces a captured set of (cell-free) DNA molecules. The (cell-free) DNA molecules corresponding to the sequence-variable target region set can be captured at a greater capture yield than (cell-free) DNA molecules corresponding to the epigenetic target region set, and subsequently be sequenced at a greater sequencing depth. The collection of probes can be configured to provide higher capture yields for the sequence-variable target region set in various ways, including concentration, different lengths and/or chemistries (e.g., nucleotide modifications that affect affinity, such as locked nucleic acids (LNA)). For example, higher concentration and/or longer sequence lengths can increase affinity.

Although focal amplifications are somatic mutations, they can be detected by sequencing based on read frequency in a manner analogous to approaches for detecting certain epigenetic changes such as changes in methylation. As such, probes specific for a focal amplification-variable target region set (e.g. comprising probes specific for a plurality of regions known or suspected to show focal amplification in cancer) can be included alongside the epigenetic target region set. Such regions may comprise one or more of AR, BRAF, CCND1, CCND2, CCNE1, CDK4, CDK6, EGFR, ERBB2, FGFR1, FGFR2, KIT, KRAS, MET, MYC, PDGFRA, PIK3CA, and RAF1.

The invention provides methods of sequencing in which different aliquots from the same sample are subject to different enrichment reactions. Typically, the different enrichment reactions serve to enrich for different parts of a genome, which can be achieved for example by using different oligonucleotide probes or sets of such probes for affinity enrichment as described above. Multiple samples can be handled in parallel, either maintaining the samples separate, or labelling the samples with sample indexes and pooling.

In such a method, a sample is partitioned in a plurality of aliquots. At least some of the different aliquots then receive different partition indexes from one another. For this purpose, the aliquots can be classified in sets, the members within a set receiving different partition indexes from one another. Different sets of aliquots can receive the same or different sets of partition indexes. For example, if a sample is partitioned into eight aliquots, a set of aliquots 1~4 can each receive one of a set of four partition indexes, and a set of aliquots 5-8 can likewise receive of a set of four partition indexes. The respective sets of partition indexes for aliquots 1~4 and 5-8 can be the same or different from one another. A second sample can likewise be partitioned into sets of aliquots. For example, the second sample can also be partitioned into eight aliquots with a set of aliquots 1~4 receiving one of a set of four partition indexes and a set of aliquots 5-8 receiving one of a set of four partition indexes. The sets of partition indexes used for samples 1 and 2 can be the same or different from each other. Other samples can likewise be partitioned.

Samples can also be partitioned into any other number of aliquots, for example, 2, 4, 6, 8, 10 or 16 aliquots.

The aliquots from the same sample that have received different partition indexes can be pooled for subsequent processing. For each sample, at least two such pools are formed.

If the samples have been separately labelled with sample indexes, or the aliquots of different samples are linked to different (mutually exclusive) sets of partition indexes, then different samples or pools of aliquots from different samples can also be pooled. If the samples are not labelled with sample labels and the same set or sets of partition labels are used for labelling aliquots from different samples, then the pools from different samples are processed separately in subsequent steps.

The pools from the same sample can be subjected to different enrichment reactions. The enriched pools can then be subject to sequencing. If the pools are labelled with the same sets of partition labels, they are sequenced separately. If the enriched pools are labelled with different mutually exclusive sets of partition labels, then they can be pooled before sequencing.

VII. Sequencing

Amplicons of nucleic acid molecules flanked by adapters can be subject to sequencing. Sequencing methods preferably provide sequencing reads of sufficient length to read through sample molecules and partition index sequences on one or both sides of a sample molecule in a single read. For example, a sequencing read can include a sample molecule sequence flanked on each side by a sample index sequence, which are in turn flanked on each side by a partition index sequence. If sample index sequences are present on each side, the sequences are preferably the same as each other with the possible exception of errors introduced during amplification or sequencing. Likewise, partition index sequences on each side are preferably the same as each other except for such errors. Sequencing methods include, for example, Sanger sequencing, high-throughput sequencing, pyrosequencing, sequencing-by-synthesis, single-molecule sequencing, single molecule real time sequencing (Pac-Bio), ONT-sequencing, exon sequencing, electron microscopy-based sequencing, panel sequencing, transistor-mediated sequencing direct sequencing, random shotgun sequencing, whole exome sequencing, whole genome sequencing, capillary electrophoreses, gel electrophoresis, duplex sequencing, cycle sequencing, single-base extension sequencing, emulsion PCR, co-amplification at lower denaturation temperature-PCT (COLD-PCR), sequencing by reversible dye terminator, paired-end sequencing, near-term sequencing, exonuclease sequencing, sequencing by ligation, short-read sequencing, nanopore sequencing, semiconductor sequencing, sequencing-by-ligation, sequencing-by-hybridization, RNA-Seq (Illumina), Digital Gene Expression (Helicos), next generation sequencing, single molecule sequencing by synthesis (SMSS) (Helicos), massively-parallel sequencing, 454 sequencing, Clonal Single Molecule Array (Solexa/Illumina), shotgun sequencing, Ion Torrent, Oxford Nanopore, Roche Genia, Maxim-Gilbert sequencing, primer walking, SOLID, Ion Torrent, MS-PET sequencing or Nanopore platforms, and combinations thereof. Sequencing reactions can be performed in a variety of sample processing units, which may multiple lanes, multiple channels, multiple wells, or other mean of processing multiple sample sets substantially simultaneously. Sample processing unit can also include multiple sample chambers to enable processing of multiple runs simultaneously.

The sequence reactions may provide for sequence coverage of the genome of at least 5%, 10%, 15%, 20%, 25%, 30%, 40%, 50%, 60%, 70%, 80%, 90%, 95%, 99%, 99.9% or 100%. In other cases, sequence coverage of the genome may be less than 5%, 10%, 15%, 20%, 25%, 30%, 40%, 50%, 60%, 70%, 80%, 90%, 95%, 99%, 99.9% or 100%.

Simultaneous sequencing reactions may be performed using multiplex sequencing. In some cases, amplicons of sample nucleic acids may be sequenced with at least 1000, 2000, 3000, 4000, 5000, 6000, 7000, 8000, 9000, 10000, 50000, 100,000 sequencing reactions. In other cases, amplicons of sample nucleic acids may be sequenced with less than 1000, 2000, 3000, 4000, 5000, 6000, 7000, 8000, 9000, 10000, 50000, 100,000 sequencing reactions. Sequencing reactions may be performed sequentially or simultaneously. Subsequent data analysis may be performed on all or part of the sequencing reactions. In some cases, data analysis may be performed on at least 1000, 2000, 3000, 4000, 5000, 6000, 7000, 8000, 9000, 10000, 50000, 100,000 sequencing reactions. In other cases, data analysis may be performed on less than 1000, 2000, 3000, 4000, 5000, 6000, 7000, 8000, 9000, 10000, 50000, 100,000 sequencing reactions.

The sequencing method can be massively parallel sequencing, that is, simultaneously (or in rapid succession) sequencing any of at least 100, 1000, 10,000, 100,000, 1 million, 10 million, 100 million, or 1 billion nucleic acid molecules. Sequencing may be performed at a read depth of 1000-200,000 or 10,000-100,000 or 30,000-80,000 reads per locus (base). Sequencing may be performed at a read depth at least 30,000, at least 50,000, at least 75,000 or at least 100,000 reads per locus (base). Sequencing may be performed at a read depth at least 50,000 reads per locus (base).

Sequencing can be performed in a single or paired read format with sample and partition indexes at least at the start of a read, and sometimes at the end of a read as well. In some embodiments, a sequencing read is a paired-end sequencing read. The paired-end sequencing read may comprise mate-pairs. The mate-pairs may together comprise the sequence of the nucleic acid molecules and the sample index. The sequence of the nucleic acid molecules and the sample index may be present in the same mate of the mate pair or different mates of the mate-pair. A sequencing read, as referred to herein, may comprise any associated index reads, such as the i5 and i7 indexes. These may be read at the same time or separately to the sequence of the nucleic acid molecule.

VIII. Methylation Analysis

Methylation analysis can involve methylation-based separation of nucleic acid molecules. In some embodiments, methylation-based separation of nucleic acid molecules is performed by contacting the nucleic acid molecules with an agent that recognizes methylated DNA, such as 5-methylcytosine. In particular embodiments, the agent is a methyl binding reagent. In particular embodiments, the methyl binding reagent is a methyl binding domain (MBD) protein or an antibody. In some embodiments, the methyl binding reagent specifically recognizes 5-methylcytosine. For example, methylated fragments in a DNA sample can be separated via methylated DNA immunoprecipitation (MeDIP), or methylated fragments can be separated from unmethylated fragments using methyl binding domain proteins (e.g., MethylMinder Methylated DNA Enrichment Kit (ThermoFisher Scientific).

Methylation analysis can comprise subjecting parent nucleic acids or amplification products thereof to a procedure that affects a first nucleobase in the nucleic acid differently from a second nucleobase, for example wherein the first nucleobase is a modified or unmodified nucleobase, the second nucleobase is a modified or unmodified nucleobase different from the first nucleobase, and the first nucleobase and the second nucleobase have the same base pairing specificity. In some embodiments, the procedure that affects a first nucleobase of the nucleic acid differently from a second nucleobase of the nucleic acid is a methylation-sensitive conversion. In particular embodiments, the methylation-sensitive conversion is bisulfite conversion, oxidative bisulfite (Ox-BS) conversion, Tet-assisted bisulfite (TAB) conversion, APOBEC-coupled epigenetic (ACE) conversion, enzymatic methyl-seq (EM-seq) conversion, single-enzyme 5-methylcytosine sequencing (SEM-seq) conversion, or direct methylation sequencing (DM-seq).

Some embodiments of the disclosed methods further comprise contacting the nucleic acid molecules with at least one nuclease, such as prior to the partitioning, prior to the capturing, or prior to the sequencing. In some embodiments, the at least one nuclease comprises at least one restriction enzyme. In some embodiments, the at least one nuclease comprises at least one methylation-sensitive restriction enzyme (MSRE) and/or at least one methylation-dependent restriction enzyme (MDRE).

Samples can be analyzed for DNA modification (see, e.g., Gouil et al., Essays Biochem. 63 (6): 639-648 (2019)) by treating with an agent that acts differently on methylated than unmethylated bases. For example, bisulfite treatment converts unmethylated C's to U's, while leaving methylated C's unchanged. Optionally samples can be split into at least two portions before treatment with agent, such as bisulfite, with one portion undergoing treatment and the other portions serving as an untreated control. However, even without a control conversion of one base type to another, such as C to U/T can be recognized by comparison of a sequencing read with a reference sequence.

5hmC can also be detected using TET-assisted bisulfite sequencing (TAB-seq). Fragmented DNA is enzymatically modified using sequential T4 Phage β-glucosyltransferase (T4-BGT) and then Ten-eleven translocation (TET) dioxygenase treatments before the addition of sodium bisulfite. T4-BGT glucosylates 5hmC to form beta-glucosyl-5-hydroxymethylcytosine (5ghmC) and TET is then used to oxidize 5mC to 5caC. Only 5ghmC is protected from subsequent deamination by sodium bisulfite and this enables 5hmC to be distinguished from 5mC by sequencing.

Oxidative bisulfite sequencing (oxBS) provides another method to distinguish between 5mC and 5hmC (4). The oxidation reagent potassium perruthenate converts 5hmC to 5-formylcytosine (5fC) and subsequent sodium bisulfite treatment deaminates 5fC to uracil. 5mC remains unchanged and can therefore be identified using this method.

APOBEC-coupled epigenetic sequencing (ACE-seq) excludes bisulfite conversion altogether and relies on enzymatic conversion to detect 5hmC. With this method, T4-BGT glucosylates 5hmC to 5ghmC and protects it from deamination by Apolipoprotein B mRNA editing enzyme subunit 3A (APOBEC3A). Cytosine and 5mC are deaminated by APOBEC3A and sequenced as thymine.

TET-assisted 5-methylcytosine sequencing (TAmC-seq) enriches for 5mC loci and utilizes two sequential enzymatic reactions followed by an affinity pull-down. Fragmented DNA is treated with T4-BGT which protects 5hmC by glucosylation. The enzyme mTET1 is then used to oxidize 5mC to 5hmC, and T4-BGT labels the newly formed 5hmC using a modified glucose moiety (6-N3-glucose). Click chemistry is used to introduce a biotin tag which enables enrichment of 5mC-containing DNA fragments for detection and genome wide profiling.

EM-SEQ detects 5mC and 5hmC using two sets of enzymatic reactions. In the first reaction, TET2 and T4-BGT convert 5mC and 5hmC into products that cannot be deaminated by APOBEC3A. In the second reaction, APOBEC3A deaminates unmodified cytosines by converting them to uracils, which are converted to thymine on amplification. Thus, unmodified C's are detected as T's. Vaisvila et al., Genome Res. 2021 July; 31 (7): 1280-1289. doi: 10.1101/gr.266551.120. Epub 2021 Jun. 17. PMID: 34140313; PMCID: PMC8256858.

Taps for Tet-assisted pyridine borane sequencing is a 5mC and 5hmC detection method that utilizes mild reactions based on ten-eleven translocation (TET) enzyme oxidation of 5mC and 5hmC to 5-carboxylcytosine (5caC) and subsequent pyridine borane reduction of 5caC to dihydrouracil (DHU). During PCR amplification, DHU is recognized as thymine, resulting in a 5mC/5hmC-to-T transition (Liu et al., CS Chem. Biol. 2022, 17, 10, 2683-2685, Publication Date: Oct. 4, 2022).

Comparison of sequencing reads from treated and control groups indicates, which cytosines were subject of modification. Splitting into groups for analysis of DNA modification, such as by bisulfite conversion, is preferably performed after partitioning of combined samples into aliquots so members of the same pairs of duplex strands are present in the same aliquot. Conversion also preferably precedes amplification. Conversion can occur before or after enrichment. If conversion occurs before enrichment, probes must be modified to hybridize with modified bases (e.g., U/T in place of C). Thus, a preferred order of steps is to attach sample indexes to different samples, pool the different samples, partition the pooled samples, conversion of portions of the partitioned samples, amplification, enrichment and sequencing.

Figure 14:
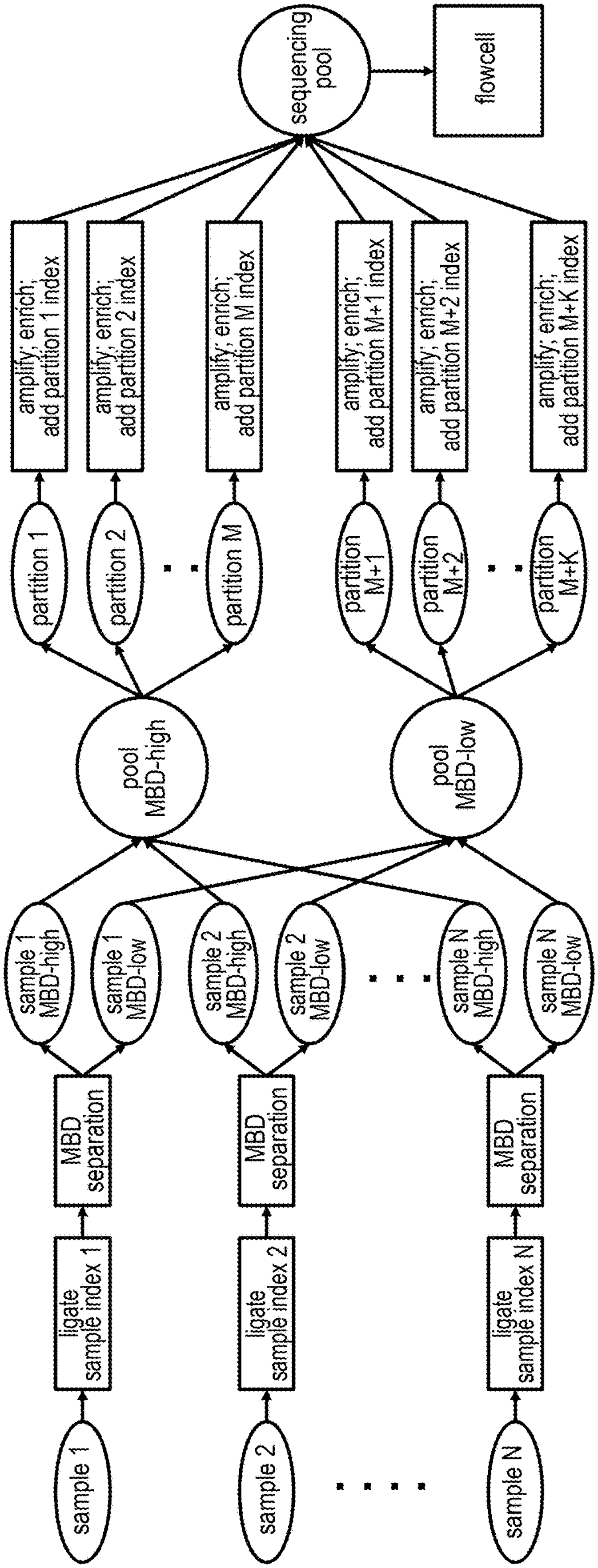

Methylation can also be analyzed by affinity enrichment of methylated DNA with methyl binding domain sequencing (e.g., see WO2018119452). These types of methods separate DNA fragments having a high methyl C content from those with a low methyl C content before sequencing. FIGS. 12-14 provide workflows using a type of methyl binding domain (MBD) separation.

In FIG. 12, MBD separation is performed on individual samples, resulting in two portions for each sample, one having high methyl C content, the other lower methyl C content. The portions are then labelled with sample indexes. The portions are then pooled, high methyl content portions being pooled together, and low methyl content portions being pooled together. The two pools are then partitioned. Amplification and enrichment are performed in the separate partitions followed by attachment of partitions indexes. The partitions are then combined for sequencing. FIG. 13 shows a similar workflow except that after ligation of sample indexes all portions are combined in the same pool instead of splitting into high and low methyl content pools. FIG. 14 shows a similar workflow as FIG. 12 except that samples indexes are attached to samples before MBD separation. Thus, high and low methyl portions after MBD separation have the same sample index and are kept separate by pooling into two pools one with high methyl content, the other low methyl content. The two pools are separately portioned. The partitions are subject to amplification and enrichment followed by incorporation of partition indexes. The partitions are then combined for sequencing.

IX. Analysis and Deconvolution of Indexes

Sequencing of amplicons of sample nucleic acids provides sequencing reads including a segment corresponding to a sample nucleic acid, a (sample) index at one or both ends of the segment corresponding to the sample nucleic acid, and a partition index, if present, at one or both ends. Sequencing reads can be demultiplexed according to their sample of origin by deconvolution of sample indexes or sample-specific partition indices. Such demultiplexing can occur before or after alignment of sequencing reads with a genomic reference sequence. Sequencing reads from the same sample can be segregated by aliquot of origin from the partition index, if present. If partition indexes are not used, sequencing reads can be traced back to the aliquot of origin by keeping the aliquots separate throughout sequencing and prior steps.

Sequencing reads from the same sample can be segregated into families representing amplification copies of the same original molecule from the partition index, if present, or alternatively aliquot of origin, and the sequence of the sample nucleic acid, particularly its start and stop points, or more approximately, its sequence length. Start and stop points are determined by aligning sequencing reads with a known reference sequence, such as a whole genome, or parts thereof known to be enriched for in the nucleic acid molecules being analyzed. Sequencing reads from the same sample with the same aliquot of origin and same start and stop points or same sequence length are grouped into the same family. Grouping sequence reads may also be performed based on a minimum sequence similarity between the sequence reads. For example, the grouping step may comprise grouping sequencing reads having the same sample index into families, wherein sequencing reads in the same family have a minimum sequence similarity relative to other sequence reads in the group, and are from the same aliquot. In such embodiments, the method may not explicitly determine start and stop points and/or lengths of the sequences of the nucleic acid molecules. The minimum sequence similarity may comprise at least 90% sequence identity, at least 95% sequence identity, at least 99% sequence identity or at least 100% sequence identity. The minimum sequence similarity may comprise at least 99% sequence identity. The level of sequence similarity can be determined by global alignment. As used herein, a "global alignment" is an alignment that aligns sequences from beginning to end, aligning each base in each sequence only once. An alignment is produced regardless of whether or not there is similarity or identity between the sequences. For example, 50% sequence identity based on "global alignment" means that in an alignment of the full sequence of compared sequences each of 100 nucleotides in length, 50% of the bases are the same. It is understood that global alignment also can be used in determining sequence identity even when the length of the aligned sequences is not the same. The differences in the terminal ends of the sequences will be taken into account in determining sequence identity. Exemplary algorithms for performing global alignment include the Needleman-Wunsch algorithm (Needleman et al. J. Mol. Biol. 48:443 (1970).

Grouping of sequencing reads into families can be preceded by demultiplexing sequencing reads by sample origin from the sample-specific partition indices or the sample indexes, such that the grouping is performed on sequencing reads having the same sample indexes. The sequencing reads within the same family can include sequencing reads from either or both strands of the same original molecule. In other words, an index sequence and its exact complement are considered the same sequence and start and stop points and their exact complements are considered the same sequence for grouping reads into families.

Grouping sequence reads into families may alternatively be performed without the step of aligning the sequencing reads to a reference sequence. For example, the sequence reads may be aligned to each other, wherein the sequence reads are grouped with each other if they have the same sample index and satisfy an alignment criterion. The alignment criterion may comprise a minimum sequence identity (e.g. fewer than 2 mismatches) and/or the sequence corresponding to the nucleic acid molecules have the same or similar (e.g. within 2 nucleotides) termini.

If a sequencing read includes two sequences of a sample index, which differ from one another as a result of amplification or sequencing error, the error may be resolvable by selecting the index from the initial set with the greatest identity to the two index sequences in the sequencing read. Alternatively, the sequencing read can be discarded as being subject to error. Similar considerations apply if sequencing reads include two sequences of a partition index.

The sequencing reads of family members can be compiled to derive consensus nucleotide(s) at specified positions or consensus sequence at some or all positions of a nucleic acid molecule in the original sample. If members of a family include sequencing reads of opposing strands, sequences of one strand can be converted to their complements for purposes of compiling and aligning all sequencing reads to derive consensus nucleotide(s) or sequences. A consensus nucleotide type at a position can be defined as the nucleotide type most frequently occupying that position among aligned sequencing reads. Likewise, a consensus sequence can be defined as sequence of such consensus nucleotide types. For a nucleotide type to be called as consensus at a particular position in aligned sequencing reads, it can also be required that the nucleotide type occurs above a threshold frequency level among nucleotide types occupying that position in the aligned sequencing reads. For example, it can be required that the nucleotide type be present at that position in at least 50, 60, 70, 80 or 90% of sequencing reads. It can additionally or alternatively be required that the nucleotide type be present in at least one sequencing read of both strands of an original molecule. It can additionally or alternatively be required that the nucleotide type not be contradicted by more than a threshold number of sequencing reads of one or both strands in which the aligned position is occupied by a different nucleotide type. Consensus deletions or insertions can be identified by similar analyses of representation and/or presence in both strands as substitutions.

Some families may include only a single sequencing read. In this case, this sequence can be taken as the sequence of a nucleic acid in the sample before amplification. Alternatively, families with only a single member sequence can be eliminated from subsequent analysis.

The criteria described above for identifying consensus nucleotides or sequence help filter genuine nucleotide variations from a reference sequence in original sample molecules and variations resulting from amplification or sequencing errors. Nucleic acid variations present in original sample molecules are likely to have greater representation in sequencing reads in general and particularly in sequencing reads of both strands than variations resulting from amplification or sequencing errors and thus be designated as consensus nucleotide types or sequences of such nucleotide types.

Having determined consensus nucleotides and/or consensus sequences within individual families, the results can be compiled to provide an indication of what nucleotide variations are present in a sample compared with a known reference sequence. The known reference sequence can be that of a gene, chromosome or genome among others. Such a compilation can provide an additional filter to distinguish genuine sequence variations from amplification and sequencing errors and provide an indication of the representation or allele frequency of such variations relative to wildtype in a sample. For any position of interest in a reference sequence for a sample (e.g., wildtype human genome sequence), one can determine which families have sequencing reads spanning that position. From those families one can determine a representation of variant nucleotide type, deletion or insertions, if any, and wildtype nucleotide type for that position. A variation can be called out as being present at the position if multiple families include the variation, or the number of families including a variant nucleotide type, deletion or insertions exceeds a threshold, or the ratio of families with the variant nucleotide type, deletion or insertion to wildtype exceeds a threshold among other criteria. The ratio of variant nucleotide type, deletion or insertion to wildtype nucleotide type also provides an indication of the representation of the variant nucleotide. Such an analysis can be performed for each nucleotide of interest in a reference sequence corresponding to a particular sample, thus providing a variant profile of that sample. The analysis can be repeated for each sample using families of sequencing reads and their consensus nucleotides or nucleotide sequences derived as discussed above. Thus, each sample can be characterized by a variant nucleotide type profile.

Consensus nucleotides or sequences can also be compared across different sample aliquots subject to treatment resulting in differential substitution of modified and unmodified nucleotides, as in any of the methylation sequencing methods discussed. For example, treatment of DNA with sodium bisulfite converts unmethylated cytosine to uracil, which is subsequently converted to thymine during PCR amplification, while methylcytosine remains unchanged. Such analysis indicates which nucleotides in samples molecules are modified, such as by methylation.

Sequence families can also be used to provide an indication of copy number variation (see, e.g., WO2017/106768, WO/2015/100427). The number of families having a consensus sequencing read spanning a particular locus or within a defined window of a genome compared with the number of families mapping to a locus or window elsewhere in the genome, provides a measure of copy number variation, which can arise from either amplification or loss of an allele. In some embodiments, copy number variation can be determined without generating a consensus sequencing read. Measured numbers of families can be normalized as needed to account for such factors as differences in window size, sequencing coverage or enrichment for different regions of a genome.

X. Levels of Molecular Identification

As set out in the preceding sections, the present methods use a molecular identification scheme wherein sequencing reads are deconvoluted to original molecules (e.g. 'family grouping') by alignment position (such as having the same start and stop points) and the aliquot of origin. The aliquot of origin is tracked by partition indices or separate sequencing (which can be considered 'physical indexing'), or by a combination of both.

FIGS. 15A-D show a protocol according to the invention wherein different aliquots are tracked using aliquot-specific partition indices (Variation #1) or tracked using partition indices and separate sequencing (Variation #2). In both variations, 96 samples are each ligated to a different sample index, and subsequently mixed and aliquoted into 96 wells (FIG. 15A). The particular numbers of samples and partitions are provided as an example. In Variation #1 (FIG. 15B), each well receives a different partition index via PCR with labelled primers (i.e. the partition indices are aliquot-specific), and aliquots are subsequently pooled into a single pool prior to sequencing. The deconvolution of sequencing reads to original molecules is performed using the partition index, start/stop positions, and (for sample demultiplexing) the sample index. In Variation #2 (FIG. 15C), each column of wells receives the same partition index whereas partition indices vary across each row, such that partition indices are aliquot-specific only with respect to a subset of the aliquots (and not all aliquots). In this variation, each row of aliquots is pooled (i.e. the pooling is amongst aliquots differentially labelled with partition indices), and each subset pool is sequenced separately (FIG. 15D). For example, each of the eight subset pools A-H can be loaded onto a separate lane of a flow cell comprising eight lanes (or loaded on different flow cells or different sequencing instruments). The deconvolution of sequencing reads to original molecules is performed using the partition index, the separate sequencing, start/stop positions, and (for sample demultiplexing) the sample index.

Figure 16E:
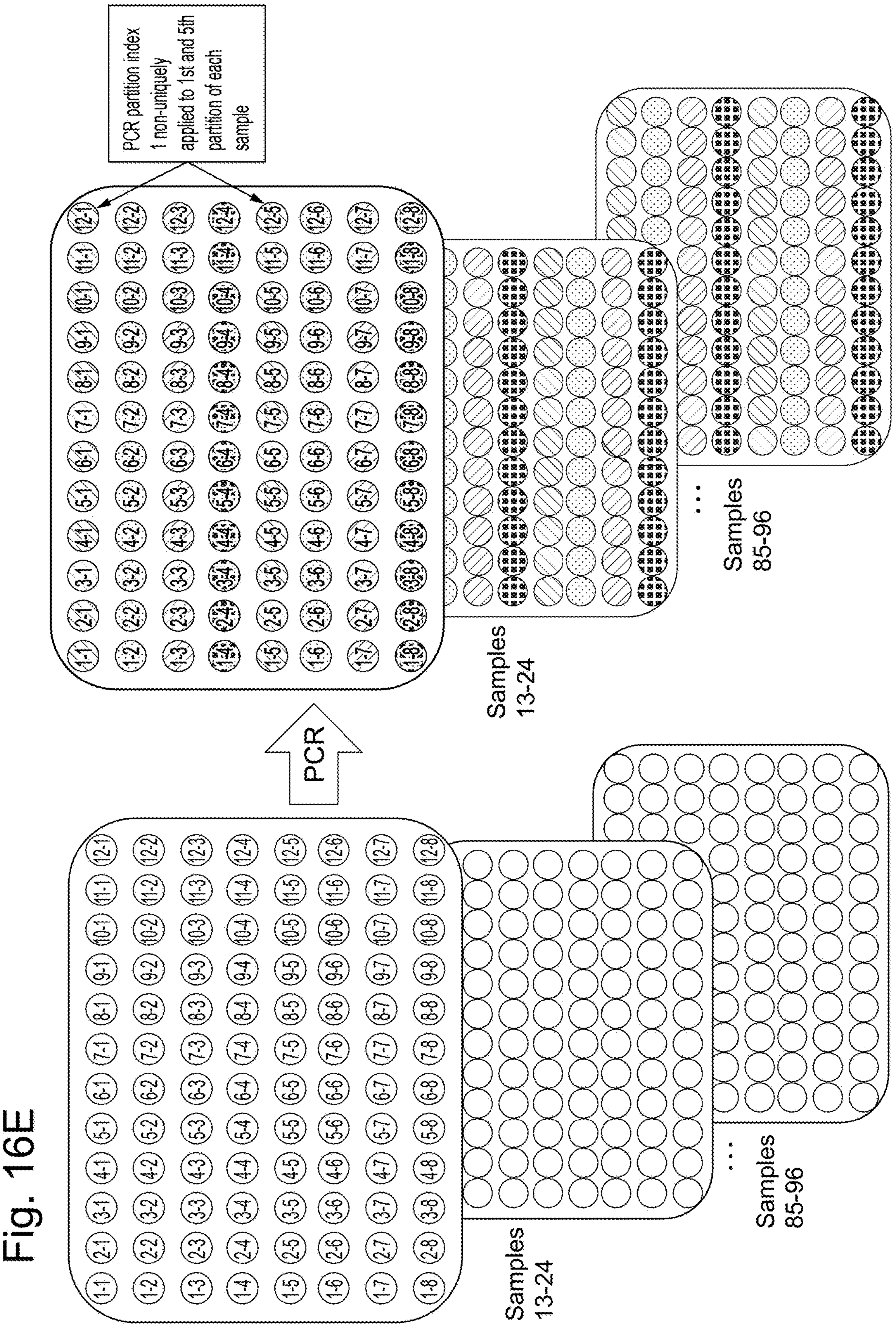

The methods of the present invention do not necessarily involve an initial step of sample mixing before partitioning. Mixing or pooling nucleic acids from different samples after initial processing steps advantageously allows different samples to be subjected to different processing steps (e.g. different enrichment reactions). FIGS. 16A-E show a protocol according to the invention, wherein each of 96 samples is partitioned into eight aliquots, i.e. one column of wells per sample in this illustrative embodiment (FIG. 16A). The particular numbers of samples and partitions are provided as an example. Partition indices are introduced via PCR, wherein four different partition indices are used, such that two aliquots of each sample receive the same partition index (FIGS. 16B and 16E). Aliquots of the same sample that have been differentially labelled with partition indices are then pooled such that two subset pools are generated per sample (FIG. 16C), which in turn means that two enrichment reactions are performed per sample (the enrichment reactions are performed on the subset pool). The two different subset pools deriving from the same sample are sequenced separately (e.g. in different lanes), and subsequent deconvolution of sequencing reads to original molecules is performed using the partition index, the separate sequencing, and start/stop positions (FIG. 16D). In FIGS. 16A-E, the partition indices are not sample-specific (the partition indices are the same across rows), so the method as shown in the figure uses tagging with sample indices before sample multiplexing (as shown in FIGS. 16A-E, one subset pool per sample is pooled and sequenced together after enrichment). Alternatively, partition indices can be sample-specific, e.g. each column of wells can receive a different set of four partition indices; in such a case the ligation of separate indices for sample demultiplexing is not required. Demultiplexing by sample of origin is based on the sample index or the sample-specific partition index.

Another or further level of molecular identification can be provided by indices used to help track and distinguish between individual molecules. For such cases, at least two different ('first') index sequences are used for tagging, and tagging preferably occurs at both ends of an analyte, such that tagging with a population of indices having x different index sequences provides $x^2$ different combined index sequences that can be used for molecular identification. The tagging with such indices is preferably by ligation (e.g. wherein the indices are ligated as part of adapters) and prior to any amplification step. Such indices preferably have the same characteristics as sample indices discussed herein, and indeed sample indices can be 'first indices' (and vice versa). For example, in the variations of FIGS. 15 and 16, multiple different sample indices per sample can be used such that the sample indices provide an additional level of molecular identification. However, first indices are not necessarily sample-specific and not necessarily used for demultiplexing by sample of origin, e.g. in cases where the partition indices are sample-specific.

Thus, methods according to the present invention can involve (at least) a bi-level or tri-level molecular identification scheme that involves deconvoluting sequencing reads by aliquot via the partition index and/or separate sequencing and, additionally, deconvoluting sequencing reads using these first indices (and alignment position).

Table 1 below shows exemplary bi- and tri-level molecular identification schemes according to the present invention. The bi-level versions in the below table use the following 'levels' of indexing for molecular identification: partition indices and 'physical' indexing (version A), first indices and 'physical' indexing (version B), or first indices and partition indices (version C). For each embodiment, molecular identification additionally involves use of alignment positions (e.g. same start and stop points).

In any of the methods of the claimed invention, including those in Table 1 below, sample multiplexing and subsequent demultiplexing of sequencing reads can be performed with the help of sample-specific indices, e.g. sample-specific partition indices, sample-specific first indices, or separate sample indices. Thus, for example, bi-level version A of the table below can use a separate sample index or sample-specific partition indices (in which case other indices can be completely absent). Bi-level version B can use sample-specific first indices (in which case partition indices can be completely absent) or a single, sample-specific index introduced at the level of the partitions (which, however, is not used as a partition index for molecular identification). In bi-level version C and the tri-level embodiment, the partition indices or the first indices can be sample-specific.

TABLE 1

Bi-level and Tri-level molecular identification schemes.

| Embodiment | First indices for 'virtual' partitioning? | # of aliquots per sample (example) | # of separate sequencing reactions per sample (example) | Tracking of aliquots via . . . |
|---|---|---|---|---|
| Bi-level version A | No | 8 (labelled with 4 different partition indices per sample) | 2 | Partition indices and separate sequencing |
| Bi-level version B | Yes (e.g. 2) | 2 | 2 | Separate sequencing |
| Bi-level version C | Yes (e.g. 2) | 4 (labelled with 4 different partition indices per sample) | 1 | Partition indices (aliquot-specific) |
| Tri-level | Yes (e.g. 2) | 4 (labelled with 2 different partition indices per sample) | 2 | Partition indices and separate sequencing |

Pooling all aliquots deriving from the same sample into a single pool prior to subsequent steps such as enrichment and sequencing (see e.g. bi-level version C) simplifies handling and minimizes reagent costs per sample. Such an approach requires that partition indices are aliquot-specific, otherwise the aliquot of origin cannot be tracked and collisions of molecules with the same start/stop positions from aliquots labelled with the same partition index cannot be resolved with the partition index.

'Physical' partitioning via separate sequencing, e.g. by keeping aliquots separate or generating multiple subset pools for each sample from aliquots differentially labelled with partition indices (see e.g. bi-level versions A & B, and the tri-level embodiment), provides robustness against reaction failure and the option to perform different processing steps on different subset pools (e.g. enriching for different sequences, or performing base conversion in one subset pool but not another), and advantageously reduces the number of different partition indices required per sample for a given number of aliquots.

The total indexing provided by different embodiments of the present invention is a function of the number of 'real' and 'virtual' partitions provided by the (at least) two or three levels of molecular identification. For example, bi-level versions A and B provide a total indexing of 8 and bi-level version C and the tri-level embodiment provide a total indexing of 16 (assuming first index ligation to both ends of the analytes such that 2 different first indices provide 4 'virtual' partitions).

On the one hand, partitioning a sample into too many aliquots leads to higher reagent costs and other downsides associated with separately handling a large number of aliquots. On the other hand, partitioning a sample into too few aliquots can result in a high incidence of 'collisions' wherein a given partition receives too many nucleic acid molecules sharing the same alignment position (such as the same start and stop points). The extent to which collisions occur in a sample is a function of sample input amount (the higher the sample input amount, the higher the level of collisions; see FIG. 1). Furthermore, different applications can have a different tolerance to collisions. In particular, the accuracy of somatic indel and single nucleotide variation detection can be more affected by unresolved collisions than counting applications such as copy number variation detection. For example, whereas a collision between a wild-type molecule and a mutated molecule can destroy evidence of a somatic SNV, (accurate) CNV detection can be less affected by such collisions e.g. because the rate of collisions can be estimated and corrected for in CNV and other counting applications. The methods of the invention provide an optimized number of partitions for use with typical cell-free DNA sample sizes and for different applications.

Additionally, it can be desirable to have a flexible method in which the degree to which collisions occur or can be successfully resolved is adjustable e.g. in response to differing sample input amounts or intended application. Varying the number of aliquots into which samples are partitioned can be inexpedient as it may complicate assay automation and restrict sample multiplexing (e.g. when working with samples having significantly different amounts of input DNA). Molecular identification schemes that use first indices according to the present invention provide the desired flexibility without these drawbacks, because the number of 'virtual' partitions, i.e. the number of different first indices for distinguishing between individual molecules, can be readily adjusted depending on how many collisions are expected and/or can be tolerated. Thus, the methods of the present invention can involve the partitioning into a fixed, set, or pre-determined number of aliquots (e.g. irrespective of sample input amount or intended application) while the number of different first indices used can be varied (e.g. increased for large samples or where the intended analysis is SNV detection rather than CNV detection).

In the methods of the invention, the number of different first indices used would typically not be sufficient (alone or in combination with the alignment position) to resolve all or nearly all collisions (i.e. molecules with the same start/stop points). Rather, acceptable deconvolution success is achieved as a result of the combination of the one or two levels of molecular identification provided by the partition index and/or separate sequencing and the additional 'virtual' partitions provided by tagging analytes with different first indices (together with alignment position).

XI. CODEC Sequencing

Errors in PCR/sequencing, as well as DNA damage to a single strand can be mistaken for true somatic mutations, and limit achievable mutation detection sensitivity performance. Numerous error-correction approaches exist typically requiring deep (er) sequencing, molecular barcodes, and/or loss of double-stranded support/tracking. One example is Concatenating Original Duplex for Error Correction (CODEC) protocol that enables double-strand tracking without increasing sequencing costs, using a hybrid method that combines the massively parallel nature of next generation sequencing (NGS) and the resolution of single-molecule sequencing. CODEC involves reading both strands of each DNA duplex with single NGS read pairs. The method relies on differences between concatenated sequences to indicate alterations confined to one strand from either noncanonical base pairing created by nucleobase damage or an error introduced during PCR amplification or sequencing. As this is applicable to a variety of scenarios CODEC has compatibility with major NGS workflows ranging from targeted sequencing to whole-genome sequencing (WGS). As originally described CODEC relies on molecular barcodes. However, the method can be adapted to use of sample and partition indexes as described herein. to reduce, complexity, time and/or cost.

Described herein is a method using aspects of concatenating error correction techniques such as CODEC, but with partitioning library preparation to enable same functionality and molecular resolution, without requiring use of molecular barcodes/UMIs.

As described in Bae et al. Nature Genetics 55, 871-879 (2023), a typical adapter duplex is replaced with the CODEC adapter quadruplex, also referred to as a concatenating adapter, containing all elements required for NGS. Double-stranded segments of the adapter are designed to hold the whole quadruplex and introduced single-stranded. After adapter ligation seals both ends of an input molecule, strand displacing extension initiates at the remaining 3'-ends to elongate each strand by using the opposite strand as a template. This allows CODEC to physically concatenate the Watson strand with the reverse complement of the Crick strand into a single strand. The resulting structure is two original strands concatenated with the CODEC linker in the middle and Illumina adapters on both sides.

Here, CODEC ligation adapters are constructed with modifications to accommodate a mixed sample partitioning platform. CODEC 1 adapters include four single-stranded oligonucleotides. First and second oligonucleotides have mutually complementary 3' ends duplexed with one another. A third oligonucleotide includes a 3' end and a 5' tail, the 3' end being duplexed with the 5' end of the first oligonucleotide. The fourth oligonucleotide likewise includes a 3' end a 5' tail, the 3' end being duplexed with the 5' end of the second oligonucleotide. In use the 5' ends of the first and second oligonucleotides are ligated to the 3' ends of a double-stranded target nucleic acid to be sequenced. The resulting partially circular DNA then undergoes a strand-displacing extension reaction from the 3' ends of the first and second oligonucleotides generating a double-stranded concatemer in which one strand includes an original Watson strand and complement of the original Crick strand of the target, and the other strand includes the original Crick strand and complement of the Watson strand of the target. Between the two mentioned components for each of the concatemer strand are sequences of the first and second oligonucleotide and their complements. Flanking the concatemers are sequences from the third and four oligonucleotides and their concatemers. The first and/or second oligonucleotides can include one or more index sequences, for example, a sample index. Primers complementary to segments of the third and four oligonucleotides can also include indexes, for example, a partition index.

Thus, in any of the disclosed methods reference to an adapter can be understood as referring to CODEC adapter as described above including an index, which can a sample index or first index as described herein, Likewise in any of the disclosed methods reference to forward and reverse primers can be understood as referring to such primers used in the CODEC method, which may include one or more indexes, for example, a partition index.

In an exemplary implementation, the sample index of the original method is retained with removal of the UMI. P5, P7 and are replaced with universal primer sequences at the 5' ends of the first and second adapter sequences. After the CODEC ligation and strand displacing reaction, a sample or pool of samples is partitioned into aliquots. Each aliquot then undergoes amplification with primers complementary to the universal primer sequences, which contain and append to the molecule in amplification both partition index (ices) and flow cell primer sequences (P5,P7). In sequencing, the sample index (ices) are read in-line in standard reads 1,2. The partition indices are read in custom index reads, using the appropriate primers depending on sequencing orientation of index reads on the Illumina platform. P5 or a forward universal primer sequence can be used as custom index primer to read the forward partition index, and P7 or a reverse universal primer sequence can be used to read the reverse partition index.

As an exemplary workflow, ligation adapters for concatenation on two strands are utilized, but the unique molecular identifier (UMI) barcode is removed. A sample barcode can optionally be retained. The outer-end adapter sequences are switched from ILMN flowcell primer sequences (P5, P7) to new 'partition amplification' primers (any sequence that doesn't interfere with ILMN reads/clustering). Also, new 'Partition index primers' are introduced that contain the 'partition amplification' primer sequences, a partition index, and the ILMN flowcell primers (P5,P7) as outer ends. Lastly, custom index primers are used in sequencing that prime either off of P5,P7 or the 'partition amplification' primer sequences to read the partition index, during ILMN 15,17 index reads.

An illustrative exemplary protocol includes the following steps: (1) Sample-barcoded, modified CODEC adapter ligation to DNA molecules from a given sample; (2) Strand displacing extension; (3) Mixed sample partitioning procedure (distributing aliquots of every sample into multiple partitions); (4) Amplifying each partition, with primers that append a partition index, along with ILMN flowcell primers; (5) Hybrid-capture region targeting (OPTIONAL); (6) Post capture amplification (OPTIONAL); (7) NGS sequencing with custom index primers to sequence the partition barcode(s); (8) Post sequencing demultiplexing of sample by sample index, and molecules by partition index and start-stop position. In various embodiments, variations can involve the ds-strand concatenating adapter design, with adjustments possible in ligating sample with sample-index in adapter.

In another example, a different sequence is described which maintain steps of performing mixed partitioning, and tagging each partition with a partition index, that is sequenceable. As shown below, it is possible to perform the strand-displacing extension after mixed sample partitioning, but before the partition amplification step. As described, both hybrid-capture region targeting and post capture amplification are optionally applied.

Therefore, a further illustrative exemplary protocol includes the following steps: (1) Sample-barcoded, modified CODEC adapter ligation to DNA molecules from a given sample; (2) Mixed sample partitioning procedure (distributing aliquots of every sample into multiple partitions); (3) Strand displacing extension; (4) Amplifying each partition, with primers that append a partition index, along with ILMN flowcell primers; (5) NGS sequencing with custom index primers to sequence the partition barcode(s); (6) Post sequencing demultiplexing of sample-by-sample index, and molecules by partition index and start-stop position.

XII. Applications a. Cancer and Other Diseases

The present methods can be used to diagnose presence of conditions, particularly cancer, in a subject, to characterize conditions (e.g., selection of appropriate treatment or staging cancer or determining heterogeneity of a cancer), monitor response to treatment of a condition, effect prognosis risk of developing a condition or subsequent course of a condition.

Various cancers may be detected using the present methods. Cancers cells, as most cells, can be characterized by a rate of turnover, in which old cells die and replaced by newer cells. Generally dead cells, in contact with vasculature in a given subject, may release DNA or fragments of DNA into the blood stream. This is also true of cancer cells during various stages of the disease. Cancer cells may also be characterized, dependent on the stage of the disease, by various genetic aberrations such as copy number variation as well as rare mutations. This phenomenon may be used to detect the presence or absence of cancers individuals using the methods described herein.

The types and number of cancers that may be detected may include blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors and the like.

Cancers can be detected from genetic variations including mutations (e.g., SNVs), rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection and cancer.

Genetic data can also be used for characterizing a specific form of cancer. Cancers are often heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer and allow either a subject or practitioner to adapt treatment options in accord with the progress of the disease. Some cancers progress, becoming more aggressive and genetically unstable. Other cancers may remain benign, inactive or dormant. The system and methods of this disclosure can be useful in determining disease progression.

Accordingly, the present methods can be used to diagnose the presence of a condition, e.g., cancer or precancer, in a subject, to characterize a condition (such as to determine a cancer stage or heterogeneity of a cancer), to monitor a subject's response to receiving a treatment for a condition (such as a response to a chemotherapeutic or immunotherapeutic), assess prognosis of a subject (such as to predict a survival outcome in a subject having a cancer), to determine a subject's risk of developing a condition, to predict a subsequent course of a condition in a subject, to determine metastasis or recurrence of a cancer in a subject (or a risk of cancer metastasis or recurrence), and/or to monitor a subject's health as part of a preventative health monitoring program (such as to determine whether and/or when a subject is in need of further diagnostic screening). The present disclosure can also be useful in determining the efficacy of a particular treatment option. Successful treatment options may result in changes in levels of different immune cell types (including rare immune cell types), and/or increase the amount of copy number variation, rare mutations, and/or cancer-related epigenetic signatures (such as hypermethylated regions or hypomethylated regions) detected in, e.g., a sample from a subject, such as detected in a subject's blood (such as in DNA isolated from a buffy coat sample or any other sample comprising cells, such as in a blood sample (e.g., a whole blood sample, a leukapheresis sample, or a PBMC sample) from the subject) if the treatment is successful as more cancer cells may die and shed DNA, or, e.g., if a successful treatment results in an increase or decrease in the quantity of a specific immune cell type in the blood and an unsuccessful treatment results in no change. In other examples, this may not occur. These changes may be useful in selecting a therapy.

Additionally, if a cancer is observed to be in remission after treatment, the present methods can be used to monitor the likelihood of residual disease or the likelihood of recurrence of disease.

In some embodiments, the present methods are used for screening for a cancer, such as a metastasis, or in a method for screening cancer, such as in a method of detecting the presence or absence of a metastasis. For example, the sample can be a sample from a subject who has or has not been previously diagnosed with cancer. In some embodiments, a sample is obtained from a subject who was previously diagnosed with the cancer and received one or more previous cancer treatments, optionally wherein the sample is obtained at one or more preselected time points following the one or more previous cancer treatments. In some embodiments, a sample is obtained from a subject who was previously diagnosed with the cancer, and the sample is obtained from the subject before the subject receives a cancer treatment. In some embodiments, one or more, such as 1, 2, 3, 4, 5, 6, 7, 8, 9, 10, or more samples are collected from a subject as described herein, such as before and/or after the subject is diagnosed with a cancer. In some embodiments, the subject may or may not have cancer. In some embodiments, the subject may or may not have an early-stage cancer. In some embodiments, the subject has one or more risk factors for cancer, such as tobacco use (e.g., smoking), being overweight or obese, having a high body mass index (BMI), being of advanced age, poor nutrition, high alcohol consumption, or a family history of cancer.

In some embodiments, the subject has used tobacco, e.g., for at least 1, 5, 10, or 15 years. In some embodiments, the subject has a high BMI, e.g., a BMI of 25 or greater, 26 or greater, 27 or greater, 28 or greater, 29 or greater, or 30 or greater. In some embodiments, the subject is at least 40, 45, 50, 55, 60, 65, 70, 75, or 80 years old. In some embodiments, the subject has poor nutrition, e.g., high consumption of one or more of red meat and/or processed meat, trans fat, saturated fat, and refined sugars, and/or low consumption of fruits and vegetables, complex carbohydrates, and/or unsaturated fats. High and low consumption can be defined, e.g., as exceeding or falling below, respectively, recommendations in Dietary Guidelines for Americans 2020-2025, available at dietaryguidelines.gov/sites/default/files/2021-03/Dietary_Guidelines_for_Americans-2020-2025.pdf. In some embodiments, the subject has high alcohol consumption, e.g., at least three, four, or five drinks per day on average (where a drink is about one ounce or 30 mL of 80-proof hard liquor or the equivalent). In some embodiments, the subject has a family history of cancer, e.g., at least one, two, or three blood relatives were previously diagnosed with cancer. In some embodiments, the relatives are at least third-degree relatives (e.g., great-grandparent, great aunt or uncle, first cousin), at least second-degree relatives (e.g., grandparent, aunt or uncle, or half-sibling), or first-degree relatives (e.g., parent or full sibling).

Typically, the disease under consideration is a type of cancer, such as any referred to herein. The types and number of cancers that may be detected may include blood cancers, brain cancers, eye cancers, oral cancers, head and neck cancers, gallbladder cancers, endometrial cancers, ovarian cancers, uterine cancers, prostate cancers, esophageal cancers, lung cancers, skin cancers, nose cancers, throat cancers, liver cancers, bone cancers, lymphomas, leukemias, pancreatic cancers, skin cancers, gastrointestinal cancers, bowel cancers, colorectal cancers, colon cancers, rectal cancers, thyroid cancers, bladder cancers, kidney cancers, mouth cancers, stomach cancers, breast cancers, solid state tumors, heterogeneous tumors, homogenous tumors and the like. Specific examples of such cancers include biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, Wilms tumor, leukemia, acute lymphocytic leukemia (ALL), acute myeloid leukemia (AML), chronic lymphocytic leukemia (CLL), chronic myeloid leukemia (CML), chronic myelomonocytic leukemia (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas, prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma. In some embodiments, the cancer is a hematological cancer. In other embodiments, the cancer is a type of cancer that is not a hematological cancer, e.g., a solid tumor cancer such as a carcinoma, adenocarcinoma, or sarcoma. Type and/or stage of cancer can be detected from genetic variations including mutations, rare mutations, indels, rearrangements, copy number variations, transversions, translocations, recombinations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, and abnormal changes in nucleic acid 5-methylcytosine. In some embodiments, the cancer is a type of cancer that is not a hematological cancer, e.g., a solid tumor cancer such as a carcinoma or sarcoma.

The present methods can be used to generate a profile, fingerprint, or set of data that is a summation of information derived from different cells in a heterogeneous disease. This set of data may comprise RNA levels, cell type levels, inferred RNA levels for one or more cell types, and/or additional information obtainable from methods described herein.

Genetic data can also be used for characterizing a specific form of cancer. Cancers are often heterogeneous in both composition and staging. Genetic profile data may allow characterization of specific sub-types of cancer may be important in the diagnosis or treatment of that specific sub-type. This information may also provide a subject or practitioner clues regarding the prognosis of a specific type of cancer and allow either a subject or practitioner to adapt treatment options in accord with the progress of the disease. Some cancers can progress to become more aggressive and genetically unstable. Other cancers may remain benign, inactive or dormant. The methods of this disclosure may be useful in determining disease progression.

Further, the methods of this disclosure may be used to characterize the heterogeneity of an abnormal condition in a subject. Such methods can include, e.g., generating a gene expression profile using RNA derived from the subject. In some embodiments, an abnormal condition is cancer. In some embodiments, the abnormal condition may be one resulting in a heterogeneous genomic population. In the example of cancer, some tumors are known to comprise tumor cells in different stages of the cancer. In other examples, heterogeneity may comprise multiple foci of disease. Again, in the example of cancer, there may be multiple tumor foci, such as where one or more foci (such as one or more tumor foci) are the result of metastases that have spread from a primary site of a cancer. The tissue(s) of origin can be useful for identifying organs affected by the cancer, including the primary cancer and/or metastatic tumors.

The present methods can be used to diagnose, prognose, monitor or observe cancers, precancers, or other diseases. In some embodiments, the methods herein do not involve the diagnosing, prognosing or monitoring a fetus and as such are not directed to non-invasive prenatal testing. In other embodiments, these methodologies may be employed in a pregnant subject to diagnose, prognose, monitor or observe cancers or other diseases in an unborn subject whose RNA and other polynucleotides may co-circulate with maternal molecules.

Non-limiting examples of other genetic-based diseases, disorders, or conditions that are optionally evaluated using the methods and systems disclosed herein include achondroplasia, alpha-1 antitrypsin deficiency, antiphospholipid syndrome, autism, autosomal dominant polycystic kidney disease, Charcot-Marie-Tooth (CMT), cri du chat, Crohn's disease, cystic fibrosis, Dercum disease, down syndrome, Duane syndrome, Duchenne muscular dystrophy, Factor V Leiden thrombophilia, familial hypercholesterolemia, familial Mediterranean fever, fragile X syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency (SCID), sickle cell disease, spinal muscular atrophy, Tay-Sachs, thalassemia, trimethylaminuria, Turner syndrome, velocardio facial syndrome, WAGR syndrome, Wilson disease, or the like.

Where a cancer recurrence score is determined, it may further be used to determine a cancer recurrence status. The cancer recurrence status may be at risk for cancer recurrence, e.g., when the cancer recurrence score is above a predetermined threshold. The cancer recurrence status may be at low or lower risk for cancer recurrence, e.g., when the cancer recurrence score is above a predetermined threshold. In particular embodiments, a cancer recurrence score equal to the predetermined threshold may result in a cancer recurrence status of either at risk for cancer recurrence or at low or lower risk for cancer recurrence.

In some embodiments, a cancer recurrence score is compared with a predetermined cancer recurrence threshold, and the subject is classified as a candidate for a subsequent cancer treatment when the cancer recurrence score is above the cancer recurrence threshold or not a candidate for therapy when the cancer recurrence score is below the cancer recurrence threshold. In particular embodiments, a cancer recurrence score equal to the cancer recurrence threshold may result in classification as either a candidate for a subsequent cancer treatment or not a candidate for therapy.

In some embodiments, the methods disclosed herein comprise determining the likelihood that the subject from which the sample was obtained has cancer, precancer, an infection, transplant rejection, or other diseases or disorder that is related to changes in proportions of types of immune cells. As discussed herein, comparisons of immune cell identities and/or immune cell quantities/proportions between two or more samples collected from a subject at two different time points can allow for monitoring of one or more aspects of a condition in the subject over time, such as a response of the subject to a treatment, the severity of the condition (such as a cancer stage) in the subject, a recurrence of the condition (such as a cancer), and/or the subject's risk of developing the condition (such as a cancer).

The methods discussed above may further comprise any compatible feature or features set forth elsewhere herein, including in the section regarding methods of determining a risk of cancer recurrence in a subject and/or classifying a subject as being a candidate for a subsequent cancer treatment.

The present methods can also be used to monitor therapy. For example, a successful treatment can initially be associated with an increase in nucleotide or copy number variations in cell free DNA as cancer cells die and release their DNA to the circulation. This initial increase can be followed by a decrease reflecting fewer if any remaining cancer cells to release their DNA. There can also be a subsequent increase in nucleotide or copy number variations following a period of remission providing an indication of recurrence of the cancer.

The present methods can also be used for detecting genetic variations in conditions other than cancer. Immune cells, such as B cells, undergo copy number variation associated with certain diseases. Clonal expansions can be monitored using copy number variation detection as a measure of disease progression. The present methods may be used to determine or profile rejection activities of the host body, as immune cells attempt to destroy transplanted tissue to monitor the status of transplanted tissue as well as altering the course of treatment or prevention of rejection. Copy number variation or variant nucleotide can be used to determine how a population of pathogens are changing during the course of infection. For example, during chronic infections, such as HIV/AIDS or Hepatitis infections, viruses may change life cycle state and/or mutate into more virulent forms during the course of infection.

The present methods can be used to generate or profile, fingerprint or set of data that is a summation of genetic information derived from different cells in a heterogeneous disease. This set of data may comprise copy number variation and nucleotide variation or both.

The present methods can be used to diagnose, prognose, monitor or observe cancers or other diseases of fetal origin. That is, these methodologies can be employed in a pregnant subject to diagnose, prognose, monitor or observe cancers or other diseases in an unborn subject whose DNA and other nucleic acids may co-circulate with maternal molecules.

In certain embodiments, the present methods can be used to determine minimal residual disease (MRD) of a subject. In some embodiments, the methods may be directed to determining MRD by using a tissue-informed assay (i.e., using a tissue sample collected from a patient to determine a personalized panel to enrich for one or more genomic and/or epigenomic variants in a subsequent blood sample from the patient) or a tissue-naïve assay.

In certain embodiments, the present methods can integrate genomic and/or epigenomic data with proteomic (proteins and their post-translational modifications), transcriptomic, fragmentomic, immunological, histological, and/or other analyte-specific data to determine disease initiation, progression, malignant transformation, and therapeutic outcomes.

b. Methods of Determining a Risk of Cancer Recurrence in a Subject and/or Classifying a Subject as being a Candidate for a Subsequent Cancer Treatment In some embodiments, a method provided herein is or comprises a method of determining a risk of cancer recurrence in a subject. In some embodiments, a method provided herein is or comprises a method of detecting the presence of absence of a metastasis in a subject. In some embodiments, a method provided herein is or comprises a method of classifying a subject as being a candidate for a subsequent cancer treatment.

Any of such methods may comprise collecting nucleic acids (e.g., originating or derived from an immune cell or a cancer cell) from the subject diagnosed with the cancer at one or more preselected timepoints following one or more previous cancer treatments to the subject. Similarly, any of such methods may comprise collecting nucleic acids (e.g., originating or derived from an immune cell or a cancer cell) from the subject diagnosed with the cancer at one or more preselected timepoints preceding one or more previous cancer treatments to the subject. The subject may be any of the subjects described herein. The nucleic acids may be DNA or RNA from a sample comprising cells or a blood sample (e.g., a buffy coat sample, a whole blood sample, a leukapheresis sample, or a PBMC sample). The nucleic acid molecules may comprise DNA or RNA obtained from a tissue sample.

Any of such methods may comprise capturing target regions from DNA or RNA (or cDNA prepared from the RNA) from the subject whereby a captured set of nucleic acid molecules is produced. The capturing step may be performed according to any of the embodiments described elsewhere herein.

In any of such methods, the previous cancer treatment may comprise surgery, administration of a therapeutic composition, and/or chemotherapy.

Any of such methods may comprise sequencing the captured nucleic acid molecules, whereby a set of sequence information is produced.

Methods of determining a risk of cancer recurrence in a subject may comprise determining a cancer recurrence score that is indicative of the presence or absence, or amount, of nucleic acid molecules originating or derived from an immune cell or a cancer cell for the subject.

The cancer recurrence score may further be used to determine a cancer recurrence status. The cancer recurrence status may be at risk for cancer recurrence, e.g., when the cancer recurrence score is above a predetermined threshold. The cancer recurrence status may be at low or lower risk for cancer recurrence, e.g., when the cancer recurrence score is above a predetermined threshold. In particular embodiments, a cancer recurrence score equal to the predetermined threshold may result in a cancer recurrence status of either at risk for cancer recurrence or at low or lower risk for cancer recurrence.

Methods of classifying a subject as being a candidate for a subsequent cancer treatment may comprise comparing the cancer recurrence score of the subject with a predetermined cancer recurrence threshold, thereby classifying the subject as a candidate for the subsequent cancer treatment when the cancer recurrence score is above the cancer recurrence threshold or not a candidate for therapy when the cancer recurrence score is below the cancer recurrence threshold. In particular embodiments, a cancer recurrence score equal to the cancer recurrence threshold may result in classification as either a candidate for a subsequent cancer treatment or not a candidate for therapy. In some embodiments, the subsequent cancer treatment comprises chemotherapy or administration of a therapeutic composition.

Any of such methods may comprise determining a disease-free survival (DFS) period for the subject based on the cancer recurrence score; for example, the DFS period may be 1 year, 2 years, 3, years, 4 years, 5 years, or 10 years.

In some embodiments, determining the cancer recurrence score may comprise determining at least a first subscore indicative of the levels of particular immune cell types present based on expression levels of target genes. In some embodiments, determining the cancer recurrence score may comprise determining at least a first subscore indicative of the levels of particular immune cell types present based on whole transcriptome sequencing.

In some embodiments, any of such methods may comprise determining a fraction of tumor from the fraction of molecules in the set of sequence information that indicate one or more features indicative of origination from a tumor cell or an immune cell. This may be done for molecules corresponding to some or all of the target genes and/or target regions, e.g., including, e.g., molecules comprising alterations consistent with cancer, such as SNVs, indels, CNVs, and/or fusions. A determination that a fraction of tumor or immune cell RNA is greater than a threshold, such as a threshold corresponding to any of the foregoing embodiments, may be made based on a cumulative probability. For example, the sample was considered positive if the cumulative probability that the tumor fraction was greater than a threshold in any of the foregoing ranges exceeds a probability threshold of at least 0.5, 0.75, 0.9, 0.95, 0.98, 0.99, 0.995, or 0.999. In some embodiments, the probability threshold is at least 0.95, such as 0.99.

In some embodiments, the set of sequence information comprises differential expression data for one or more of a plurality of target genes as described herein, and optionally target region sequences, and determining the cancer recurrence score comprises determining a first subscore indicative of the levels of particular immune cell types, and a second subscore indicative of the amount of SNVs, insertions/deletions, CNVs and/or fusions present in target region sequences, and combining the first and second subscores to provide the cancer recurrence score. Where the subscores are combined, they may be combined by applying a threshold to each subscore independently in target regions, respectively, and greater than a predetermined fraction of abnormal molecules, or training a machine learning classifier to determine status based on a plurality of positive and negative training samples.

In any embodiment where a cancer recurrence score is classified as positive for cancer recurrence, the cancer recurrence status of the subject may be at risk for cancer recurrence and/or the subject may be classified as a candidate for a subsequent cancer treatment.

In some embodiments, the cancer is any one of the types of cancer described elsewhere herein, e.g., colorectal cancer.

c. Methods of Monitoring a Cancer in a Subject Over Time; Sample Collection at Two or More Time Points In some embodiments, the present methods can be used to monitor one or more aspects of a condition in a subject over time, such as a subject's response to receiving a treatment for a condition (such as a response to a chemotherapeutic or immunotherapeutic), the severity of the condition (such as a cancer stage) in the subject, a recurrence of the condition (such as a cancer), and/or the subject's risk of developing the condition (such as a cancer) and/or to monitor a subject's health as part of a preventative health monitoring program (such as to determine whether and/or when a subject is in need of further diagnostic screening), such as based on changes in levels of different immune cell types, including rare immune cell types, in samples collected from a subject over time. In some embodiments, monitoring comprises analysis of at least two samples collected from a subject at least two different time points as described herein.

The methods according to the present disclosure can also be useful in predicting a subject's response to a particular treatment option. Successful treatment options may result in an increase or decrease in the quantity of a specific immune cell type in the blood, or in the expression of one or more of the plurality of genes of a target gene set, and an unsuccessful treatment may result in no change. In other examples, this may not occur. In another example, certain treatment options may be correlated with genetic profiles of cancers over time. This correlation may be useful in selecting a therapy for a subject.

As disclosed herein, methods are provided for monitoring one or more aspects of a condition in a subject over time, such as but not limited to, a subject's response to receiving a treatment for a condition (such as a response to a chemotherapeutic or immunotherapeutic). Thus, some embodiments of the disclosed methods further comprise evaluating or monitoring a response to a treatment in the subject. In some embodiments, the evaluating or monitoring the response to the treatment in the subject comprises comparing the expression levels for the target gene set comprising a plurality of target genes that are differentially expressed in a sample from the subject collected at at least a first time point and a sample from the subject collected at at least a second time point. In some embodiments, the evaluating or monitoring the response to the treatment in the subject comprises comparing the quantities of the immune cell types in a sample from the subject collected at at least a first time point and a sample from the subject collected at at least a second time point. In some embodiments, the first time point is a time point prior to administration of the treatment to the subject, and the second time point is a time point after the administration of the treatment to the subject. In some embodiments, the first time point is a time point after administration of the treatment to the subject, and the second time point is a time point after the administration of the treatment to the subject and after the first time point.

In certain embodiments, one or more samples is collected from the subject at at least 1-10, at least 1-5, at least 2-5, or at least 1, at least 2, least 3, at least 4, at least 5, at least 6, at least 7, at least 8, at least 9, at least 10, at least 15, or at least 20 time points prior to the subject receiving the treatment. In certain embodiments, one or more samples is collected from the subject at at least 1-10, at least 1-5, at least 2-5, or at least 1, at least 2, least 3, at least 4, at least 5, at least 6, at least 7, at least 8, at least 9, at least 10, at least 15, or at least 20 time points after the subject has received the treatment. Sample collection from a subject can be ongoing during and/or after treatment to monitor the subject's response to the treatment.

In some embodiments, samples are not collected from a subject prior to diagnosis of a condition (such as a cancer) or prior to receiving a treatment. In such embodiments, wherein the response of a subject to a treatment, or the course or stage of a condition (such as a cancer) in the subject is being monitored over time, cell types are compared between samples taken at at least 2-10, at least 2-5, at least 3-6, or at least 2, such as at least 3, at least 4, at least 5, at least 6, at least 7, at least 8, at least 9, at least 10, at least 15, or at least 20 time points collected after the subject has been diagnosed and/or after the subject has received the treatment. Sample collection from a subject can be ongoing during and/or after treatment to monitor the subject's response to the treatment.

In some embodiments of the disclosed methods, one or more samples comprising cells or a blood sample (such as one or more whole blood, buffy coat, leukapheresis, or PBMC samples) is collected from a subject at least once per year, such as about 1-12 times or about 2-6 times, such as about 1, 2, 3, 4, 5, 6, 7, 8, 9, 10, 11, or 12 times per year. In other embodiments, one or more samples is collected from the subject less than once per year, such as about once every 13, 14, 15, 16, 17, 18, 19, 20, 21, 22, 23, or 24 months. In some embodiments, one or more samples is collected from the subject about once every 1-5 years or about once every 1-2 years, such as about every 1, 1.5, 2, 2.5, 3, 3.5, 4, 4.5, or 5 years.

In other embodiments of the disclosed methods, one or more samples comprising cells or one or more blood samples, e.g., one or more buffy coat samples, whole blood samples, leukapheresis samples, or PBMC samples, are collected from a subject at least once per week, such as on 1-4 days, 1-2 days, or on 1, 2, 3, 4, 5, 6, or 7 days per week. In certain embodiments, one or more samples is collected from the subject at least once per month, such as 1-15 times, 1-10 times, 2-5 times, or 1, 2, 3, 4, 5, 6, 7, 8, 9, 10, 11, 12, 13, 14, or 15 times per month. In other embodiments, one or more samples is collected from the subject every month, every 2 months, every 3 months, every 4 months, every 5 months, every 6 months, every 7 months, every 8 months, every 9 months, every 10 months, every 11 months, or every 12 months. In some embodiments, one or more samples is collected from the subject at least once per day, such as 1, 2, 3, 4, 5, or 6 times per day. Selection of the one or more sample collection timepoints (e.g., the frequency of sample collection), or of the number of samples to be collected at each timepoint, depends upon the use to which the methods described herein are to be put by, for example, a research scientist or a clinician (such as a physician).

d. Therapies and Related Administration

In certain embodiments, the methods disclosed herein relate to identifying and administering therapies, such as customized therapies, to patients or subjects. In some embodiments, determination of the presence or absence or levels of genetic or epigenomic variations, facilitates selection of appropriate treatment. In some embodiments, the patient or subject has a given disease, disorder or condition, e.g., any of the cancers or other conditions described elsewhere herein. Essentially any cancer therapy (e.g., surgical therapy, radiation therapy, chemotherapy, immunotherapy, and/or the like) may be included as part of these methods.

Typically, the disease under consideration is a type of cancer. Non-limiting examples of such cancers include biliary tract cancer, bladder cancer, transitional cell carcinoma, urothelial carcinoma, brain cancer, gliomas, astrocytomas, breast cancer, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, Wilms tumor, leukemia, acute lymphocytic leukemia (ALL), acute myeloid leukemia (AML), chronic lymphocytic leukemia (CLL), chronic myeloid leukemia (CML), chronic myelomonocytic leukemia (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas, Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma.

Non-limiting examples of other genetic-based diseases, disorders, or conditions that are optionally evaluated using the methods and systems disclosed herein include achondroplasia, alpha-1 antitrypsin deficiency, antiphospholipid syndrome, autism, autosomal dominant polycystic kidney disease, Charcot-Marie-Tooth (CMT), cri du chat, Crohn's disease, cystic fibrosis, Dercum disease, down syndrome, Duane syndrome, Duchenne muscular dystrophy, Factor V Leiden thrombophilia, familial hypercholesterolemia, familial mediterranean fever, fragile X syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency (scid), sickle cell disease, spinal muscular atrophy, Tay-Sachs, thalassemia, trimethylaminuria, Turner syndrome, velocardiofacial syndrome, WAGR syndrome, Wilson disease, or the like.

In certain embodiments, the therapies can include one or more of treatments for target therapies, including abemaciclib, abiraterone acetate, acalabrutinib, adagrasib, adotrastuzumab emtansine, afatinib dimaleate, alectinib, alemtuzumab, alitretinoin, alpelisib, amivantamab-vmjw, anastrozole, apalutamide, asciminib hydrochloride, atezolizumab, atezolizumab, avapritinib, avelumab, axicabtagene ciloleucel, axitinib, belinostat, belzutifan, bevacizumab, bexarotene, binimetinib, blinatumomab, bortezomib, bosutinib, brentuximab vedotin, brexucabtagene autoleucel, brigatinib, cabazitaxel, cabozantinib-s-malate, cabozantinib-s-malate, capmatinib hydrochloride, carfilzomib, cemiplimab-rwlc, ceritinib, cetuximab, ciltacabtagene autoleucel, cobimetinib fumarate, copanlisib hydrochloride, crizotinib, dabrafenib, dabrafenib mesylate, dacomitinib, daratumumab, daratumumab and hyaluronidase-fihj, darolutamide, dasatinib, denileukin diftitox, denosumab, dinutuximab, dostarlimab-gxly, durvalumab, duvelisib, elacestrant dihydrochloride, elotuzumab, enasidenib mesylate, encorafenib, enfortumab vedotin-ejfv, entrectinib, enzalutamide, erdafitinib, erlotinib hydrochloride, everolimus, exemestane, fam-trastuzumab deruxtecan-nxki, fam-trastuzumab deruxtecan-nxki, fedratinib hydrochloride, fulvestrant, futibatinib, gefitinib, gemtuzumab ozogamicin, gilteritinib fumarate, glasdegib maleate, ibritumomab tiuxetan, ibrutinib, idecabtagene vicleucel, idelalisib, imatinib mesylate, infigratinib phosphate, inotuzumab ozogamicin, iobenguane 1 131, ipilimumab, isatuximab-irfc, ivosidenib, ixazomib citrate, lanreotide acetate, lapatinib ditosylate, larotrectinib sulfate, lenvatinib mesylate, letrozole, lisocabtagene maraleucel, loncastuximab tesirine-lpyl, lorlatinib, lutetium Lu 177 vipivotide tetraxetan, lutetium Lu 177-dotatate, margetuximab-cmkb, midostaurin, mirvetuximab soravtansine-gynx, mobocertinib succinate, mogamulizumab-kpkc, mosunetuzumab-axgb, moxetumomab pasudotox-tdfk, naxitamab-gqgk, necitumumab, neratinib maleate, nilotinib, niraparib tosylate monohydrate, nivolumab, nivolumab and relatlimab-rmbw, obinutuzumab, ofatumumab, olaparib, olutasidenib, osimertinib mesylate, pacritinib citrate, palbociclib, panitumumab, pazopanib hydrochloride, pembrolizumab, pemigatinib, pertuzumab, pertuzumab, trastuzumab, and hyaluronidase-zzxf, pexidartinib hydrochloride, pirtobrutinib, polatuzumab vedotin-piiq, ponatinib hydrochloride, pralatrexate, pralsetinib, radium 223 dichloride, ramucirumab, regorafenib, retifanlimab-dlwr, ribociclib, ripretinib, rituximab, rituximab and hyaluronidase human, romidepsin, rucaparib camsylate, ruxolitinib phosphate, sacituzumab govitecan-hziy, selinexor, selpercatinib, selumetinib sulfate, siltuximab, sirolimus protein-bound particles, sonidegib, sorafenib tosylate, sotorasib, sunitinib malate, tafasitamab-cxix, tagraxofusp-erzs, talazoparib tosylate, tamoxifen citrate, tazemetostat hydrobromide, tebentafusp-tebn, teclistamab-cqyv, temsirolimus, tepotinib hydrochloride, tisagenlecleucel, tisotumab vedotin-tftv, tivozanib hydrochloride, toremifene, trametinib, trametinib dimethyl sulfoxide, trastuzumab, tremelimumab-actl, tretinoin, tucatinib, vandetanib, vemurafenib, venetoclax, vismodegib, vorinostat, zanubrutinib, ziv-aflibercept.

In certain embodiments, the therapy administered to a subject comprises at least one chemotherapy drug. In some embodiments, the chemotherapy drug may comprise alkylating agents (for example, but not limited to, Chlorambucil, Cyclophosphamide, Cisplatin and Carboplatin), nitrosoureas (for example, but not limited to, Carmustine and Lomustine), anti-metabolites (for example, but not limited to, Fluorauracil, Methotrexate and Fludarabine), plant alkaloids and natural products (for example, but not limited to, Vincristine, Paclitaxel and Topotecan), anti-tumor antibiotics (for example, but not limited to, Bleomycin, Doxorubicin and Mitoxantrone), hormonal agents (for example, but not limited to, Prednisone, Dexamethasone, Tamoxifen and Leuprolide) and biological response modifiers (for example, but not limited to, Herceptin and Avastin, Erbitux and Rituxan). In some embodiments, the chemotherapy administered to a subject may comprise FOLFOX or FOLFIRI. In certain embodiments, a therapy may be administered to a subject that comprises at least one PARP inhibitor. In certain embodiments, the PARP inhibitor may include OLAPARIB, TALAZOPARIB, RUCAPARIB, NIRAPARIB, among others. Typically, therapies include at least one immunotherapy (or an immunotherapeutic agent). Immunotherapy refers generally to methods of enhancing an immune response against a given cancer type. In certain embodiments, immunotherapy refers to methods of enhancing a T cell response against a tumor or cancer.

In some embodiments, therapy is customized based on the status of a nucleic acid variant as being of somatic or germline origin. In some embodiments, essentially any cancer therapy (e.g., surgical therapy, radiation therapy, chemotherapy, immunotherapy, and/or the like) may be included as part of these methods. Customized therapies can include at least one immunotherapy (or an immunotherapeutic agent). Immunotherapy refers generally to methods of enhancing an immune response against a given cancer type. In certain embodiments, immunotherapy refers to methods of enhancing a T cell response against a tumor or cancer.

In some embodiments, the immunotherapy or immunotherapeutic agent targets an immune checkpoint molecule. Certain tumors are able to evade the immune system by co-opting an immune checkpoint pathway. Thus, targeting immune checkpoints has emerged as an effective approach for countering a tumor's ability to evade the immune system and activating anti-tumor immunity against certain cancers. Pardoll, Nature Reviews Cancer, 2012, 12:252-264.

In certain embodiments, the immune checkpoint molecule is an inhibitory molecule that reduces a signal involved in the T cell response to antigen. For example, CTLA4 is expressed on T cells and plays a role in downregulating T cell activation by binding to CD80 (aka B7.1) or CD86 (aka B7.2) on antigen presenting cells. PD-1 is another inhibitory checkpoint molecule that is expressed on T cells. PD-1 limits the activity of T cells in peripheral tissues during an inflammatory response. In addition, the ligand for PD-1 (PD-L1 or PD-L2) is commonly upregulated on the surface of many different tumors, resulting in the downregulation of anti-tumor immune responses in the tumor microenvironment. In certain embodiments, the inhibitory immune checkpoint molecule is CTLA4 or PD-1. In other embodiments, the inhibitory immune checkpoint molecule is a ligand for PD-1, such as PD-L1 or PD-L2. In other embodiments, the inhibitory immune checkpoint molecule is a ligand for CTLA4, such as CD80 or CD86. In other embodiments, the inhibitory immune checkpoint molecule is lymphocyte activation gene 3 (LAG3), killer cell immunoglobulin like receptor (KIR), T cell membrane protein 3 (TIM3), galectin 9 (GAL9), or adenosine A2a receptor (A2aR).

Antagonists that target these immune checkpoint molecules can be used to enhance antigen-specific T cell responses against certain cancers. Accordingly, in certain embodiments, the immunotherapy or immunotherapeutic agent is an antagonist of an inhibitory immune checkpoint molecule. In certain embodiments, the inhibitory immune checkpoint molecule is PD-1. In certain embodiments, the inhibitory immune checkpoint molecule is PD-L1. In certain embodiments, the antagonist of the inhibitory immune checkpoint molecule is an antibody (e.g., a monoclonal antibody). In certain embodiments, the antibody or monoclonal antibody is an anti-CTLA4, anti-PD-1, anti-PD-L1, or anti-PD-L2 antibody. In certain embodiments, the antibody is a monoclonal anti-PD-1 antibody. In some embodiments, the antibody is a monoclonal anti-PD-L1 antibody. In certain embodiments, the monoclonal antibody is a combination of an anti-CTLA4 antibody and an anti-PD-1 antibody, an anti-CTLA4 antibody and an anti-PD-L1 antibody, or an anti-PD-L1 antibody and an anti-PD-1 antibody. In certain embodiments, the anti-PD-1 antibody is one or more of pembrolizumab (Keytruda®) or nivolumab (Opdivo®). In certain embodiments, the anti-CTLA4 antibody is ipilimumab (Yervoy®). In certain embodiments, the anti-PD-L1 antibody is one or more of atezolizumab (Tecentriq®), avelumab (Bavencio®), or durvalumab (Imfinzi®).

In certain embodiments, the immunotherapy or immunotherapeutic agent is an antagonist (e.g., antibody) against CD80, CD86, LAG3, KIR, TIM3, GAL9, or A2aR. In other embodiments, the antagonist is a soluble version of the inhibitory immune checkpoint molecule, such as a soluble fusion protein comprising the extracellular domain of the inhibitory immune checkpoint molecule and an Fc domain of an antibody. In certain embodiments, the soluble fusion protein comprises the extracellular domain of CTLA4, PD-1, PD-L1, or PD-L2. In some embodiments, the soluble fusion protein comprises the extracellular domain of CD80, CD86, LAG3, KIR, TIM3, GAL9, or A2aR. In one embodiment, the soluble fusion protein comprises the extracellular domain of PD-L2 or LAG3.

In certain embodiments, the immune checkpoint molecule is a co-stimulatory molecule that amplifies a signal involved in a T cell response to an antigen. For example, CD28 is a co-stimulatory receptor expressed on T cells. When a T cell binds to antigen through its T cell receptor, CD28 binds to CD80 (aka B7.1) or CD86 (aka B7.2) on antigen-presenting cells to amplify T cell receptor signaling and promote T cell activation. Because CD28 binds to the same ligands (CD80 and CD86) as CTLA4, CTLA4 is able to counteract or regulate the co-stimulatory signaling mediated by CD28. In certain embodiments, the immune checkpoint molecule is a co-stimulatory molecule selected from CD28, inducible T cell co-stimulator (ICOS), CD137, OX40, or CD27. In other embodiments, the immune checkpoint molecule is a ligand of a co-stimulatory molecule, including, for example, CD80, CD86, B7RP1, B7-H3, B7-H4, CD137L, OX40L, or CD70.

Agonists that target these co-stimulatory checkpoint molecules can be used to enhance antigen-specific T cell responses against certain cancers. Accordingly, in certain embodiments, the immunotherapy or immunotherapeutic agent is an agonist of a co-stimulatory checkpoint molecule. In certain embodiments, the agonist of the co-stimulatory checkpoint molecule is an agonist antibody and preferably is a monoclonal antibody. In certain embodiments, the agonist antibody or monoclonal antibody is an anti-CD28 antibody. In other embodiments, the agonist antibody or monoclonal antibody is an anti-ICOS, anti-CD137, anti-OX40, or anti-CD27 antibody. In other embodiments, the agonist antibody or monoclonal antibody is an anti-CD80, anti-CD86, anti-B7RP1, anti-B7-H3, anti-B7-H4, anti-CD137L, anti-OX40L, or anti-CD70 antibody.

In certain embodiments, the status of a nucleic acid variant from a sample from a subject as being of somatic or germline origin may be compared with a database of comparator results from a reference population to identify customized or targeted therapies for that subject. Typically, the reference population includes patients with the same cancer or disease type as the subject and/or patients who are receiving, or who have received, the same therapy as the subject. A customized or targeted therapy (or therapies) may be identified when the nucleic variant and the comparator results satisfy certain classification criteria (e.g., are a substantial or an approximate match).

In certain embodiments, the customized therapies described herein are typically administered parenterally (e.g., intravenously or subcutaneously). Pharmaceutical compositions containing an immunotherapeutic agent are typically administered intravenously. Certain therapeutic agents are administered orally. However, customized therapies (e.g., immunotherapeutic agents, etc.) may also be administered by any method known in the art, for example, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

In certain embodiments, the present methods are also useful in determining the efficacy of particular treatment options. For example, the number of variations detected, irrespective of their precise identity, is a predictor of amenability to immunotherapy because the mutations create neoepitopes that can be subject of immune attack (see e.g., US20200370129).

Other somatic variations or copy number variations indicate suitability of a particular drug. Some examples of such variations are as follows:

TABLE 2

List of Cancer Types with Associated Drug Treatment and Biomarker.

| Indication/ Cancer type | Drug | Biomarker |
|---|---|---|
| Breast | abemaciclib | CDK4, CDK6 |
| Prostate | abiraterone acetate | CYP17A1 |
| Leukemia | acalabrutinib | BTK |
| Lymphoma | acalabrutinib | BTK |
| Lung | adagrasib | KRAS G12C |
| Breast | ado-trastuzumab emtansine | Tubulin, Her2 |
| Lung | afatinib dimaleate | EGFR + EGFR exon 21 L858R mutation + EGFR-Ex19del + HER2 + HER4 |
| Lung | alectinib | ALK, RET |
| Leukemia | alemtuzumab | CD52 |
| Skin | alitretinoin | RARα + RARβ2 + RARγ |
| Soft tissue sarcoma | alitretinoin | RARα + RARβ2 + RARγ |
| Breast | alpelisib | PI3Kα |
| Lung | amivantamab-vmjw | EGFR + c-MET |
| Breast | anastrozole | Aromatase |
| Prostate | apalutamide | AR |
| Leukemia | asciminib hydrochloride | Bcr-Abl |
| Bladder | atezolizumab | PDL1 |
| Liver and bile duct | atezolizumab | PDL1 |
| Lung | atezolizumab | PDL1 |
| Skin | atezolizumab | PDL1 |
| Soft tissue sarcoma | atezolizumab | PDL1 |
| Gastrointestinal | avapritinib | PDGFRα + c-Kit |
| Systemic mastocytosis | avapritinib | PDGFRα + c-Kit |
| Bladder | avelumab | PDL1 |
| Endocrine and neuroendocrine tumors | avelumab | PDL1 |
| Kidney | avelumab | PDL1 |
| Skin | avelumab | PDL1 |
| Lymphoma | axicabtagene ciloleucel | CD19 |
| Kidney | axitinib | VEGFR1 + VEGFR2 + VEGFR3 |
| Lymphoma | belinostat | HDAC |
| Brain | belzutifan | HIF-2A |
| Kidney | belzutifan | HIF-2A |
| Pancreatic | belzutifan | HIF-2A |
| Ovarian epithelial, fallopian tube, and primary peritoneal | bevacizumab | VEGF-A |
| Brain | bevacizumab | VEGF-A |
| Cervical | bevacizumab | VEGF-A |
| Colorectal | bevacizumab | VEGF-A |
| Kidney | bevacizumab | VEGF-A |

TABLE 2-continued

List of Cancer Types with Associated Drug Treatment and Biomarker.

| Indication/ Cancer type | Drug | Biomarker |
|---|---|---|
| Liver and bile duct | bevacizumab | VEGF-A |
| Lung | bevacizumab | VEGF-A |
| Lymphoma | bexarotene | RXRs |
| Skin | binimetinib | MEK1, MEK2 |
| Leukemia | blinatumomab | CD19, CD3 |
| Lymphoma | bortezomib | Proteasome |
| Multiple myeloma | bortezomib | Proteasome |
| Leukemia | bosutinib | BCR-ABL, SRC |
| Lymphoma | brentuximab vedotin | CD130, Tubulin |
| Leukemia | brexucabtagene autoleucel | CD19 |
| Lymphoma | brexucabtagene autoleucel | CD19 |
| Lung | brigatinib | ALK, EGFR, FLT3, IGF-1R, ROS1 |
| Prostate | cabazitaxel | Tubulin |
| Kidney | cabozantinib-s-malate | AXL + RET + ROS1 + TYRO3 + Tie-2 + TrkB + VEGFR1 + VEGFR2 + VEGFR3 + c-Kit + c-Met |
| Liver and bile duct | cabozantinib-s-malate | AXL + RET + ROS1 + TYRO3 + Tie-2 + TrkB + VEGFR1 + VEGFR2 + VEGFR3 + c-Kit + c-Met |
| Thyroid | cabozantinib-s-malate | AXL + RET + ROS1 + TYRO3 + Tie-2 + TrkB + VEGFR1 + VEGFR2 + VEGFR3 + c-Kit + c-Met |
| Lung | capmatinib hydrochloride | c-Met |
| Multiple myeloma | carfilzomib | protoasome |
| Lung | cemiplimab-rwlc | PD-1 |
| Skin | cemiplimab-rwlc | PD-1 |
| Lung | ceritinib | ALK + IGF-1R + INSR + ROS1 |
| Colorectal | cetuximab | EGFR |
| Multiple myeloma | ciltacabtagene autoleucel | BCMA |
| Skin | cobimetinib fumarate | MEK1, MEK2 |
| Lymphoma | copanlisib hydrochloride | PI3Kα, PI3Kδ |
| Lung | crizotinib | MTH1 |
| Lymphoma | crizotinib | MTH1 |
| Myofibroblastic | crizotinib | MTH1 |
| Brain | dabrafenib | BRAF, CRAF |
| Lung | dabrafenib mesylate | BRAF, CRAF |
| Skin | dabrafenib mesylate | BRAF, CRAF |
| Solid tumors anywhere in the body | dabrafenib mesylate | BRAF, CRAF |
| Thyroid | dabrafenib mesylate | BRAF, CRAF |
| Lung | dacomitinib | EGFR + EGFR exon 21 L858R mutation + EGFR-Ex19del + HER2 + HER4 |
| Multiple myeloma | daratumumab | CD38 + Hyaluronic acid |
| Multiple myeloma | daratumumab and hyaluronidase-fihj | CD38 + Hyaluronic acid |
| Prostate | darolutamide | AR |
| Leukemia | dasatinib | Bcr-Abl + EphA2 + FYN + LCK + PDGFRβ + Protein-tyrosine kinases + SRC + YES1 + c-Kit |
| Neuroblastoma | dinutuximab | GD2 |
| Endometrial | dostarlimab-gxly | PD-1 |
| Solid tumors anywhere in the body | dostarlimab-gxly | PD-1 |
| Liver and bile duct | durvalumab | PDL1 |
| Lung | durvalumab | PDL1 |
| Leukemia | duvelisib | PI3Kγ + PI3Kδ |

TABLE 2-continued

List of Cancer Types with Associated Drug Treatment and Biomarker.

| Indication/ Cancer type | Drug | Biomarker |
|---|---|---|
| Breast | elacestrant dihydrochloride | Erα/ESR1 |
| Multiple myeloma | elotuzumab | SLAMF7 |
| Leukemia | enasidenib mesylate | IDH2 |
| Colorectal | encorafenib | BRAF, BRAF V600E |
| Skin | encorafenib | BRAF V600E, V600K mutation |
| Bladder | enfortumab vedotin-ejfv | Nectin-4, Tubulins |
| Lung | entrectinib | ALK + ROS1 + TRKA + TrkB + TrkC |
| Solid tumors anywhere in the body | entrectinib | ALK + ROS1 + TRKA + TrkB + TrkC |
| Prostate | enzalutamide | AR |
| Bladder | erdafitinib | FGFR1, FGFR2, FGFR3, FGFR4 |
| Lung | erlotinib hydrochloride | EGFR antagonists, EGFR exon 21 L858R mutation inhibitors, EGFR-Ex19del inhibitors |
| Pancreatic | erlotinib hydrochloride | EGFR + EGFR exon 21 L858R mutation + EGFR-Ex19del |
| Breast | everolimus | mTORC1, mTORC2 |
| Kidney | everolimus | mTORC1, mTORC2 |
| Pancreatic | everolimus | mTORC1, mTORC2 |
| Breast | exemestane | Aromatase |
| Breast | fam-trastuzumab deruxtecan-nxki | HER2, TOP1 |
| Gastric | fam-trastuzumab deruxtecan-nxki | HER2, TOP1 |
| Lung | fam-trastuzumab deruxtecan-nxki | HER2, TOP1 |
| Myelodysplastic and myeloproliferative disorders | fedratinib hydrochloride | JAK2, FLT3 |
| Breast | fulvestrant | ER |
| Liver and bile duct | futibatinib | FGFRs |
| Lung | gefitinib | EGFR + EGFR exon 21 L858R mutation + EGFR-Exon 19 deletion |
| Leukemia | gemtuzumab ozogamicin | CD33, DNA |
| Leukemia | gilteritinib fumarate | AXL + FLT3 |
| Leukemia | glasdegib maleate | SMO |
| Lymphoma | ibritumomab tiuxetan | CD20 |
| Leukemia | ibrutinib | BTK |
| Lymphoma | ibrutinib | BTK |
| Multiple myeloma | idecabtagene vicleucel | BCMA |
| Leukemia | idelalisib | PI3Kδ |
| Dermatofibrosarcoma protuberans | imatinib mesylate | BCR-ABL, PDGFR, C-Kit |
| Gastrointestinal | imatinib mesylate | BCR-ABL, PDGFR, C-Kit |
| Leukemia | imatinib mesylate | BCR-ABL, PDGFR, C-Kit |
| Myelodysplastic and myeloproliferative disorders | imatinib mesylate | BCR-ABL, PDGFR, C-Kit |
| Systemic mastocytosis | imatinib mesylate | BCR-ABL, PDGFR, C-Kit |
| Liver and bile duct | infigratinib phosphate | FGFR1 + FGFR2 + FGFR3 + FGFR4 |
| Leukemia | inotuzumab ozogamicin | CD22 + DNA |
| Endocrine and neuroendocrine tumors | iobenguane I 131 | NET |
| Colorectal | ipilimumab | CTLA4 |
| Esophageal | ipilimumab | CTLA4 |
| Kidney | ipilimumab | CTLA4 |
| Liver and bile duct | ipilimumab | CTLA4 |
| Lung | ipilimumab | CTLA4 |
| Malignant mesothelioma | ipilimumab | CTLA4 |

TABLE 2-continued

List of Cancer Types with Associated Drug Treatment and Biomarker.

| Indication/ Cancer type | Drug | Biomarker |
|---|---|---|
| Skin | ipilimumab | CTLA4 |
| Multiple myeloma | isatuximab-irfc | CD38 |
| Leukemia | ivosidenib | IDH1 |
| Multiple myeloma | ixazomib citrate | proteasome |
| Endocrine and neuroendocrine tumors | lanreotide acetate | SSTR |
| Breast | lapatinib ditosylate | EGFR |
| Solid tumors anywhere in the body | larotrectinib sulfate | TRKA + TrkB + TrkC |
| Endometrial | lenvatinib mesylate | FGFR1 + FGFR2 + FGFR3 + FGFR4 + PDGFRα + RET + VEGFR1 + VEGFR2 + VEGFR3 + c-Kit |
| Kidney | lenvatinib mesylate | FGFR1 + FGFR2 + FGFR3 + FGFR4 + PDGFRα + RET + VEGFR1 + VEGFR2 + VEGFR3 + c-Kit |
| Liver and bile duct | lenvatinib mesylate | FGFR1 + FGFR2 + FGFR3 + FGFR4 + PDGFRα + RET + VEGFR1 + VEGFR2 + VEGFR3 + c-Kit |
| Thyroid | lenvatinib mesylate | FGFR1 + FGFR2 + FGFR3 + FGFR4 + PDGFRα + RET + VEGFR1 + VEGFR2 + VEGFR3 + c-Kit |
| Breast | letrozole /Ribociclib Succinate | CDK4/ER |
| Lymphoma | lisocabtagene maraleucel | CD19 |
| Lymphoma | loncastuximab tesirine-lpyl | CD19 + DNA |
| Lung | lorlatinib | ALK + ROS1 |
| Prostate | lutetium Lu 177 vipivotide tetraxetan | PSMA |
| Endocrine and neuroendocrine tumors | lutetium Lu 177-dotatate | SSTR2 |
| Breast | margetuximab-cmkb | HER2 |
| Leukemia | midostaurin | FLT3 + PDGFR + PKC + Syk + VEGFR2 + c-Kit |
| Systemic mastocytosis | midostaurin | FLT3 + PDGFR + PKC + Syk + VEGFR2 + c-Kit |
| Ovarian epithelial, fallopian tube, and primary peritoneal | mirvetuximab soravtansine-gynx | FOLR1 + Tubulin |
| Lung | mobocertinib succinate | EGFR exon 20 + HER2 exon 20 |
| Lymphoma | mogamulizumab-kpkc | CCR4 |
| Lymphoma | mosunetuzumab-axgb | CD20, CD3 |
| Leukemia | moxetumomab pasudotox-tdfk | CD22 |
| Neuroblastoma | naxitamab-gqgk | GD2 |
| Lung | necitumumab | EGFR |
| Breast | neratinib maleate | EGFR, HER2, HER4 |
| Leukemia | nilotinib | Bcr-Abl + CSF-1R + DDR1 + PDGFR + c-Kit |
| Ovarian epithelial, fallopian tube, and primary peritoneal | niraparib tosylate monohydrate | PARP1 + PARP2 |
| Bladder | nivolumab | PD-1 |
| Colorectal | nivolumab | PD-1 |
| Esophageal | nivolumab | PD-1 |

TABLE 2-continued

List of Cancer Types with Associated Drug Treatment and Biomarker.

| Indication/ Cancer type | Drug | Biomarker |
|---|---|---|
| Kidney | nivolumab | PD-1 |
| Liver and bile duct | nivolumab | PD-1 |
| Lung | nivolumab | PD-1 |
| Lymphoma | nivolumab | PD-1 |
| Malignant mesothelioma | nivolumab | PD-1 |
| Skin | nivolumab | PD-1 |
| Stomach (gastric) | nivolumab | PD-1 |
| Skin | nivolumab and relatlimab-rmbw | LAG3 + PD-1 |
| Leukemia | obinutuzumab | CD20 |
| Lymphoma | obinutuzumab | CD20 |
| Leukemia | ofatumumab | CD20 |
| Ovarian epithelial, fallopian tube, and primary peritoneal | olaparib | PARP1, PARP2, PARP3 |
| Breast | olaparib | PARP1, PARP2, PARP3 |
| Pancreatic | olaparib | PARP1, PARP2, PARP3 |
| Prostate | olaparib | PARP1, PARP2, PARP3 |
| Leukemia | olutasidenib | IDH1 |
| Lung | osimertinib mesylate | EGFR + EGFR T790M + EGFR exon 21 L858R mutation + EGFR-Ex19del |
| Myelodysplastic and myeloproliferative disorders | pacritinib citrate | CSF-1R + FLT3 + IRAK1 + JAK2 |
| Breast | palbociclib | CDK4, CDK6 |
| Colorectal | panitumumab | EGFR |
| Kidney | pazopanib hydrochloride | FGFR1 + FGFR3 + Flt3L + ITK + LCK + PDGFRα + PDGFRβ + VEGFR1 + VEGFR2 + VEGFR3 + c-Kit |
| Soft tissue sarcoma | pazopanib hydrochloride | FGFR1 + FGFR3 + Flt3L + ITK + LCK + PDGFRα + PDGFRβ + VEGFR1 + VEGFR2 + VEGFR3 + c-Kit |
| Breast | pembrolizumab | PD-1 |
| Cervical | pembrolizumab | PD-1 |
| Colorectal | pembrolizumab | PD-1 |
| Endometrial | pembrolizumab | PD-1 |
| Esophageal | pembrolizumab | PD-1 |
| Kidney | pembrolizumab | PD-1 |
| Liver and bile duct | pembrolizumab | PD-1 |
| Lung | pembrolizumab | PD-1 |
| Lymphoma | pembrolizumab | PD-1 |
| Skin | pembrolizumab | PD-1 |
| Solid tumors anywhere in the body | pembrolizumab | PD-1 |
| Stomach (gastric) | pembrolizumab | PD-1 |
| Leukemia | pemigatinib | FGFR1, FGFR2, FGFR3, FGFR4 |
| Liver and bile duct | pemigatinib | FGFR1, FGFR2, FGFR3, FGFR4 |
| Lymphoma | pemigatinib | FGFR1, FGFR2, FGFR3, FGFR4 |
| Myelodysplastic and myeloproliferative disorders | pemigatinib | FGFR1, FGFR2, FGFR3, FGFR4 |
| Breast | pertuzumab | HER2 |
| Breast | pertuzumab, trastuzumab, and hyaluronidase-zzxf | HER2, Hyaluronic acid |
| Giant cell tumor | pexidartinib hydrochloride | CSF-1R + FLT3 + c-Kit |
| Lymphoma | pirtobrutinib | BTK C481S |
| Lymphoma | polatuzumab vedotin-piiq | CD79B + Tubulin |
| Leukemia | ponatinib hydrochloride | Bcr-Abl + Protein-tyrosine kinases |

TABLE 2-continued

List of Cancer Types with Associated Drug Treatment and Biomarker.

| Indication/ Cancer type | Drug | Biomarker |
|---|---|---|
| Lymphoma | pralatrexate | Bcr-Abl + Protein-tyrosine kinases |
| Lung | pralsetinib | RET |
| Thyroid | pralsetinib | RET |
| Prostate | radium 223 dichloride | DNA |
| Colorectal | ramucirumab | VEGFR2 |
| Gastric | ramucirumab | VEGFR2 |
| Liver and bile duct | ramucirumab | VEGFR2 |
| Lung | ramucirumab | VEGFR2 |
| Stomach (gastric) | ramucirumab | VEGFR2 |
| Colorectal | regorafenib | Abl family, BRAF, BRAF V600E, CRAF, CSF-1R, DDR2, EphA2, FGFR1, FGFR2, FRK, MAPK11, PDGFRa, PDGFRb, RET,TRKA, Tie-2, VEGFR1, VEGFR2, VEGFR3, c-kit |
| Gastrointestinal | regorafenib | Abl family, BRAF, BRAF V600E, CRAF, CSF-1R, DDR2, EphA2, FGFR1, FGFR2, FRK, MAPK11, PDGFRa, PDGFRb, RET,TRKA, Tie-2, VEGFR1, VEGFR2, VEGFR3, c-kit |
| Liver and bile duct | regorafenib | Abl family, BRAF, BRAF V600E, CRAF, CSF-1R, DDR2, EphA2, FGFR1, FGFR2, FRK, MAPK11, PDGFRa, PDGFRb, RET,TRKA, Tie-2, VEGFR1, VEGFR2, VEGFR3, c-kit |
| Skin | retifanlimab-dlwr | PD-1 |
| Breast | ribociclib | CDK4, CDK6 |
| Gastrointestinal | ripretinib | EGFR + PDGFRa + c-Kit |
| Leukemia | rituximab | CD20 + Hyaluronic acid |
| Lymphoma | rituximab | CD20 + Hyaluronic acid |
| Leukemia | rituximab and hyaluronidase human | CD20 + Hyaluronic acid |
| Lymphoma | rituximab and hyaluronidase human | CD20 + Hyaluronic acid |
| Lymphoma | romidepsin | HDAC |
| Ovarian epithelial, fallopian tube, and primary peritoneal | rucaparib camsylate | PARP1 + PARP2 + PARP3 |
| Prostate | rucaparib camsylate | PARP1 + PARP2 + PARP3 |
| Myelodysplastic and myeloproliferative disorders | ruxolitinib phosphate | JAK1 + JAK2 |
| Breast | sacituzumab govitecan-hziy | TOP1 |
| Lymphoma | selinexor | XPO1 |
| Multiple myeloma | selinexor | XPO1 |
| Lung | selpercatinib | RET |
| Solid tumors anywhere in the body | selpercatinib | RET |
| Thyroid | selpercatinib | RET |
| Plexiform neurofibroma | selumetinib sulfate | MEK1 + MEK2 |
| Soft tissue sarcoma | sirolimus protein-bound particles | MUT + mTOR |
| Skin | sonidegib | SMO |
| Kidney | sorafenib tosylate | BRAF inhibitors, CRAF inhibitors, FLT3 + PDGFRβ + RET + VEGFR1 + VEGFR2 + VEGFR3 + c-Kit |
| Liver and bile duct | sorafenib tosylate | BRAF + CRAF + FLT3 + PDGFRβ + RET + VEGFR1 + VEGFR2 + VEGFR3 + c-Kit |
| Thyroid | sorafenib tosylate | BRAF + CRAF + FLT3 + PDGFRβ + RET + VEGFR1 + VEGFR2 + VEGFR3 + c-Kit |
| Lung | sotorasib | KRAS G12C |
| Gastrointestinal | sunitinib malate | PDGFR + RTK + VEGFR |
| Kidney | sunitinib malate | PDGFR + RTK + VEGFR |
| Pancreatic | sunitinib malate | PDGFR + RTK + VEGFR |
| Lymphoma | tafasitamab-cxix | CD19 |
| Leukemia | tagraxofusp-erzs | CD123 |
| Breast | talazoparib tosylate | PARP1, PARP2 |
| Breast | tamoxifen citrate | ER |
| Lymphoma | tazemetostat hydrobromide | EZH2 |
| Soft tissue sarcoma | tazemetostat hydrobromide | EZH2 |
| Skin | tebentafusp-tebn | CD3 + gp100 |
| Multiple myeloma | teclistamab-cqyv | CD3 + gp100 |
| Kidney | temsirolimus | CD3 + gp100 |
| Lung | tepotinib hydrochloride | MET |
| Leukemia | tisagenlecleucel | CD19 |
| Lymphoma | tisagenlecleucel | CD19 |
| Cervical | tisotumab vedotin-tftv | Tubulin, tissue factor |
| Kidney | tivozanib hydrochloride | (VEGFR)-1, VEGFR-2 and VEGFR-3, c-kit, and PDGFR β |
| Breast | toremifene | ER |
| Brain | trametinib | MEK1 and MEK2 |
| Lung | trametinib dimethyl sulfoxide | MEK1 and MEK2 |
| Skin | trametinib dimethyl sulfoxide | MEK1 and MEK2 |
| Solid tumors anywhere in the body | trametinib dimethyl sulfoxide | MEK1 and MEK2 |
| Thyroid | trametinib dimethyl sulfoxide | MEK1 and MEK2 |
| Breast | trastuzumab | HER2 |
| Esophageal | trastuzumab | HER2 |
| Stomach (gastric) | trastuzumab | HER2 |
| Liver and bile duct | tremelimumab-actl | CTLA-4, CD80, and CD86 |
| Lung | tremelimumab-actl | CTLA-4, CD80, and CD86 |
| Breast | tucatinib | HER2 |
| Colorectal | tucatinib | HER2 |
| Thyroid | vandetanib | VEGFR-2, EGFR, RET |
| Skin | vemurafenib | BRAF, BRAF V600E, CRAF, ARAF, SRMS, ACK1, MAP4K5, FGR |
| Leukemia | venetoclax | BCL-2 |
| Lymphoma | venetoclax | BCL-2 |
| Lymphoma | vorinostat | HDAC1, HDAC2 and HDAC3 (Class I) and HDAC6 (Class II) |
| Leukemia | zanubrutinib | BTK |
| Lymphoma | zanubrutinib | BTK |
| Colorectal | ziv-aflibercept | PGF, VEGF-A |

In some embodiments, the methods provided herein provide a deeper understanding of the changes in DNA and proteins that cause cancer, allowing the identification of biomarkers and design of treatments that target these proteins. In some embodiments, the biomarker may include an epigenetic signature, such as a methylation state, methylation score and/or DNA fragmentation pattern/score. In some embodiments, the epigenetic signature can be determined for one or more regions that include, but not limited to, transcription start sites, promoter regions, CTCF binding regions and regulatory protein binding regions. In some embodiments, the epigenetic signature is determined for one or more regions that include, but not limited to, transcription start sites, promoter regions, intergenic regions and/or intronic regions associated with at least one or more disease-related gene. Such treatments may include small-molecule drugs or monoclonal antibodies. The methods may also improve biomarker testing in individuals suffering from disease and help determine if the individual is a candidate for a certain drug or combination of drugs based on the presence or absence of the biomarker. Additionally, the methods can improve identification of mutations that contribute to the development of resistance to targeted therapy. Consequently, the analysis techniques may reduce unnecessary or untimely therapeutic interventions, patient suffering, and patient mortality.

The interplay of chemical modifications to DNA and histone proteins, known as the epigenome, plays a significant role in modulating gene expression in health and disease including cancer. Epigenetic changes in connection with genetic alterations contribute to the acquisition of cancer hallmarks such as sustaining proliferative signaling, evading growth suppressors, resisting cell death, enabling replicative immortality, inducing angiogenesis, and activating invasion and metastasis (Hanahan, D. 2022). Given the reversible nature of epigenetic modifications, understanding these mechanisms offers promising avenues for therapeutic intervention, with several epigenetic drugs already approved or in clinical trials for the treatment of cancer.

In some embodiments, one or more epigenetic biomarkers determined by the methods described herein to be present or absent in a sample from the subject is used to guide treatment for the subject. Epigenetic biomarkers for targeted therapy may be particularly valuable for patients who do not exhibit a genetic druggable target. The FDA has approved several epigenetic drugs including DNA methyltransferase (DNMT) inhibitors, Histone deacetylase (HDAC) inhibitors, Lysine methyltransferase inhibitors, Lysine demethylase inhibitors, and Bromodomain inhibitors. 5-azacytidine is a DNA methyltransferase inhibitor used for myelodysplastic syndrome. Decitabine is also a DNA methyltransferase inhibitor used for myelodysplastic syndrome. Vorinostat, an HDAC inhibitor, is indicated for cutaneous T-cell lymphoma, while romidepsin, another HDAC inhibitor, is also used for cutaneous T-cell lymphoma. Belinostat, an HDAC inhibitor, is prescribed for peripheral T-cell lymphoma, and panobinostat, also an HDAC inhibitor, is used for multiple myeloma. Tazemetostat, an EZH2 (KMT inhibitor), is indicated for epithelioid sarcoma and follicular lymphoma. Ivosidenib, an IDH inhibitor, is used for acute myeloid leukemia and cholangiocarcinoma, while enasidenib, another HD inhibitor, is used for acute myeloid leukemia. Tranylcypromine, a lysine demethylase inhibitor, is indicated for acute myeloid leukemia and myelodysplastic syndrome. Chidamide, an HDAC inhibitor, is used for breast cancer and peripheral T-cell lymphoma, while valemetostat, an EZH2/EZH1 inhibitor, is prescribed for adult T-cell leukemia/lymphoma. Azacitidine, a DNMT1 inhibitor, is used for juvenile myelomonocytic leukemia. Decitabine, another DNMT1 inhibitor, is indicated for myelodysplastic syndrome and chronic myelomonocytic leukemia. Additionally, 5-azacytidine, as a DNA methyltransferase inhibitor, is used for colorectal cancer (immunotherapy sensitization). Decitabine, also a DNA methyltransferase inhibitor, enhances PD-L1 efficacy and immune response in colorectal cancer. Tazemetostat, as an EZH2 inhibitor, has potential to enhance immunotherapy in colorectal cancer. Lastly, TMP195, an HDAC inhibitor, is used for colorectal cancer, focusing on macrophage polarization and enhancing PD-1 inhibitors.

DNA Methyltransferase Inhibitors (DNMTi)-inhibit DNA methyltransferases, enzymes that add methyl groups to DNA, typically silencing gene expression. DNMTi drugs include Azacitidine (Vidaza®) which was approved for the treatment of myelodysplastic syndromes (MDS) and Decitabine (Dacogen®) also approved for MDS. Histone Deacetylase Inhibitors (HDACi) inhibit histone deacetylases, enzymes that remove acetyl groups from histone proteins, typically leading to a closed chromatin structure and gene silencing. Inhibiting these enzymes can reactivate silenced genes beneficial in cancer treatment. HDACi drugs include Vorinostat (Zolinza®) approved for the treatment of cutaneous T cell lymphoma (CTCL), Romidepsin (Istodax®) approved for CTCL and peripheral T-cell lymphoma (PTCL), Belinostat (Beleodaq®) approved for PTCL, and Panobinostat (Farydak®) approved for multiple myeloma in combination with bortezomib and dexamethasone. EZH2 Inhibitors, EZH2 is a component of the polycomb repressive complex 2 (PRC2) that methylates histone H3 on lysine 27 (H3K27me3), leading to gene silencing. EZH2 Inhibitors include Tazemetostat (Tazverik®) approved for the treatment of epithelioid sarcoma and follicular lymphoma. Additional epigenetic drugs include Bromodomain Inhibitors that target bromodomains, which recognize acetylated lysine residues on histone tails, influencing chromatin structure and gene expression; however, currently there are no bromodomain inhibitors approved by the FDA.

In some embodiments, the subject is treated with one or more epigenetic-targeted drugs. In some embodiments, the epigenetic-targeted drug is selected from HDAC inhibitors, HDAC agonists, IDH inhibitors, EZHR inhibitors, DNMT inhibitors, METTL3 inhibitors, METTL3 agonists, FTO inhibitors, FTO agonist, ALKBH5 inhibitors, YTHDF inhibitors, IFG2BP inhibitors, JmjC-KDM inhibitors, LSD1 inhibitors, TET agonists, TET inhibitors, MBD inhibitors, UHRF1 inhibitors, KAT inhibitors, SIRT inhibitors, SIRT agonists, BET inhibitors, YEATS domain inhibitors, KMT inhibitors, PRMT inhibitors, inhibitors targeting SWI/SNF complexes (e.g., allosteric inhibitors), and inhibitors targeting specific subunits of SWI/SNF complexes (e.g. targeting ATPase components, targeting bromodomain).

XIII. Kits

Any or all of the reagents for performing the above-described methods, such as sets of sample and partition indexes, buffers, enzymes, adapters, primers and vessels for holding samples, pooled samples or partitioned pooled samples, can be included in a kit.

XIV. Computer Implementation

The present methods can be computer-implemented, such that any or all of the steps described in the specification or appended claims other than wet chemistry steps can be performed in a suitable programmed computer. The computer can be a mainframe, personal computer, tablet, smart phone, cloud, online data storage, remote data storage, or the like. The computer can be operated in one or more locations. A computer program can include codes for performing any of the steps other than wet chemistry steps described in the specification or in the appended claims.

The present methods can be implemented in a system (e.g., a data processing system) for analyzing a nucleic acid population. The system can also include a processor, a system bus, a main memory and optionally an auxiliary memory coupled to one another to perform one or more of the steps described in the specification or appended claims, such as the following: obtaining sequencing reads of the amplicons, segregating the sequence reads according to the sample of origin and aliquot of origin from a sample index, partition index and start and stop points of nucleic acid molecule sequence to produce for each sample a plurality of families of sequencing reads, the families corresponding to different original molecules, calling out genetic variations, if present, for different samples from the plurality of families of sequencing reads for a sample and calling out consensus nucleotides or consensus sequence in a family based on the sequencing reads in that family.

The system can also include a keyboard and/or pointer for providing user input, such as, among other accessories. The system can also include a sequencing apparatus coupled to the memory to provide raw sequencing data.

Various steps of the present methods can utilize information and/or programs and generate results that are stored on computer-readable media (e.g., hard drive, auxiliary memory, external memory, server; database, portable memory device (e.g., CD-R, DVD, ZIP disk, flash memory cards), and the like. For example, information used for and results generated by the methods that can be stored on computer-readable media include control data references sequences, raw sequencing data, sequenced nucleic acids, mutations.

All publications, patents and patent applications, accession numbers, websites and the like mentioned in this specification are incorporated by reference in their entireties for all purposes to the same extent as if each individual publication, patent or patent application was so individually denoted. To the extent more different content is associate with an accession number or other reference at different times, the content in effect as of the effective filing date of this application is meant. The effective filing date is the date of the earliest priority application disclosing the accession number in question. Unless otherwise apparent from the context any element, embodiment, step, feature or aspect of the invention can be performed in combination with any other, and steps can be performed in various orders beyond those exemplified.

EXAMPLES

Examples 1 and 2

Figure 2:
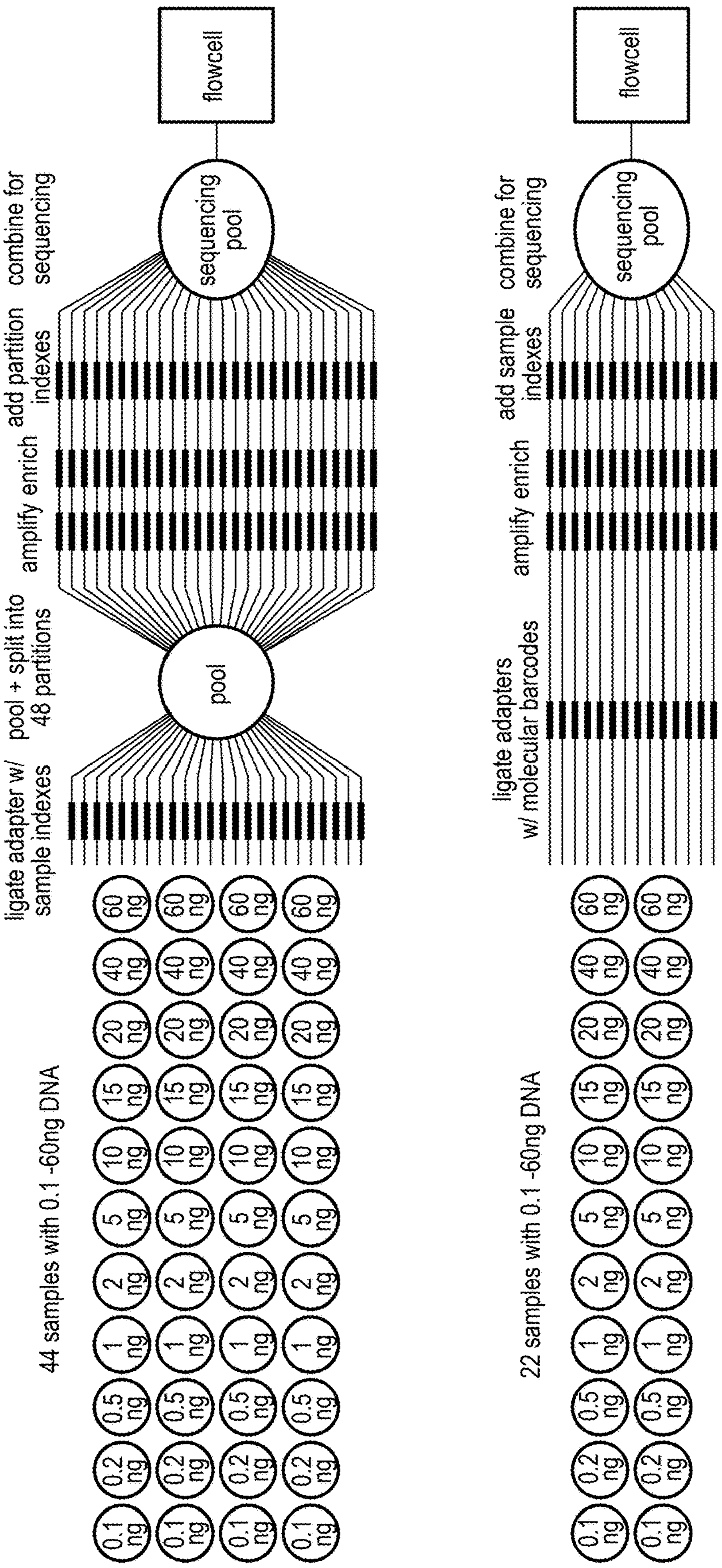
FIG. 2 show two protocols; upper exemplary protocol according to the invention and lower for reference.
Figure 3:
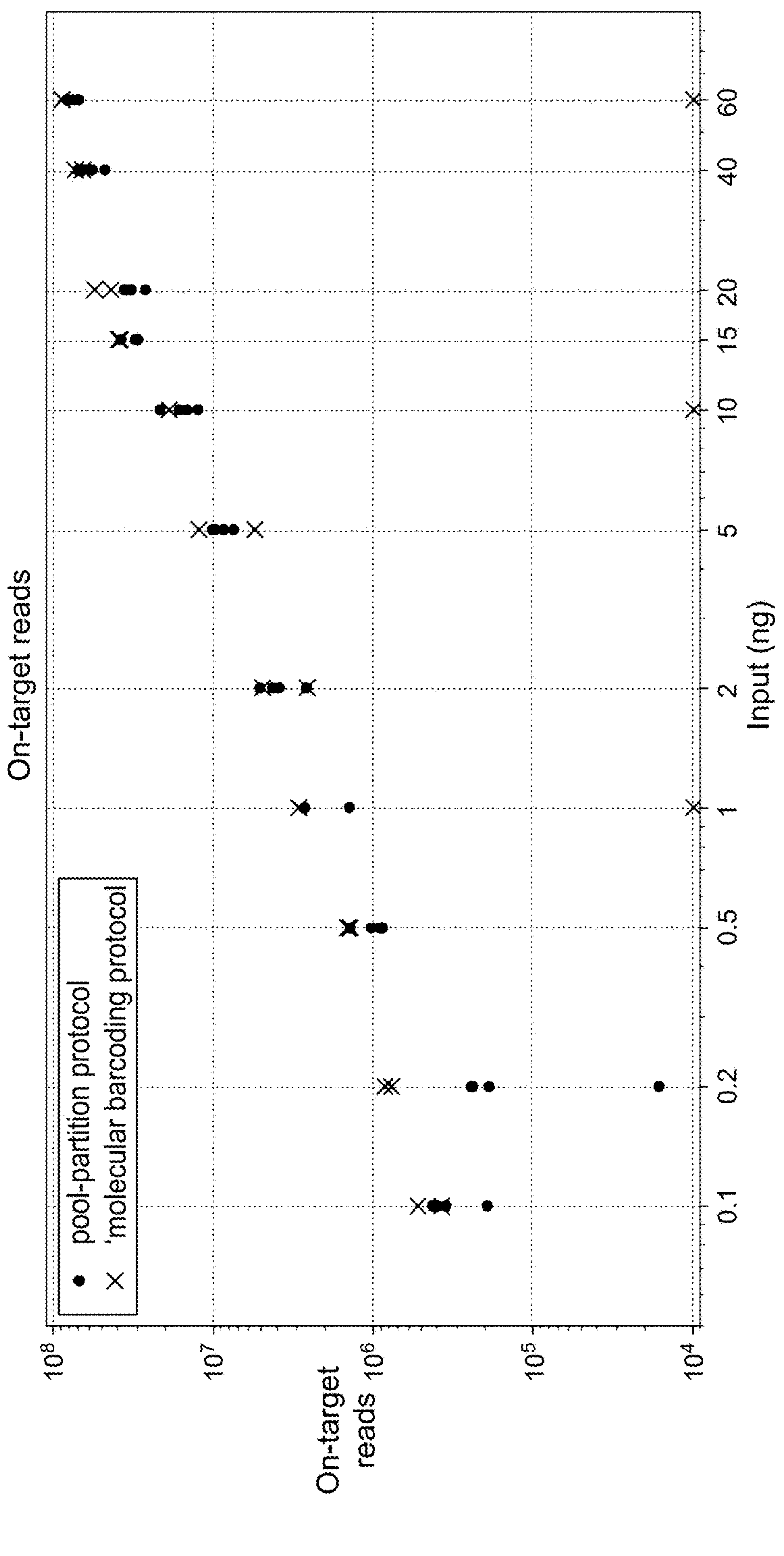
FIG. 3 shows on-target reads as a function of input DNA for the two protocols.
Figure 4:
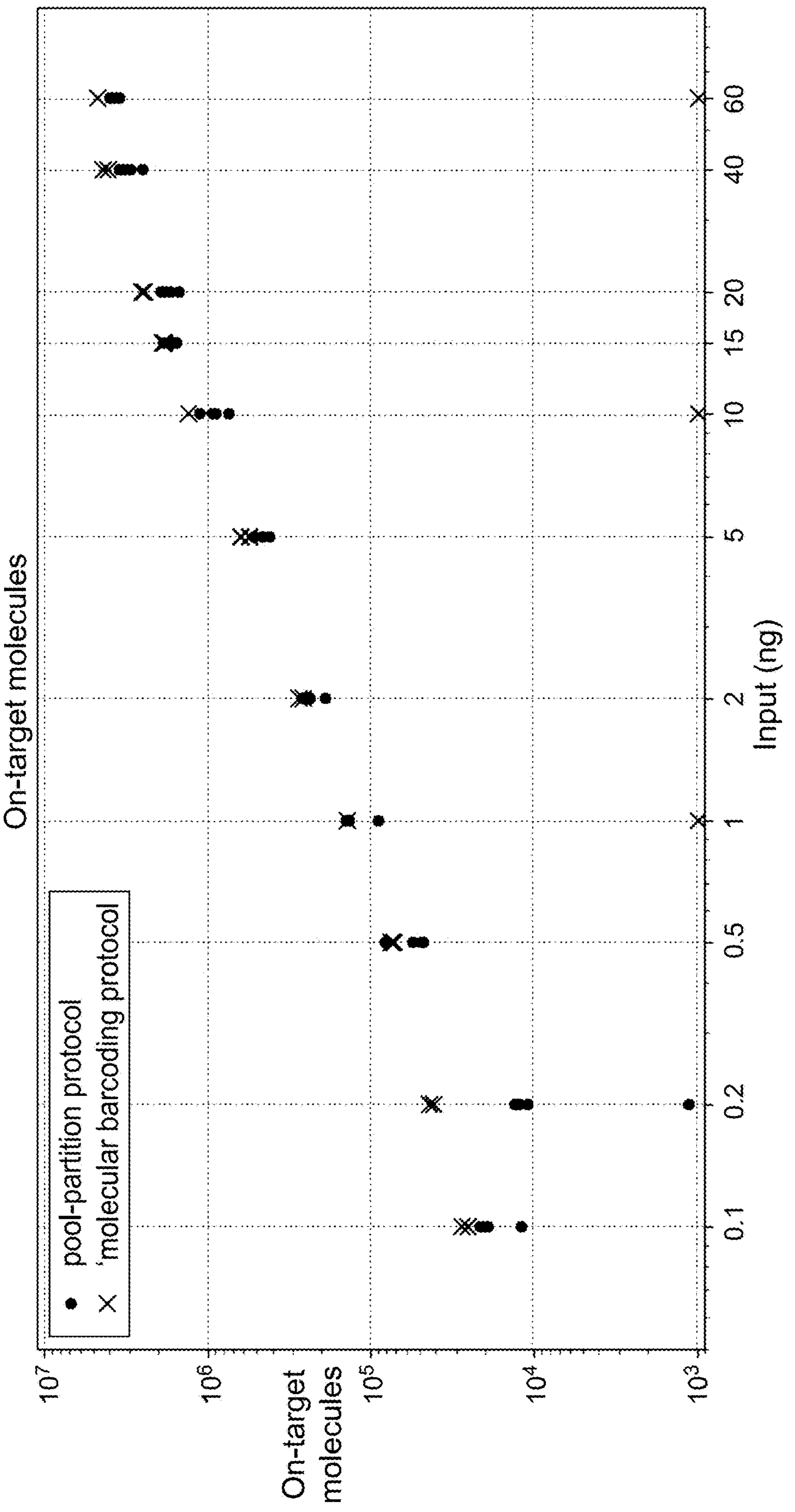
FIG. 4 shows on-target molecules as a function of input DNA for the two protocols.
Figure 5:
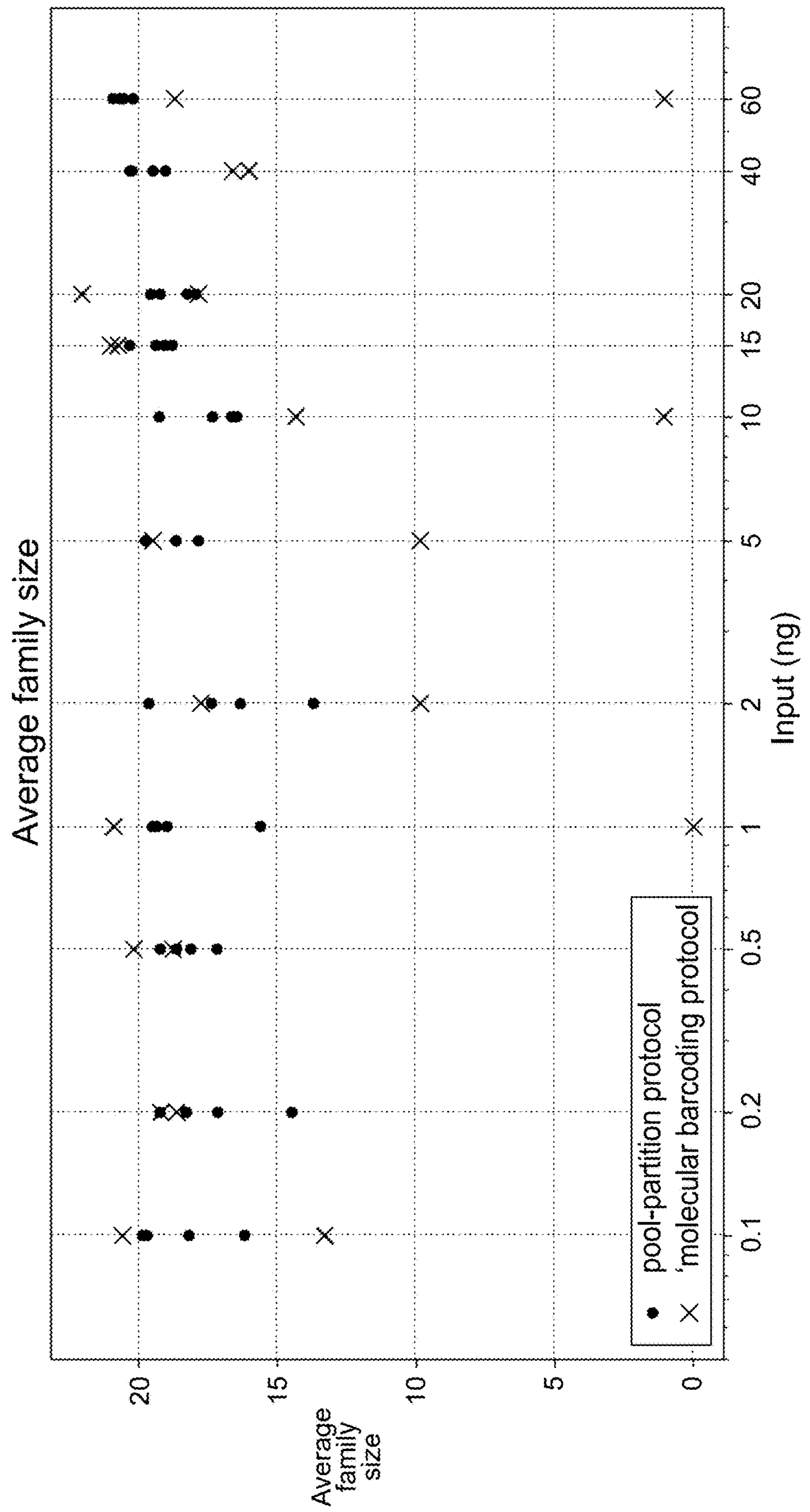
FIG. 5 shows average family size as a function of input DNA for the two protocols.
Figure 6:
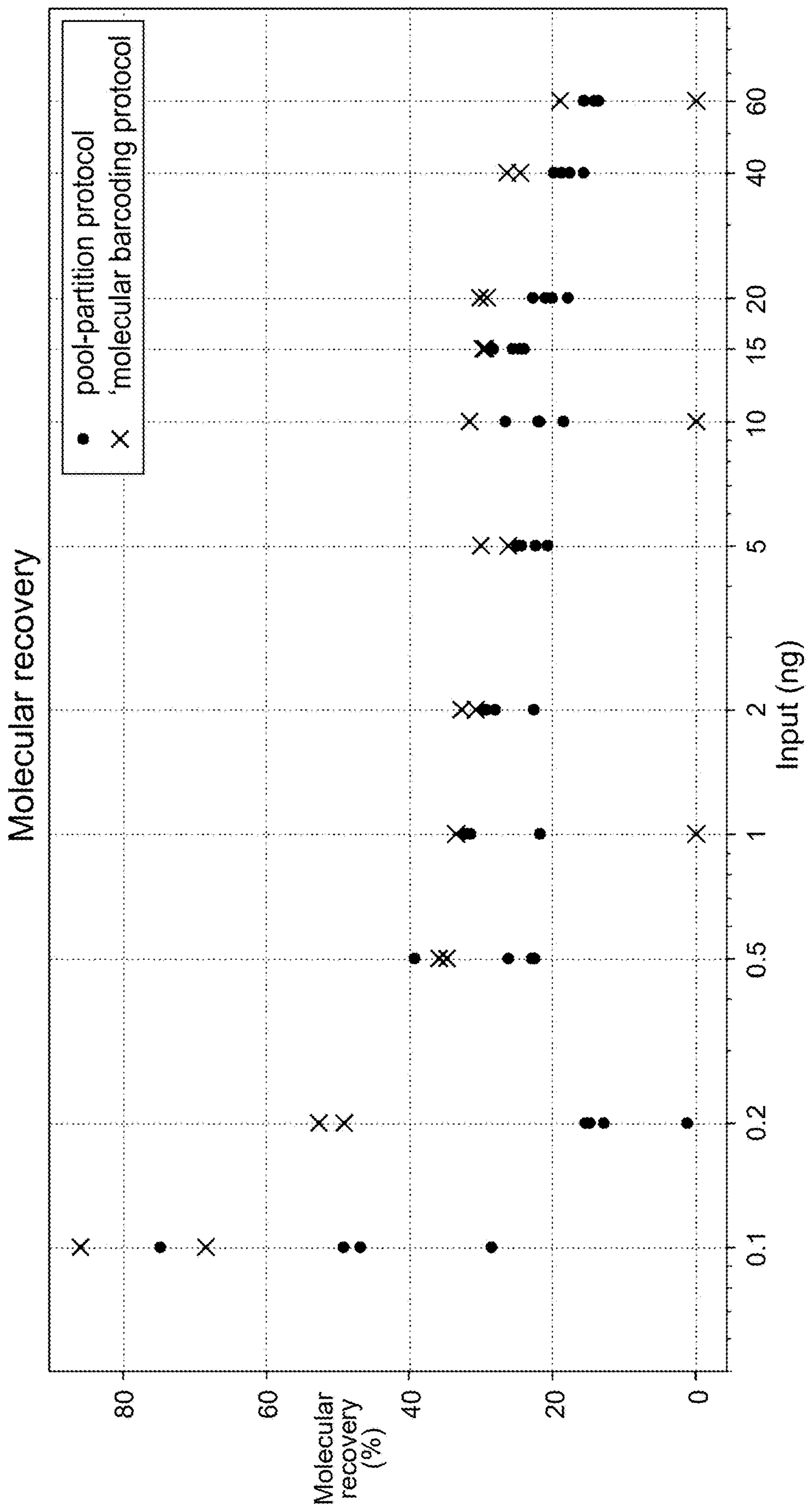
FIG. 6 shows percent molecular recovery as a function of input DNA for the two protocols.
Figure 7:
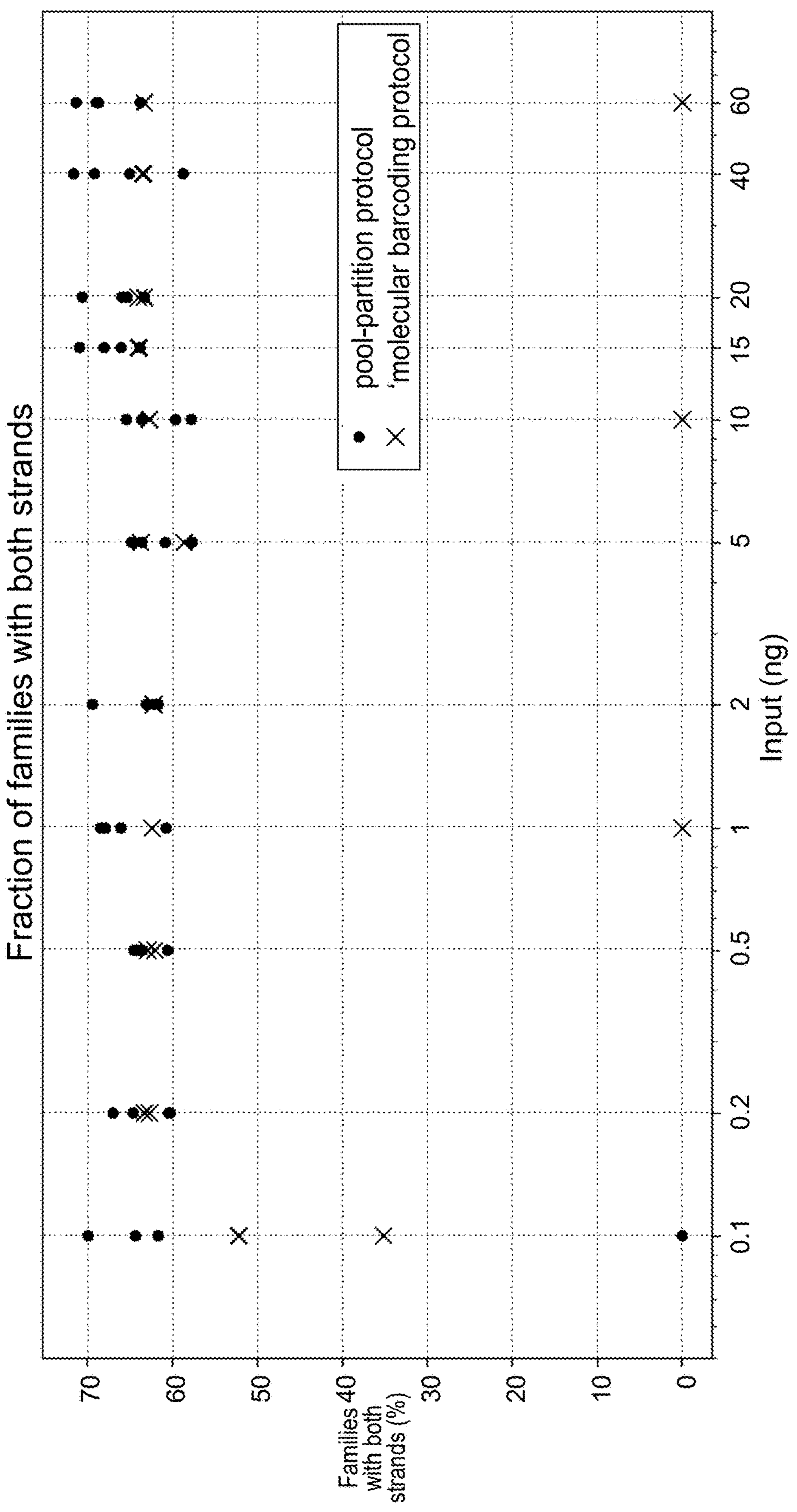
FIG. 7 shows fractions of families with both strands as a function of input DNA.

Example 1 compares sequencing results from two protocols, one according to the invention and the other a reference. FIG. 2 shows the respective workflows. The first protocol was performed on 44 samples containing 11 different amounts of DNA (4× for each amount). Samples were ligated with a sample index and pooled. The pool was split into 48 partitions. The DNA was amplified and enriched for molecules hybridizing to designated genomic areas. Partition indexes were then added. The aliquots were then combined for sequencing. The reference protocol was performed on 11 different amounts of DNA (2× for amount). Samples were ligated with molecular barcodes, which randomly assort to DNA molecules in the samples, amplified and enriched. Sample indexes were then added, and the samples pooled for sequencing. FIG. 3 shows the on-target number of sequencing reads (i.e., within a designated genomic region) relative to input DNA. In each protocol, there was a linear increase in on target sequencing reads with input DNA. There was no significant difference between the two protocols. FIG. 4 shows similar information but is the number of on-target nucleic molecules rather than sequencing reads. Again, there is an increase in number of molecules with input DNA and no significant difference between the two protocols. FIG. 5 shows average family size for the two protocols with increasing DNA. The first protocol (according to the invention) shows more uniform family sizes with no significant outliers, while the second protocol has more variable family sizes and outliers. FIG. 6 compares molecular recovery, i.e., percent of sample nucleic acids sequence. There was no significant difference between the protocols. FIG. 7 shows the fraction of families with sequencing reads of both strands. The partition method has more families with sequencing reads on both strands.

Figure 9:
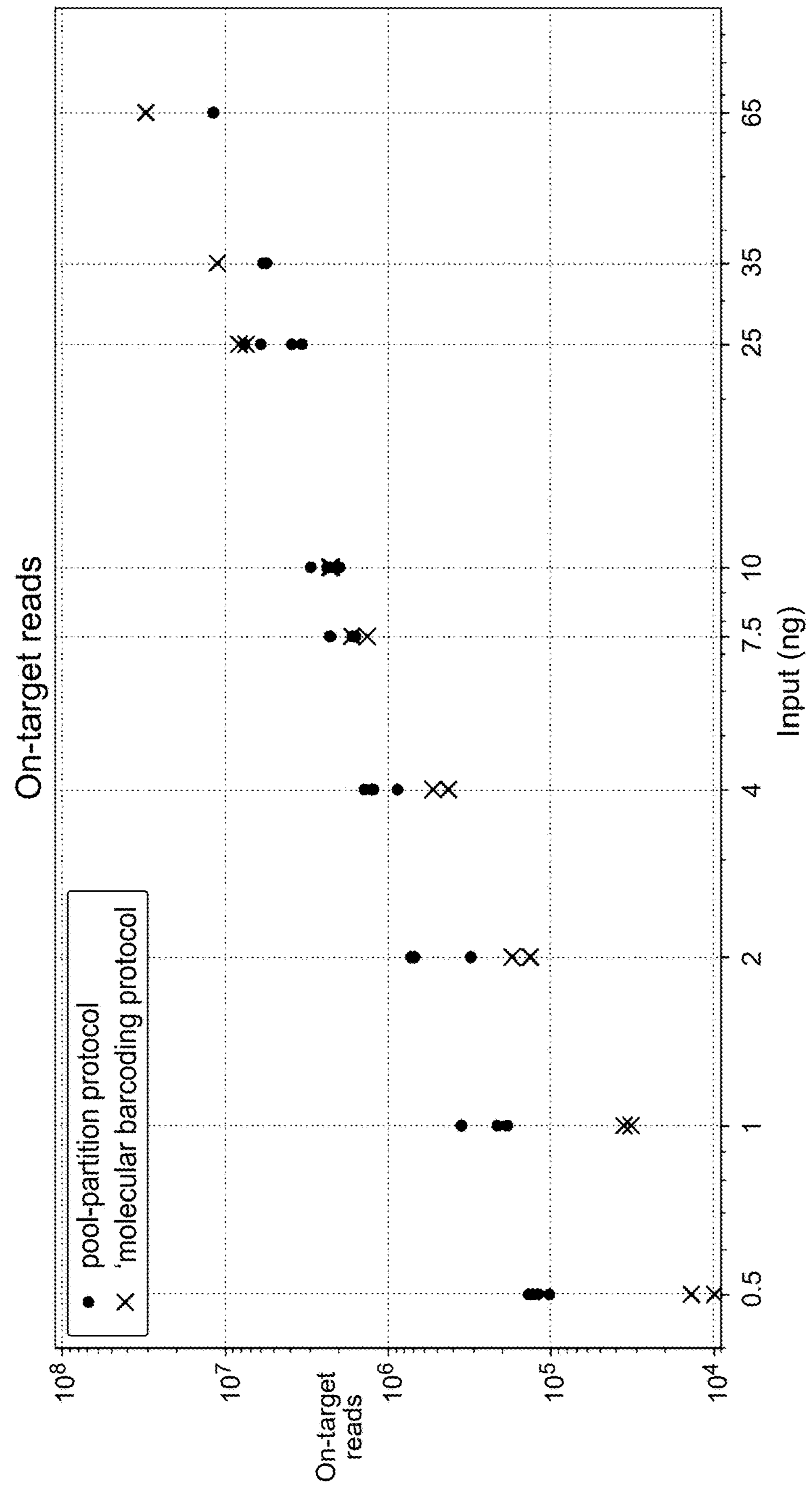
FIG. 9 shows on-target reads from the workflow of FIG. 8.
Figure 10:
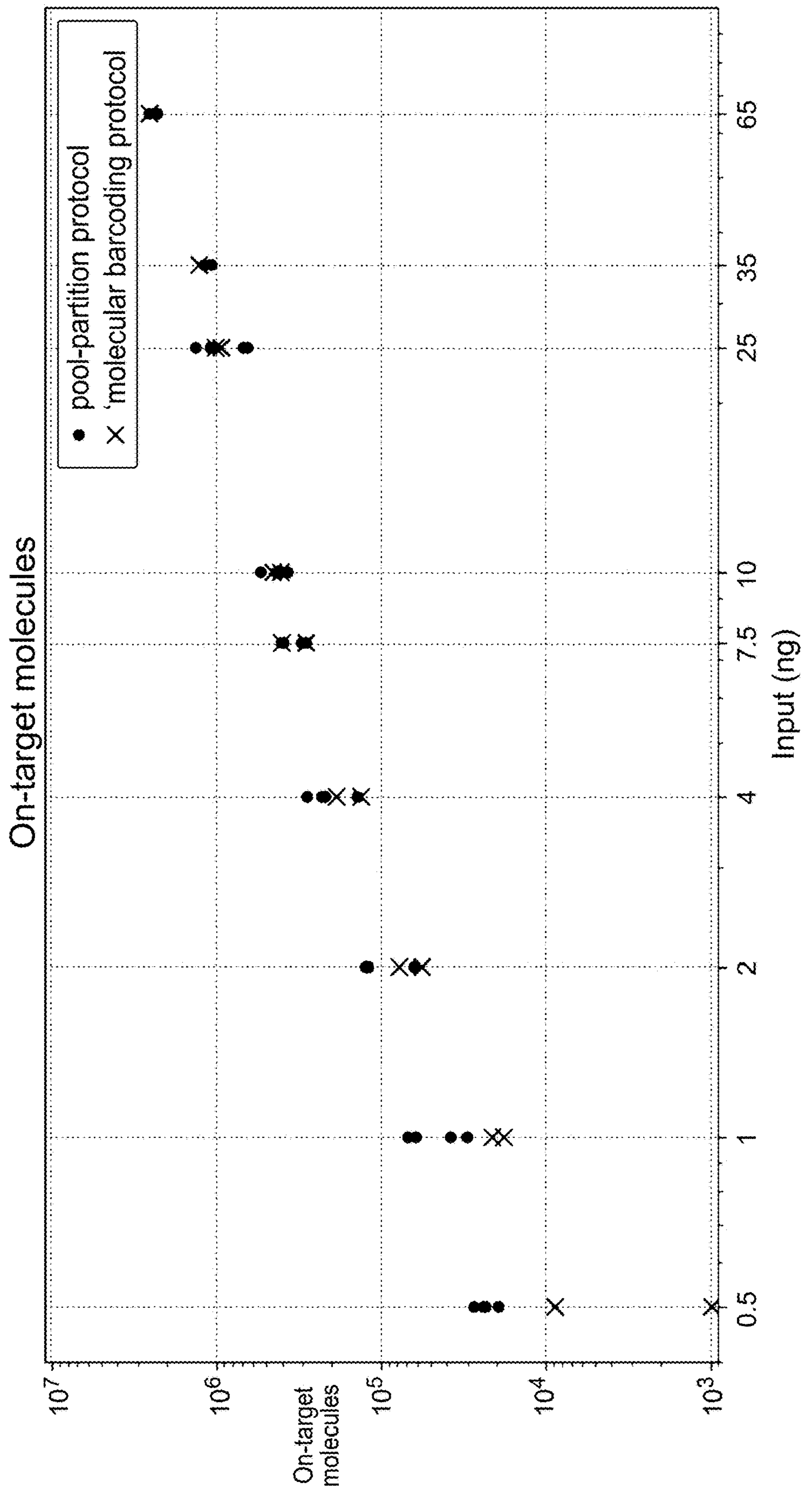
FIG. 10 shows on target molecules from the workflow of FIG. 8.
Figure 11:
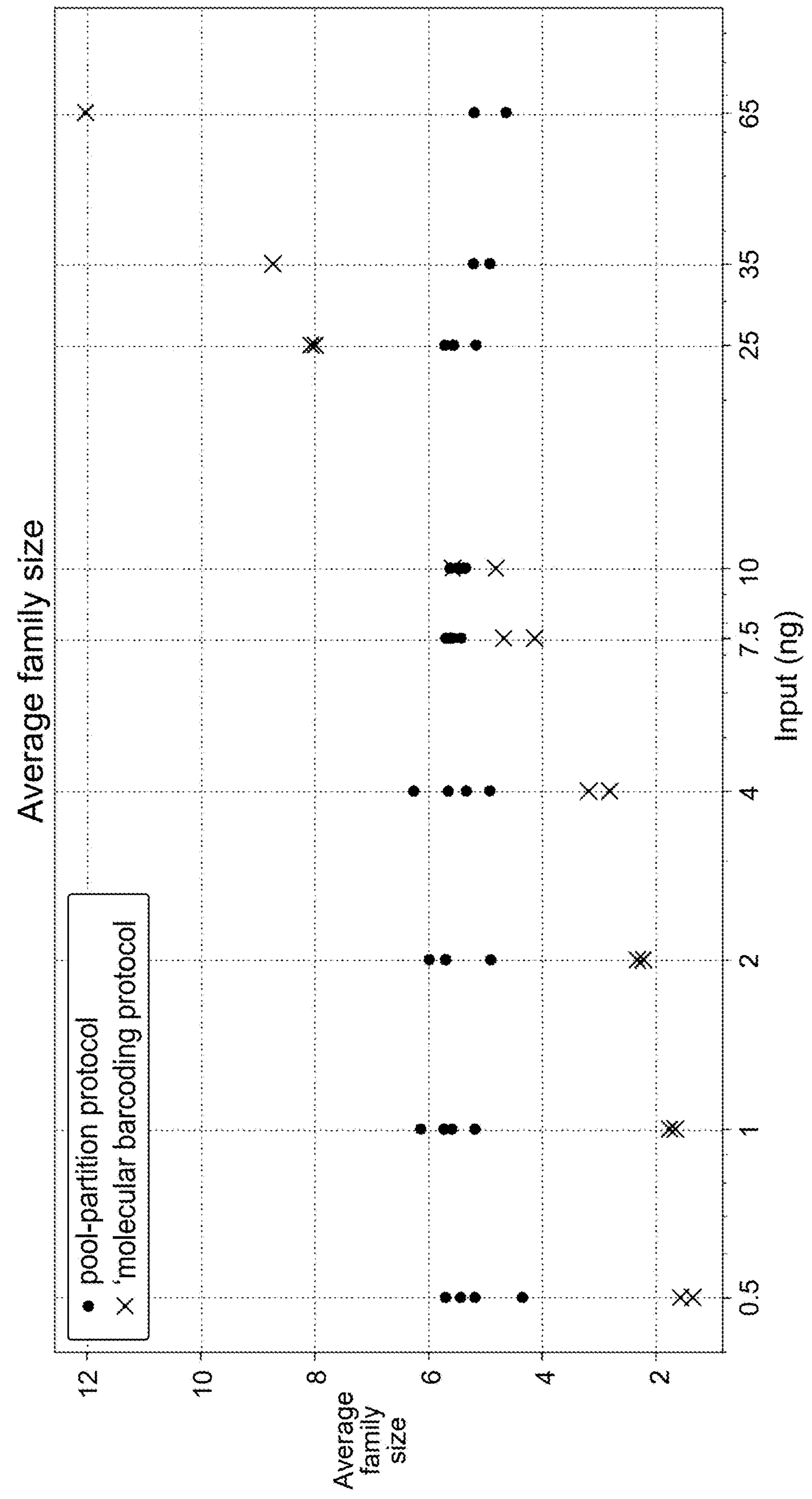
FIG. 11 shows average family size from the workflow of FIG. 8.

Example 2 shows a similar experiment to Example 1 except that samples are subject to conversion of unmethylated C's. This method detects 5mC and 5hmC using two sets of enzymatic reactions. In the first reaction, TET2 and T4-BGT convert 5mC and 5hmC into products that cannot be deaminated by APOBEC3A. In the second reaction, APOBEC3A deaminates unmodified cytosines by converting them to uracils. FIG. 8 shows two protocols. The first protocol was performed on 32 samples containing 8 different amounts of DNA (4× for each amount). Samples were ligated with a sample index and pooled. The pool was split into 48 partitions. The DNA was subjected to methylation conversion in the separate partitions and then amplified and enriched for molecules hybridizing to designated genomic areas. Partition indexes were then added. The aliquots were then combined for sequencing. The reference protocol was performed on 8 different amounts of DNA (2× for amount). Samples were ligated with molecular barcodes, which randomly assort to the DNA molecules in the samples, subjected to base conversion, amplified and enriched. Sample indexes were then added, and the samples pooled for sequencing. FIG. 9 shows the on-target number of sequencing reads (i.e., within a designated genomic region) relative to input DNA. In each protocol, there was a linear increase in on target sequencing reads with input DNA. The pool partition method resulted in more on-target reads at lower input DNA. FIG. 10 shows similar information but is the number of on-target nucleic molecules rather than sequencing reads. Again, there is an increase in number of molecules with input DNA and small increase in on-target molecules for the pool partition method. FIG. 11 shows average family size for the two protocols with increasing DNA. The average family sizes are much more uniform across samples in the partition method, regardless of DNA input, which should result in more accuracy of variant calling or at least prevent entire samples from dropping out. The number of families is also more linear with the input DNA, which is another consequence of stable family sizes, which should allow much better dynamic range of the test including more accurate copy number variation calling.

What is claimed is:

1. A method of sequencing, comprising:

(a) linking sample indexes to nucleic acid molecules in a plurality of samples, wherein nucleic acid molecules in a same sample receive a same sample index and nucleic acid molecules in different samples receive different sample indexes;

(b) pooling the nucleic acid molecules from the plurality of samples;

(c) partitioning the pooled nucleic acid molecules into a plurality of aliquots;

(d) labelling the nucleic acid molecules with partition indexes, wherein nucleic acid molecules in the same aliquot receive the same partition index and nucleic acid molecules in different aliquots receive different partition indexes;

(e) amplifying the nucleic acid molecules in separate aliquots to produce amplicons;

(f) pooling at least some of the amplicons from the aliquots;

(g) sequencing the amplicons to produce sequencing reads, wherein a sequencing read comprises a sequence of one of the nucleic acid molecules, a sample index, and a partition index;

(h) aligning the sequencing reads to a reference sequence to determine start and stop points and/or lengths of the sequences of the nucleic acid molecules;

(i) grouping sequencing reads with the same sample index into families, wherein sequencing reads in the same family have the same start and stop points and/or same length determined in (h), and the same partition index; and (j) calling sequences or variants present in at least one sample of the plurality of samples from the sequencing reads grouped into families.

2. The method of claim 1, wherein step (j) determines a consensus sequence from the sequencing reads in a family.

3. The method of claim 1, wherein the sequencing reads include sequencing reads of both strands in a family.

4. The method of claim 3, wherein step (j) comprises calling a variation when the variation is present in the sequencing reads of both strands.

5. The method of claim 1, wherein step (j) comprises calling a variation when the variation is present in sequencing reads of multiple families.

6. The method of claim 1, wherein the number of aliquots is 2-1500.

7. The method of claim 1, wherein the number of aliquots is 5-500.

8. The method of claim 1, wherein the number of aliquots is 25-100.

9. The method of claim 1, wherein the number of aliquots is 96 or 384.

10. The method of claim 1, wherein the sample indexes have a Hamming distance of at least two from one another and the partition indexes have a Hamming distance of at least two from one another.

11. The method of claim 1, wherein the plurality of samples are cell-free DNA samples.

12. The method of claim 11, further comprising blunt-ending DNA molecules in the cell-free DNA samples.

13. The method of claim 1, further comprising enriching for DNA molecules from selected regions of a genome after the amplifying step.

14. The method of claim 1, further comprising converting unmethylated C's to U's after partitioning and before amplifying.

15. The method of claim 1, wherein either prior to step (a) or after step (a) and before step (b), the nucleic acid molecules in one or more samples are contacted with a methyl binding reagent.

16. The method of claim 1, wherein the sample includes at least 100 billion different molecules and has an estimated mean number of molecules of the same start and stop points of between 1.5 and 3 and an estimated maximum number of molecules of the same start and stop points of between 100 and 1000.

17. The method of claim 1, wherein the partition indexes are components of a forward and/or a reverse primer.

18. The method of claim 1, wherein the sample indexes are components of an adapter.

19. The method of claim 1, wherein the samples are samples from different subjects.

20. The method of claim 1, performed without random association of indexes with sample nucleic acids.

* * * * *